(12) United States Patent
Filikov et al.

(10) Patent No.: US 6,946,265 B1
(45) Date of Patent: Sep. 20, 2005

(54) NUCLEIC ACIDS AND PROTEINS WITH GROWTH HORMONE ACTIVITY

(75) Inventors: Anton Filikov, Monrovia, CA (US); Bassil I. Dahiyat, Los Angeles, CA (US)

(73) Assignee: Xencor, Inc., Monrovia, CA (US)

( * ) Notice: Subject to any disclaimer, the term of this patent is extended or adjusted under 35 U.S.C. 154(b) by 0 days.

(21) Appl. No.: 09/571,024

(22) Filed: May 12, 2000

Related U.S. Application Data
(60) Provisional application No. 60/133,784, filed on May 12, 1999.

(51) Int. Cl.$^7$ ........................ C12N 15/09; C12N 15/00; A61K 38/24; A61K 38/27; C07H 21/04

(52) U.S. Cl. .................. 435/69.4; 435/69.1; 435/320.1; 424/198.1; 530/350; 530/399; 536/23.51; 536/23.1; 536/23.5; 514/12

(58) Field of Search .............................. 435/69.4, 69.1, 435/320.1, 325; 424/198.1; 530/350, 399; 536/23.51, 23.1, 23.5; 514/12, 2

(56) References Cited

U.S. PATENT DOCUMENTS

| | | | |
|---|---|---|---|
| 4,658,021 A | 4/1987 | Goeddel et al. | 530/399 |
| 4,665,160 A | 5/1987 | Seeburg | 530/399 |
| 5,068,317 A | 11/1991 | Becker et al. | 530/399 |
| 5,079,345 A | 1/1992 | Becker et al. | 530/399 |
| 5,424,199 A | 6/1995 | Goeddel et al. | 435/69.4 |
| 5,506,107 A * | 4/1996 | Cunningham et al. | 435/7.21 |
| 5,534,617 A | 7/1996 | Cunningham et al. | 530/399 |
| 5,580,723 A * | 12/1996 | Wells et al. | 435/6 |
| 5,597,709 A | 1/1997 | Rosen et al. | 435/69.4 |
| 5,612,315 A | 3/1997 | Pikal et al. | 514/21 |
| 5,633,352 A | 5/1997 | Dalbøge et al. | 530/399 |
| 5,635,604 A | 6/1997 | Dalbøge et al. | 530/399 |
| 5,688,666 A | 11/1997 | Bass et al. | 435/69.4 |
| 6,188,965 B1 | 2/2001 | Mayo et al. | |
| 6,269,312 B1 | 7/2001 | Mayo et al. | |
| 6,403,312 B1 | 6/2002 | Dahiyat et al. | |
| 6,708,120 B1 | 3/2004 | Mayo et al. | |
| 6,780,613 B1 | 8/2004 | Wells et al. | |
| 2001/0032052 A1 | 10/2001 | Mayo et al. | |
| 2001/0039480 A1 | 11/2001 | Mayo et al. | |
| 2002/0004706 A1 | 1/2002 | Mayo et al. | |
| 2002/0048772 A1 | 4/2002 | Dahiyat et al. | |
| 2002/0090648 A1 | 7/2002 | Dahiyat et al. | |
| 2002/0106694 A1 | 8/2002 | Mayo et al. | |
| 2003/0049654 A1 | 3/2003 | Dahiyat et al. | |
| 2003/0130827 A1 | 7/2003 | Bentzien et al. | |
| 2004/0043429 A1 | 3/2004 | Dahiyat et al. | |
| 2004/0043430 A1 | 3/2004 | Dahiyat et al. | |

FOREIGN PATENT DOCUMENTS

| | | |
|---|---|---|
| EP | 0 974 111 B1 | 1/2000 |
| WO | 97/11178 A1 | 3/1997 |
| WO | 98/47089 | 10/1998 |
| WO | WO 00/23564 A2 | 4/2000 |
| WO | WO 01/59066 A3 | 8/2001 |
| WO | WO 01/59066 A2 | 8/2001 |
| WO | WO 03/014325 A3 | 2/2003 |
| WO | WO 03/014325 A2 | 2/2003 |

OTHER PUBLICATIONS

Nicoll et al., 1986, Endocrine Reviews, vol. 7, No. 2, pp. 169–203.*
Cunningham et al., 1991, Proc.Natl.Acad.Sci,USA, vol. 88, pp. 3407–3411.*
Lowman and Wells, "Affinity Maturation of Human Growth Hormone by Monovalent Phage Disply" *J. Mol. Biol.* 234:564–578 (1993).
U.S. Appl. No. 09/127,926, filed Jul. 7, 1998, Mayo et al.
Nicoll et al., "Structural Features of Prolactins and Growth Hormones That Can be Related to Their Biological Properties", *Endocr. Rev.* 7(2):169–203 (1986).
Chawla et al., "Structural Variants of Human Growth Hormone: Biochemical, Genetic, and Clinical Aspects", *Annu. Rev. Med.* 34:519–547 (1983).
Edwards, et al., "A Newly Defined Property of Somatotropin: Priming of Macrophages for Production of Superoxide Anion", *Science* 238(4841 Pt1):769–771 (1988).
Thorner and Vance, "Growth Hormone, 1988", *J. Clin. Invest.* 82(3):745–747 (1988).
Leung, et al., "Growth hormone receptor and serum binding protein: purification, cloning and expression", *Nature* 330(6148):537–543 (1987).
Boutin et al., "Cloning and Expression of the Rat Prolactin Receptor, a Member of the Growth Hormone/Prolactin Receptor Gene Family", *Cell* 53(1):69–77 (1988).
Finidori, "Regulators of Growth Hormone Signaling", *Vitam. Horm.* 59:71–97 (2000).
Carter–Su et al., "Signalling Pathway of GH", *Endocr. J.* 43 Suppl:S65–70 (1996).
Campbell, "Growth–hormone signal transduction",*J. Piediatr.* 131(1 Pt2):S42–44 (1997).
Ramaswami et al., "Growth hormone therapy in hypochondroplasia", *Acta. Paediatr.* Suppl. 88(428):116–117 (1999).
Kamp and Wit, "High–Dose Growth Hormone Therapy in Idiopathic Short Stature", *Horm. Res.* 49(suppl. 2):67–72 (1998).
de Meuinck Keizer–Schrama et al., "Growth hormone treatment regimens in girls with Turner syndrome", *Acta. Paediatr.* Suppl. 88(433):126–129 (1999).
Hauesler, "Growth Hormone Therapy in Patients with Turner Syndrome", *Horm. Res.* 49(Suppl. 2):62–66 (1998).
Low et al., "Effect of growth hormone on growth delay in burned children: a 3–year follow–up study", *Lancet* 354(9192):1789 (1999).

(Continued)

*Primary Examiner*—Olga N. Chernyshev
(74) *Attorney, Agent, or Firm*—Dorsey & Whitney LLP; Robin M. Silva

(57) ABSTRACT

The invention relates to novel growth hormone activity (GHA) proteins and nucleic acids. The invention further relates to the use of the GHA proteins in the treatment of growth hormone related disorders.

11 Claims, 13 Drawing Sheets

OTHER PUBLICATIONS

Herndon et al., "Growth Hormone Treatment for Burned Children", *Horm. Res.* 45(Suppl. 1):29–31 (1996).
Bengtsson et al., "The Treatment of Growth Hormone Deficiency in Adults", *J. Clin. Encodrinol. Metab.* 85(3):933–942 (2000).
Cook et al., "The Adult Growth Hormone Deficiency Syndrome", *Adv. Intern. Med.* 45:297–315 (2000).
Welle, "Growth hormone and insulin–like growth factor–I as anabolic agents", *Curr. Opin. Clin. Nutr. Metab. Care* 1(3):257–262 (1998).
Abs, et al., "GH replacement in 1034 growth hormone deficient hypopituitary adults: demographic and clinical characteristics, dosing and safety", *Clinical Endocrinology* 50:703–713 (1999).
Clark and Kendall, "Growth hormone treatment for growth hormone deficient adults", *J. Clin. Pharm. Ther.* 21:367–372 (1996).
Windisch et al., "Recombinant Human Growth Hormone for AIDS–Associated Wasting", *Ann. Pharmacother.* 32(4):437–445 (1998).
Menster et al, "Growth–hormone treatment of renal transplant recipients: The National Cooperative Growth Study experience—A report of the National Cooperative Growth Study and the North American Pediatric Renal Transplant Cooperative Study", *J. Pediatr.* 131(1 Pt2):S20–24 (1997).
Hirschfeld, "Use of Human Recombinant Growth Hormone and Human Recombinant Insulin–Like Growth Factor–I in Patients with Human Immunodeficiency Virus Infection", *Horm. Res.* 46:215–221 (1996).
Cittadini et al., "Growth Hormone and the Heart", *Miner. Electrolyte Metab.* 25:51–55 (1999).
Johnson and Gheorghiade, "Growth hormone therapy in patients with congestive heart failure: Need for further research", *Am. Heart J.* 137(6):989–991 (1999).
Sacca, "Growth hormone: a new therapy for heart failure?", *Bailliere's Clin. Endocrinol. Metab.* 12(2):217–231 (1998).
Gomberg–Maitland and Frishman, "Recombinant growth hormone: A new cardiovascular drug therapy", *Am. Heart J.* 132(6):1244–1262 (1996).
Tanaka, "Growth Hormone and Bone Disease", *Endocr. J.* 45(Suppl):S47–52 (1998).
Reginster et al., "Promising New Agents in Osteoporosis", *Drugs R.D.* 1(3):195–201 (1999).
Sharara and Giudice, "Role of Growth Hormone in Ovarian Physiiology and Onset of Puberty", *J. Soc. Gynecol. Investig.* 4(1):2–7 (1997).
Artini et al., "Growth hormone cotreatment with gonadotropins in ovulation induction", *J. Endocrinol. Invest.* 19:763–779 (1996).
Homburg, "Growth Hormone and Fertility—Clinical Studies", *Horm. Res.* 45:81–85 (1996).
Homburg and Farhi, "Growth hormone and reproduction", *Curr. Opin. Obstet. Gynecol.* 7:220–223 (1995).
Homburg and Ostergaard, "Clinical applications of growth hormone for ovarian stimulation", *Hum. Reprod. Update* 1(3):264–275 (1995).
Bouillanne et al., "Growth hormone therapy in elderly people: an age–delaying drug?", *Fundam. Clin. Pharmacol.* 10:416–430 (1996).
Rasmussen, "Evaluation of recombinant human growth hormone for wound management", *Dan. Med. Bull.* 42(4):358–370 (1995).

Wennbo and Tornell, "The role of prolactin and growth hormone in breast cancer", *Oncogene* 19:1072–1076 (2000).
Ritzen, et al., "Growth Hormone Treatment of Patients with Prader–Will Syndrome", *J. Pediatr. Endocrinol. Metabol.* 12(Suppl 1):345–349 (1999).
Nagi and Mori, "Prader–Willi syndrome, diabetes mellitus and hypogonadism", *Biomed. Pharmacother.* 53:452–454 (1999).
Chappel, "Growth Hormone in Immune Reconstitution,", *J. Acquir. Immune Def. Sundr. Hum. Retrovirol.* 20(5):423–431 (1999).
Scacchi et al., "Growth hormone in obesity", *Int. J. Obes.* 23:260–271 (1999).
Stanhope et al., "Growth hormone Treatment of Russell–Silver Syndrome", *Horm. Res.* 49(Suppl. 2):37–40 (1998).
Tritos and Mantzoros, "Recombinant Human Growth Hormone: Old and Novel Uses", *Am. J. Med.* 105:44–57 (1998).
Vance, "The Gordon Wilson Lecture—Growth Hormone Replacement In Adults and Other Uses", *Trans. Am. Clin. Climatol. Assoc.* 109:87–96 (1998).
Marcus and Hoffman, "Growth Hormone as Therapy for Older Men and Women", *Annu. Rev. Pharmacol. Toxicol.* 38:45–61 (1998).
de Vos, et al, "Human Growth Hormone and Extracellular Domain of Its Receptor: Crystal Structure of the Complex", *Science* 255:306–312 (1992).
Atwell, et al., "Structural Plasticity in a Remodeled Protein–Protein Interface", *Science* 278:1125–1128 (1997).
Clackson et al., "Structural and Functional Analysis of the 1;1 Growth Hormone:Receptor complex Reveals the Molecular Basis for Receptor Affinity", *J. Mol. Biol.* 277:1111–1128 (1998).
Sundstrom et al., "Crystal Structure of an Antagonist Mutant of Human Growth Hormone, G120R, in Complex with Its Receptor at 2.9 Å Resolution", *J. Biol. Chem.* 271(50):32197–32203 (1996).
Hellinga et al., "Construction of New Ligand Binding Sites in Proteins of Known Structure; I. Computer–aided Modeling of Sites with Pre–defined Geometry", *J. Mol. Biol.* 222:763–785 (1991).
Hurley et al., "Design and Structural Analysis of Alternative Hydrophobic Core Packing Arrangements in Bacteriophage T4 Lysozyme", *J. Mol. Biol.* 224:1143–1154 (1992).
Desjarlais and Handel, "De novo design of the hydrophobic cores of proteins", *Protein Science* 4:2006–2018 (1995).
Harbury et al., "Repacing protein cores with backbone freedom: Structure prediction for coiled coils", *Proc. Natl. Acad. Sci. USA* 92:8408–8412 (1995).
Klemba et al., "Novel metal–binding proteins by design", *Struc. Biol.* 2(5):368–373 (1995).
Nautiyal, et al., "A Designed Heterotrimeric Coiled Coil", *Biochemistry* 34:11645–11651 (1995).
Betz and Grado, "Controlling Topology and Native–like Behavior fo dei Novo–Designed Peptides: Design and Characterization of Antiparallel Four–Stranded Coiled Coils", *Biochemistry* 35:6955–6962 (1996).
Dahiyat and Mayo, "Protein Design automation", *Protein Science* 5:895–903 (1996).
Dahiyat and Mayo, "De Novo Protein Design: Fully Automated Sequence Selection", *Science* 278:82–87 (1997).
Dahayat et al., "De Novo Protein Design: Towards Fully Automated Sequence Selection", *J. Mol. Biol.* 273:789–796 (1997).

Dahiyat et al., "Automated design of the surface positions of protein helices", *Protein Science* 6:1333–1337 (1997).

Jones, "De novo protein design using pairwise potentials and a genetic algorith", *Protein Science* 3:567–574 (1994).

Kono and Doi, "Energy Minimization Method Using Automata Network for Sequence and Side–Chain Conformation Prediction From Given Backbone Geometry", *Proteins: Structure, Function and Genetics* 19:244–255 (1994).

* cited by examiner

1 MATGSRTSLL LAFGLLCLPW LQEGSAFPTI PLSRLFDNAM LRAHRLHQLA
   51 FDTYQEFEEA YIPKEQKYSF LQNPQTSLCF SESIPTPSNR EETQQKSNLE
  101 LLRISLLLIQ SWLEPVQFLR SVFANSLVYG ASDSNVYDLL KDLEEGIQTL
  151 MGRLEDGSPR TGQIFKQTYS KFDTNSHNDD ALLKNYGLLY CFRKDMDKVE
  201 TFLRIVQCRS VEGSCGF

FIG._1A

1 FPTIPLSRLF DNAMLRAHRL HQLAFDTYQE FEEAYIPKEQ KYSFLQNPQT
           HHHHH HHHHHHHHHH HHHHHHHHHH HHHHHHTTHHH HHHHHHTGGG
   51 SLCFSESIPT PSNREETQQK SNLELLRISL LLIQSWLEPV QFLRSVFANS
         T  GGGGS      SHHHHTTS  HHHHHHHHHH HHHHHHTTGG GGGHHHHTT
  101 LVYGASDSNV YDLLKDLEEG IQTLMGRLED GSPRTGQIFK QTYSKFDTNS
         TT   HHHH HHHHHHHHHH HHHHHH     S     SSSSS
  151 HNDDALLKNY GLLYCFRKDM DKVETFLRIV QCRSVEGSCG
         HHHHHH HHHHHHHHHH HHHHHHHHHH HHHHSTTS

FIG._1B

1 cgaaccactc agggtcctgt ggacagctca cctagctgca atggctacag gctcccggac
   61 gtccctgctc ctggcttttg gcctgctctg cctgccctgg cttcaagagg gcagtgcctt
  121 cccaaccatt cccttatcca ggccttttga caacgctatg ctccgcgccc atcgtctgca
  181 ccagctggcc tttgacacct accaggagtt tgaagaagcc tatatcccaa aggaacagaa
  241 gtattcattc ctgcagaacc cccagacctc cctctgtttc tcagagtcta ttccgacacc
  301 ctccaacagg gaggaaacac aacagaaatc aacctagagc tgctccgca tctccctgct
  361 gctcatccag tcgtggctgg agcccgtgca gttcctcagg agtgtcttcg ccaacagcct
  421 ggtgtacggc gcctctgaca gcaacgtcta tgacctccta aaggacctag aggaaggcat
  481 ccaaacgctg atggggaggc tggaagatgg cagccccggg actgggcaga tcttcaagca
  541 gacctacagc aagttcgaca caaactcaca caacgatgac gcactactca gaactacgg
  601 gctgctctac tgcttcagga aggacatgga caaggtcgag acattcctgc gcatcgtgca
  661 gtgccgctct gtggagggca gctgtggctt ctagctgccc gggtggcatc cctgtgaccc
  721 ctccccagtg cctctcctgg ccctggaagt tgccactcca gtgcccacca gccttgtcct
  781 aataaaatta agttgcatc

FIG._1C

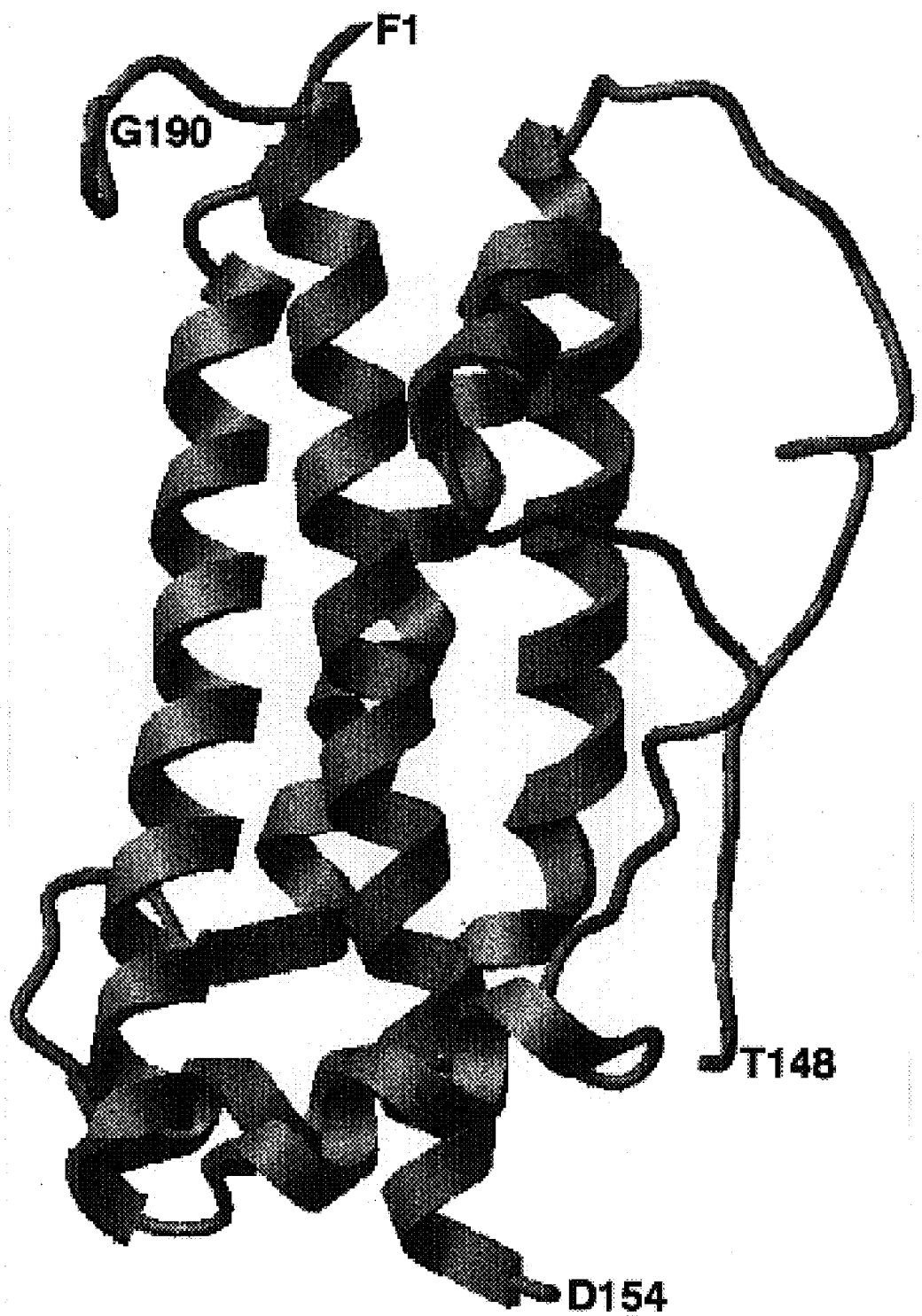
FIG._2 hGH Core

| 6 | 10 | 13 | 17 | 20 | 24 | 27 | 28 | 31 | 36 | 44 | 54 | 55 | 58 | 73 | 75 | 76 | 78 | 79 | 80 |
|---|---|---|---|---|---|---|---|---|---|---|---|---|---|---|---|---|---|---|---|
| Leu | Phe | Ala | Ala | Leu | Ala | Thr | Tyr | Phe | Ile | Phe | Ser | Ile | Leu | Leu | Leu | Leu | Ile | Ser | Leu |

| 81 | 82 | 83 | 85 | 90 | 93 | 96 | 97 | 105 | 110 | 114 | 117 | 121 | 124 | 157 | 161 | 162 | 163 | 166 | 170 |
|---|---|---|---|---|---|---|---|---|---|---|---|---|---|---|---|---|---|---|---|
| Leu | Leu | Ile | Ser | Val | Leu | Val | Phe | Ala | Val | Leu | Ile | Leu | Leu | Leu | Gly | Leu | Leu | Phe | Met |

| 173 | 176 | 177 | 180 | 184 |
|---|---|---|---|---|
| Val | Phe | Leu | Val | Ser |

FIG._3A hGH BOUNDARY1

| 6 | 14 | 26 | 30 | 32 | 34 | 35 | 40 | 50 | 56 | 57 | 59 | 66 | 71 | 74 | 84 | 92 | 107 | 109 | 113 |
|---|---|---|---|---|---|---|---|---|---|---|---|---|---|---|---|---|---|---|---|
| Leu | Met | Asp | Glu | Ala | Tyr | Gln | Ala | Thr | Glu | Ser | Pro | Glu | Ser | Gln | Phe | Asp | Asn | Leu |

| 118 | 125 | 130 | 139 | 143 | 157 | 158 | 183 |
|---|---|---|---|---|---|---|---|
| Glu | Met | Asp | Phe | Tyr | Leu | Lys | Arg |

FIG._3B hGH BOUNDARY2

| 7 | 29 | 43 | 70 | 77 | 87 | 98 | 100 | 102 | 104 | 106 | 111 | 115 | 132 | 137 | 140 | 141 | 142 | 156 | 159 |
|---|---|---|---|---|---|---|---|---|---|---|---|---|---|---|---|---|---|---|---|
| Ser | Gln | Ser | Lys | Arg | Leu | Ala | Ser | Val | Gly | Ser | Tyr | Lys | Ser | Ala | Lys | Ala | Ala | Leu | Asn |

| 161 | 184 | 185 | 188 |
|---|---|---|---|
| Gly | Ser | Val | Ser |

FIG._3C hGH CLUSTERED BOUNDARY

| 7 | 14 | 26 | 29 | 30 | 34 | 40 | 43 | 50 | 57 | 70 | 77 | 84 | 87 | 92 | 98 | 100 | 102 | 104 | 106 |
|---|---|---|---|---|---|---|---|---|---|---|---|---|---|---|---|---|---|---|---|
| Ser | Met | Asp | Gln | Glu | Ala | Gln | Ser | Thr | Ser | Lys | Arg | Gln | Leu | Phe | Ala | Ser | Val | Gly | Ser |

| 109 | 111 | 115 | 118 | 125 | 132 | 135 | 137 | 138 | 140 | 141 | 142 | 143 | 144 | 145 | 147 | 156 | 159 | 161 | 184 |
|---|---|---|---|---|---|---|---|---|---|---|---|---|---|---|---|---|---|---|---|
| Asn | Tyr | Lys | Glu | Met | Ser | Thr | Ser | Ile | Lys | Gln | Thr | Tyr | Ser | Lys | Asp | Leu | Asn | Gly | Ser |

| 185 | 188 |
|---|---|
| Val | Ser |

FIG._3D

```
Res  Cons
Num  Seq   Other Mutations
^^^  ^^^^^ ^^^^^^^^^^^^^^
  6  L:959 M: 40 V:  1
 10  F:1000
 13  V:943 I: 57
 17  A:997 M:  3
 20  L:934 M: 66
 24  A:1000
 27  V:1000
 28  F:996 L:  2 Y:  2
 31  F:905 W: 38 I: 26 M: 17 L:  5 Y:  5 V:  4
 36  I:715 L:258 V: 27
 44  F:1000
 54  Y:928 F: 72
 55  A:1000
 58  I:782 V:211 L:  7
 73  L:924 M: 52 A: 24
 75  L:983 M: 17
 76  L:984 M: 16
 78  I:865 F: 53 M: 39 V: 30 L: 13
 79  A:886 V:114
 80  L:1000
 81  L:994 I:  6
 82  L:788 I:195 M: 10 V:  7
 83  I:964 L: 28 V:  8
 85  A:1000
 90  I:702 V:294 M:  4
 93  L:1000
 96  V:1000
 97  F:998 L:  2
105  A:1000
110  V:967 M: 16 L: 13 I:  4
114  M:760 L:173 F: 67
117  L:983 M: 14 A:  3
121  I:970 V: 14 M: 12 L:  4
124  L:1000
157  L:1000
161  M:902 L: 75 F: 23
162  L:856 V: 86 I: 50 M:  8
163  L:889 M:111
166  M:449 L:316 F:235
170  M:457 F:301 L:242
173  V:999 I:  1
176  F:993 Y:  7
177  L:873 I:127
180  V:1000
184  A:1000
```

FIG._4A

```
  1 FPTIPLSRLF DNVMLRAHRL HQLAFDVFQE FEEAYIPKEQ KYSFLQNPQT
 51 SLCYAESIPT PSNREETQQK SNLELLRIAL LLIQAWLEPI QFLRSVFANS
101 LVYGASDSNV YDLMKDLEEG IQTLMGRLED GSPRTGQIFK QTYSKFDTNS
151 HNDDALLKNY MLLYCFRKDM DKVETFLRIV QCRAVEGSCG F
```

FIG._4B

```
  1 FPTIPLSRLF DNVMLRAHRL HQLAFDVYQE FEEAYIPKEQ KYSFLQNPQT
 51 SLCFSESIPT PSNREETQQK SNLELLRIAL LLIQSWLEPI QFLRSVFANS
101 LVYGASDSNV YDLLKDLEEG IQTLMGRLED GSPRTGQIFK QTYSKFDTNS
151 HNDDALLKNY MLLYCFRKDM DKVETFLRIV QCRAVEGSCG F
```

FIG._4C

```
  1 FPTIPLSRLF DNVMLRAHRL HQLAFDVYQE FEEAYIPKEQ KYSFLQNPQT
 51 SLCFAESIPT PSNREETQQK SNLELLRIAL LLIQAWLEPI QFLRSVFANS
101 LVYGASDSNV YDLLKDLEEG IQTLMGRLED GSPRTGQIFK QTYSKFDTNS
151 HNDDALLKNY MLLYCFRKDM DKVETFLRIV QCRAVEGSCG F
```

FIG._4D

```
  1 FPTIPLSRLF DNVMLRAHRL HQLAFDVFQE FEEAYIPKEQ KYSFLQNPQT
 51 SLCYAESIPT PSNREETQQK SNLELLRIAL LLIQAWLEPI QFLRSVFANS
101 LVYGASDSNV YDLLKDLEEG IQTLMGRLED GSPRTGQIFK QTYSKFDTNS
151 HNDDALLKNY MLLYCFRKDM DKVETFLRIV QCRAVEGSCG F
```

FIG._4E

```
Res  Cons
Num  Seq   Other Mutations
^^^  ^^^^^ ^^^^^^^^^^^^^^^
  6  L:954 I: 23  E: 23
 14  L:945 I: 29  M: 26
 26  R:447 A:445  K: 95  L:  6  M:  5  D:  2
 30  W:945 F: 54  V:  1
 32  E:1000
 34  K:855 H:144  W:  1
 35  E:889 D:110  Y:  1
 40  K:914 V: 46  R: 34  Y:  2  I:  2  L:  1  M:  1
 50  F:994 L:  6
 56  E:999 F:  1
 57  K:674 R:197  I: 46  H: 41  V: 21  F:  7  Y:  5  A:  3  L:  3  Q:  3
 59  E:994 V:  6
 66  E:1000
 71  H:637 E:363
 74  E:637 F:275  W: 88
 84  R:944 I: 56
 92  R:752 K: 91  H: 56  E: 54  Y: 33  F: 10  V:  3  L:  1
107  D:954 A: 33  V: 12  E:  1
109  F:451 R:336  L:181  I: 12  V: 11  K:  5  M:  4
113  L:621 F:379
118  L:1000
125  I:503 M:494  V:  3
130  R:691 V:184  H: 60  H: 57  A:  8
139  H:953 A: 25  H: 21  E:  1
143  D:944 A: 56
157  L:907 R: 51  M: 35  V:  6  H:  1
158  F:912 K: 54  E: 28  L:  3  V:  3
183  H:871 K:111  F: 17  I:  1
```

FIG._5A

```
  1 FPTIPLSRLF DNALLRAHRL HQLAFATYQV FEEWYIPKEK KYSFLQNPQF
 51 SLCFSEEIVT PSNREETQQK HNLELLRISL LLIRSWLEPV QELRSVFANS
101 LVYGASASFV YDLLKDLLEG IQTLIGRLER GSPRTGQIHK QTDSKFDTNS
151 HNDDALLKNY GLLYCFRKDM DKVETFLRIV QCHSVEGSCG F
```

FIG._5B

```
  1 FPTIPLSRLF DNALLRAHRL HQLAFATYQW FEEKEIPKEK KYSFLQNPQF
 51 SLCFSEKIET PSNREETQQK HNLELLRISL LLIRSWLEPV QRLRSVFANS
101 LVYGASDSFV YDLLKDLLEG IQTLIGRLER GSPRTGQIHK QTDSKFDTNS
151 HNDDALLFNY GLLYCFRKDM DKVETFLRIV QCHSVEGSCG F
```

FIG._5C

```
Res  Cons
Num  Seq  Other Mutations
^^^  ^^^^^ ^^^^^^^^^^^^^^^
  7  K:873 Y: 43  R: 26  F: 22  L: 18  V: 18
 29  K:922 I: 31  R: 25  V: 22
 43  K:594 R:336  W: 31  I: 16  V: 11  H:  7  M:  2  L:  2  F:  1
 70  K:897 L: 52  M: 34  R: 17
 77  M:914 L: 81  V:  5
 87  L:500 I:381  M: 97  V: 21  Y:  1
 98  V:931 M: 32  A: 26  K: 11
100  A:1000
102  V:649 I:351
104  G:1000
106  K:909 A: 39  R: 24  H: 19  M:  7  L:  2
111  R:922 K: 78
115  K:978 R: 18  H:  4
132  A:1000
137  W:998 R:  1  A:  1
140  K:1000
141  K:825 F:175
142  V:1000
156  L:421 M:183  I:175  V:139  W: 37  K: 25  R:  8  T:  6  Y:  5  A:  1
159  F:929 M: 35  I: 23  W: 13
161  M:893 L: 85  F: 22
184  A:1000
185  V:999 I:  1
188  A:1000
```

FIG._6A

```
  1 FPTIPLKRLF DNAMLRAHRL HQLAFDTYKE FEEAYIPKEQ KYKFLQNPQT

51 SLCFSESIPT PSNREETQQK SNLELLMISL LLIQSWLEPV QFLRSVFVNA

101 LVYGAKDSNV RDLLKDLEEG IQTLMGRLED GAPRTGWIFK KVYSKFDTNS

151 HNDDALLKFY MLLYCFRKDM DKVETFLRIV QCRAVEGACG F
```

FIG._6B

```
Res  Cons
Num  Seq  Other Mutations
^^^  ^^^^ ^^^^^^^^^^^^^^
  7  S:1000
 14  M:1000
 26  K:826 L: 71 R: 51 M: 49 A:  3
 29  I:657 V:331 L:  6 K:  6
 30  V:744 I:118 K:107 L: 17 W: 11 R:  3
 34  W:866 F:109 L: 11 K: 10 A:  4
 40  V:438 W:189 I:141 R:101 K: 74 L: 24 Y: 23 M:  6 H:  4
 43  W:401 K:389 R:192 F: 10 H:  6 I:  1 M:  1
 50  F:950 M: 50
 57  S:1000
 70  K:1000
 77  M:1000
 84  M:930 W: 66 V:  4
 87  L:1000
 92  V:887 Y: 49 F: 30 R: 25 A:  5 K:  3 L:  1
 98  A:1000
100  A:1000
102  I:962 V: 38
104  G:1000
106  S:1000
109  I:317 V:306 F:280 M: 27 W: 18 L: 17 Y: 13 A: 12 K:  9 R:  1
111  R:983 K: 17
115  K:1000
118  M:888 F: 63 K: 45 L:  4
125  I:978 V: 22
132  A:1000
135  T:1000
137  R:977 F:  8 H:  8 Y:  7
138  I:1000
140  K:1000
141  F:1000
142  V:910 K: 52 Y: 24 R: 14
143  V:927 A: 73
144  S:1000
145  A:1000
147  D:1000
156  L:1000
159  N:1000
161  G:1000
184  S:1000
185  V:1000
188  S:1000
```

FIG._7A

```
  1 FPTIPLSRLF DNAMLRAHRL HQLAFKTYIV FEEWYIPKEV KYKFLQNPQF
 51 SLCFSESIPT PSNREETQQK SNLELLMISL LLIMSWLEPV QVLRSVFANA
101 LIYGASDSFV RDLLKDLMEG IQTLIGRLED GAPRTGRIFK FVVSAFDTNS
151 HNDDALLKNY GLLYCFRKDM DKVETFLRIV QCRSVEGSCG
```

FIG._7B

1   FPTIPLSRLF  DNAMLRAHRL  HQLAF<u>K</u>TY<u>IV</u>  FEE<u>WY</u>IPKE<u>W</u>  KY<u>W</u>FLQNPQ<u>F</u>
51  SLCFSESIPT  PSNREETQQK  SNLELL<u>M</u>ISL  LL<u>IM</u>SWLEPV   Q<u>V</u>LRSVFAN<u>A</u>
101 L<u>I</u>YGASDS<u>F</u>V  <u>R</u>DLLKDL<u>M</u>EG  IQTL<u>I</u>GRLED  G<u>A</u>P<u>RA</u>G<u>RA</u>FK  <u>FVVAAFA</u>TNS
151 HNDDALLKNY  GLLYCFRKDM  DKVETFLRIV  QCRSVEGSCG

FIG._7C

1   FPTIPLSRLF  DNAMLRAHRL  HQLAF<u>K</u>TY<u>IV</u>  FEE<u>W</u>YIPKE<u>V</u>   KY<u>K</u>FLQNPQ<u>F</u>
51  SLCFSESIPT  PSNREETQQK  SNLELL<u>M</u>ISL  LL<u>IM</u>SWLEPV   Q<u>V</u>LRSVFAN<u>A</u>
101 L<u>I</u>YGASDS<u>F</u>V  <u>R</u>DLLKDL<u>M</u>EG  IQTL<u>I</u>GRLED  G<u>A</u>P<u>RA</u>G<u>RA</u>FK  <u>FVVAAFA</u>TNS
151 HNDDALLKNY  GLLYCFRKDM  DKVETFLRIV  QCRSVEGSCG

FIG._7D

1   FPTIPLSRLF  DNAMLRAHRL  HQLAF<u>ET</u>Y<u>KV</u>  FEE<u>W</u>YIPKE<u>V</u>   KY<u>K</u>FLQNPQ<u>F</u>
51  SLCFSESIPT  PSNREETQQK  SNLELL<u>M</u>ISL  LL<u>IM</u>SWLEPV   Q<u>V</u>LRSVFAN<u>A</u>
101 LVYGASDS<u>F</u>V  <u>R</u>DLLKDL<u>K</u>EG  IQTL<u>I</u>GRLED  G<u>A</u>P<u>RA</u>G<u>RA</u>FK  <u>FVVAAFA</u>TNS
151 HNDDALLK<u>N</u>Y  GLLYCFRKDM  DKVETFLRIV  QCRSVEGSCG

FIG._7E

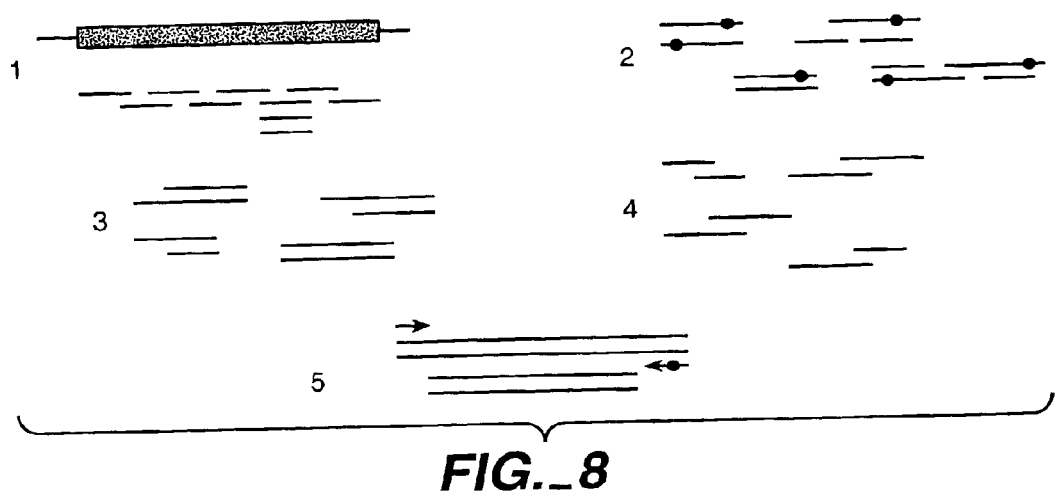
FIG._8
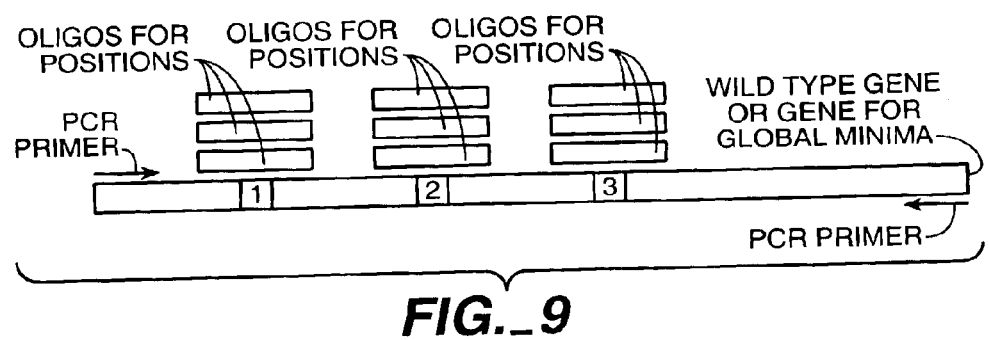
FIG._9

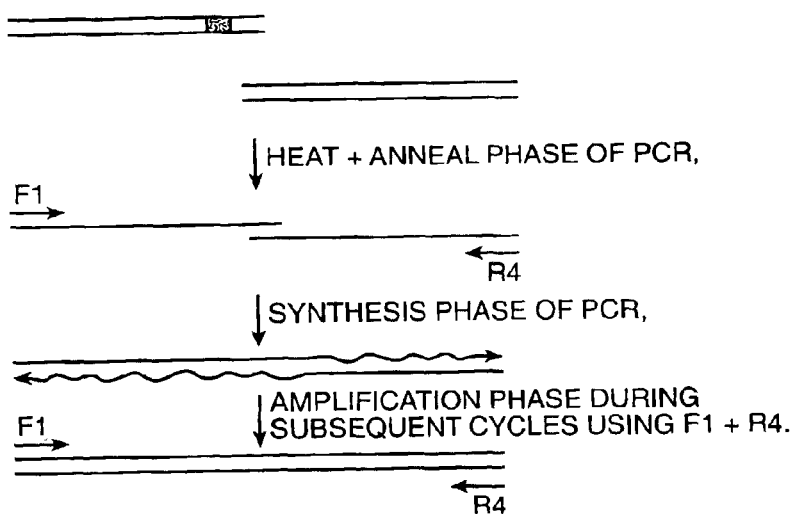
FIG._10

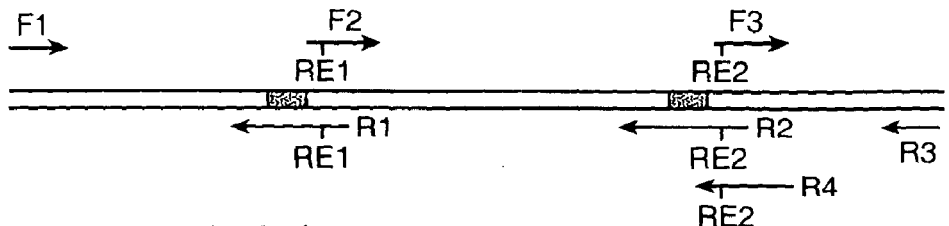

STEP 1: SET UP 3 PCR REACTIONS:

TUBE 1:

TUBE 2:
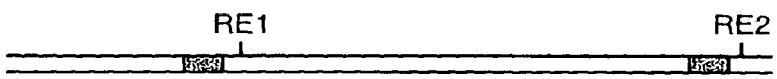

TUBE 3:

STEP 2: DIGEST PRODUCTS FROM STEP 1 WITH SUITABLE RESTRICTION ENDONUCLEASES.

STEP 3: LIGATE DIGESTED PRODUCT FROM STEP 2, TUBE 2 WITH DIGESTED PRODUCT FROM STEP 2, TUBE 1.

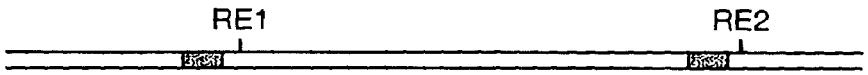

STEP 4: AMPLIFY VIA PCR LIGATED PRODUCTS OF STEP 3 WITH F1 + R4.

STEP 5: DIGEST AMPLIFIED PRODUCT OF STEP 4 WITH RESTRICTION ENDONUCLEASE #2.

STEP 6: LIGATE PRODUCT FROM STEP 5 WITH PRODUCT FROM STEP 2, TUBE 3.

STEP 7: AMPLIFY PRODUCT FROM STEP 6 WITH F1 + R3.

FIG. 11

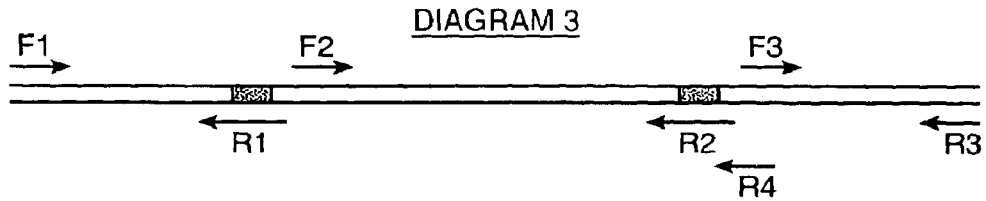
FIG._12
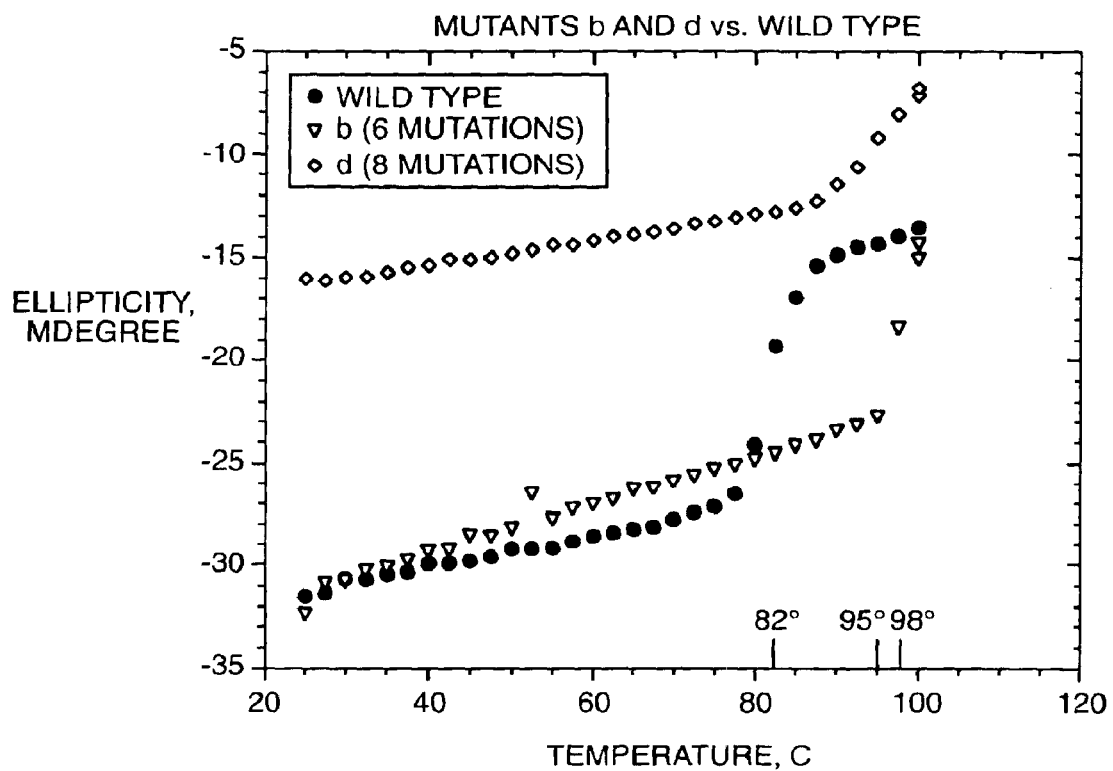
FIG._13

NUCLEIC ACIDS AND PROTEINS WITH GROWTH HORMONE ACTIVITY

This application is a continuing application of U.S. Ser. No. 60/133,784, filed May 12, 1999.

FIELD OF THE INVENTION

The invention relates to novel growth hormone activity (GHA) proteins and nucleic acids. The invention further relates to the use of the GHA proteins in the treatment of growth hormone (hGH) related disorders.

BACKGROUND OF THE INVENTION

Human growth hormone (hGH), also known as somatotropin, is a single chain polypeptide hormone of 191 amino acids (molecular weight of app. 22 kD) that is synthesized in the somatotropic cells of the anterior pituitary and plays an important role in somatic growth through its effects on the metabolism of proteins, carbohydrates, and lipids. hGH is a member of a family of homologous hormones that also includes placental lactogens and prolactins [Nicoll et al., Endocr. Rev. 7(2):169–203 (1986)]. Several distinct biological activities have been ascribed to hGH, including effects on (i) linear growth (somatogenesis), (ii) lactation, (iii) activation of macrophages, and (iv) insulin-like and diabetogenic effects [Chawla et al., Annu. Rev. Med. 34:519–47 (1983); Edwards et al., Science 239(4841 Pt1):769–71 (1988); Thorner and Vance, J. Clin. Invest. 82(3):745–7 (1988)]. These biological effects derive from the interaction between hGH and specific cellular receptors, such as the growth hormone receptor [Leung et al., Nature 330 (6148):537–43 (1987)] or the prolactin receptor [Boutin et al., Cell 53(1):69–77 (1988)].

The binding of a single growth hormone (GH) molecule to a pair of GH receptors (GHR) induces receptor dimerization, promotes the rapid association of GHR with the tyrosine kinase JAK2 and activates a phosphorylation cascade involving the initial activation of the receptor-associated kinase JAK2. This results in the tyrosyl phosphorylation of the kinase itself and of the cytoplasmic domain of the receptor. The phosphorylated tyrosine residues act as docking sites for various signaling molecules that contain Src homology 2 (SH-2) or other phosphorysyl-binding domains. Among these are the STAT proteins 1, 3 and 5 (signal transducers and activators of transcription), the insulin receptor substrates (IRS) 1 and 2, which are believed to mediate some of the metabolic effects of GH and the adaptor protein Shc, leading to the activation of the Ras/MAP kinase pathway, the second messengers such as diacylglycerol, calcium, and nitic oxide. Ultimately, these pathways modulate cellular functions such as gene transcription, metabolite transport, and enzymatic activities that affect gH-dependent control of growth and metabolism. Activation by GH is very transient and several mechanisms are involved in this downregulation: internalization and degradation of the receptor and recruitment of phosphatases or of specific inhibitors of the JAK/Stat pathway, the SOCS proteins [for review, see Finidori, Vitam. Horm. 59:71–97 (2000); Carter-Su et al., Endocr. J. 43 Suppl:S65–70 (1996); Cambell, J. Pediatr. 131 (1 Pt2):S42–4 (1997)].

GH can be isolated from human pituitary glands or can be prepared recombinantly. There are two commercially available forms of the genetically engineered hormone, one of which is identical in amino acid sequence to the naturally occurring human growth hormone. The other form, isolated from a prokaryotic cell, has an additional methionine residue at the N-terminus of the protein. Recombinant forms of hGH have been available since 1993 for the long term treatment of children who have growth failure due to lack of adequate endogenous growth hormone secretion. The product is currently administered by either intramuscular or subcutaneous injection and stored in the refrigerator at 2–8° C.

GH has been either reported to have a role in, or suggested for therapy in or has shown efficacy in the treatment of (i) hypochondroplasia and idiopathic short stature [Ramaswami et al., Acta Paediatr. Suppl. 88(428):116–7 (1999); Kamp and Wit, Horm. Res. 49 Suppl. 2:67–72 (1998)]; (ii) girls with Turner syndrome [de Muinck Keizer-Schrama and Sas, Acta Paediatr. Suppl. 88)433): 126–9 (1999); Haeusler, Horm. Res. 49 Suppl. 2:62–6 (1998)]; (iii) growth delay in burned children [Low et al., Lancet 354(9192):1789 (1999); Hemdon et al., Horm. Res. 45 Suppl. 1:29–31 (1996)]; (iv) GH replacement in GH deficient adults [Bengtsson et al., J. Clin. Endocrinol. Metab. 85(3):933–42 (2000); Cook et al., Adv. Intern. med. 45:297–315 (2000); Welle, Curr. Opin. Clin. Nutr. Metab. Care 1(3):257–62 (1998); Abs et al., Clin. Endocrinol (Oxf) 50(6):703–13 (1999); Clark and Kendall, J. Clin. Pharm. Ther. 21(6):367–72 (1996)]; (v) muscle wasting under conditions, including surgical stress, renal failure, muscular dystrophy, glucocorticoid administration and HIV infection [Welle, supra; Windisch et al., Ann. Pharmacother. 32(4):437–45 (1998); Mentser et al., J. Pediatr. 131(1 Pt 2):S20–4 (1997); Hirschfeld, Horm. Res. 46(4–5):215–21 (1996)]; (vi) congestive heart failure and cardiovascular drug therapy [Cittadini et al., Miner. Electrolyte Metab. 25(102):51–5 (1999); Johnson and Gheorghiade, Am Heart J. 137(6):989–91 (1999); Sacca, Baillieres Clin. Endocrinol. Metab. 12(2):217–31; Gomberg-Maitland and Frishman, Am: Heart J. 132(6):1244–62 (1996)]; (vii) bone diseases and osteoporosis [Tanaka, Endocr. 45 Suppl:S47–52 (1998); Reginster et al., Drugs R. D. 1(3):195–201 (1999)]; (viii) puberty and reproduction [Sharara and Giudice, J. Soc, Gynecol. Investig. 4(1):2–7 (1997); Artini et al., J. Endocrinol. Invest. 19(11):763–79 (1996); Homburg, Horm. Res. 45(1–2):81–5 (1996); Homburg and Farhi, Curr. Opin. Obstet Gynecol. 7(3):220–3 (1995); Homburg and Ostergaard, Hum. Reprod. Update 1(3):264–75 (1995)]; (ix) GH therapy in elderly people [Bouillanne et al., Fundam. Clin. Pharmacol. 10(5): 416–30 (1996)]; (x) wound management [Rasmussen, Dan. Med. Bull. 42(4):358–70 91995)]; (xi) breast cancer [Wennbo and Tomell, Oncogene 19(8):1072–6 (2000)]; (xii) Prader-Willi syndrome [Ritzen et al., J. Pediatr. Endocrinol. Metabol. 12 Suppl. 1:345–9 (1999); Nagai and Mori, Biomed. pharmacother. 53(10):452–4 (1999)]; (xiii) immune reconstitution [Chappel, J. Acquir. Immune Defic. Sundr. Hum. Retrovirol. 20(5):423–31 (1999)]; (xiv) obesity [Scacchi et al., Int. J. Obes. relat. Metab. disord. 23(3): 260–71 (1999)]; and (xv) Russell-Silver syndrome [Stanhope et al., Horm. Res. 49 Suppl. 2:37–40 (1998)]. For further reviews on GH therapies, see Tritos and Mantzoros, Am. J. Med. 105(1):44–57 (1998); Vance, Trans. Am. Clin. Climatol. Assoc. 109:87–96 (1998); Marcus and Hoffman, Annu. Rev. Pharmacol. Toxicol. 38:45–61 (1998).

hGH is marketed under the names NUTROPIN™ or PROTROPINT™ (Genentech, Inc.), NORDOTROPIN™ (Novo Nordisk), GENOTROPIN™ (Pharmacia Upjohn), HUMATROPE™ (Eli Lilly) and SAIZEN™ or SEROSTIM™ (Serono). FDA approval is fortreatment of GH deficiency and Turner's syndrome.

To this end, variants of hGH sequences, applications and production procedures are known; see for example U.S. Pat. Nos. 4,658,021, 4,665,160, 5,068,317, 5,079,345, 5, 424, 199, 5,534,617, 5,597,709, 5,612,315, 5,633,352, 5,635,604, 5,688,666 and references cited therein.

Recently, the crystal structures of wild type hGH in a 1:2 complex with its receptor was solved at 2.8 Å resolution (de Vos et al., Science 255(5042):306–12 (1992); hereby expressly incorporated by reference. The structure of this complex is deposited as 3HHR entry in the Brookhaven Protein Data Bank (PDB). The crystal structure confirmed that the complex consists of one molecule of growth hormone per two molecules of receptor. The hormone is a four-helix bundle motif characterized by the first two helices running parallel to each other but antiparallel to the last two. In addition to the structure of the wild type hGH (3HHR and 1HGU entries in the PDB), there are five crystal structures of mutant forms of hGH available in the literature and the PDB: 1HUW, 1AX1, 1A22, 1HWH, and 1HWG, hereby expressly incorporated by reference.

1HUW. PDB entry 1huw [Ultsch et al., Science 236(1): 286–299 (1994)] contains a structure (2.0 Å resolution) of a variant hGH, in which 15 mutations (F10A, M14W, H18D, H21N, K41I, Y42H, L45W, Q46W, F54P, R64K, R167N, D171S, E174S, F176Y, AND I179) were introduced with phage display mutagenesis to improve receptor binding affinity by 400-fold.

1AX1. PDB entry 1axi [Atwell et al., Science 278:1125–1128(1997)] contains a structure of a complex of a mutant of hGH (G120R, K168R, D171T, K172Y, E174A, and F176Y) with its receptor mutated at position 104: W104A. The resolution is 2.1 Å.

1A22. The PDB entry 1a22 [Clackson et al., J. Mol. Biol. 277:1111–1128 (1998)] is a structure of the 1:1 G120R growth hormone mutantreceptor complex at 2.6 Å resolution. The designed G120R mutant is an antagonist and can bind only one molecule of the GHR. 1HWH. The PDB entry 1 hwh [Sundstrom et al., J. Biol. Chem. 271(50):32197–203 (1996)] is a crystal structure of a growth hormone antagonist mutant G120R with its receptor as a 1:1 complex at 2.9 Å resolution. The 1:1 complex is remarkably similar to the native growth hormone receptor 1:2 complex. A comparison between the two structures reveals only minimal differences in the conformations of the hormone or its receptor in the two complexes, including the angle between the two immunogl;obulin-like domains of the receptor.

1 HWG. The PDB entry 1hwg (Sundstrom et al., supra) contains a crystal structure of an antagonist mutant G120R of human growth hormone in 1:2 complex with its receptor at 2.5 Å resolution. important difference between this structure and the previously published crystal structure at 2.8 Å resolution (3HHR) is revealed. Trp-104 in the receptor, a key residue in the hormone-receptor interaction has an altered conformation in the low affinity site enabling a favorable hydrogen bond to be formed with Asp-116 of the hormone.

The available crystal structure of hGH allows further protein design and the generation of more stable proteins or protein variants with an altered activity. Several groups have applied and experimentally tested systematic, quantitative methods to protein design with the goal of developing general design algorithms (Hellinga et al., J. Mol. Biol. 222: 763–785 (1991); Hurley et al., J. Mol. Biol. 224:1143–1154 (1992); Desjarlaisl et al., Protein Science 4:2006–2018 (1995); Harbury et al., Proc. Natl. Acad. Sci. U.S.A. 92:8408–8412 (1995); Klemba et al., Nat. Struc. Biol. 2:368–373 (1995); Nautiyal et al., Biochemistry 34:11645–11651 (1995); Betzo et al., Biochemistry 35:6955–6962 (1996); Dahiyat et al., Protein Science 5:895–903 (1996); Dahiyat et al., Science 278:82–87 (1997); Dahiyat et al., J. Mol. Biol. 273:789–96; Dahiyat et al., Protein Sci. 6:1333–1337 (1997); Jones, Protein Science 3:567–574 (1994); Konoi, et al., Proteins: Structure, Function and Genetics 19:244–255 (1994)). These algorithms consider the spatial positioning and steric complementarity of side chains by explicitly modeling the atoms of sequences under consideration. In particular, WO98147089, and U.S. Ser. No. 09/127,926 describe a system for protein design, both are expressly incorporated by reference.

A need still exists for proteins exhibiting both significant stability and growth hormone activity. Achievement of better stability will improve the convenience for shipment, storage and patient use of this product. Accordingly, it is an object of the invention to provide growth hormone activity (GHA) proteins with a higher thermostability than the naturally occurring hormone, nucleic acids and antibodies for the treatment of hGH related disorders.

SUMMARY OF THE INVENTION

In accordance with the objects outlined above, the present invention provides non-naturally occurring growth hormone activity (GHA) proteins (e.g. the proteins are not found in nature) comprising amino acid sequences that are less than about 97% identical to human growth hormone (hGH). The GHA proteins have at least one altered biological property of hGH protein; for example, some GHA proteins will be more stable than hGH and bind to a cell comprising a growth hormone receptor (GHR) or prolactin receptor. Thus the invention provides GHA with amino acid sequences that have at least about 5 amino acid substitutions as compared to the hGH sequence shown in FIG. 1A (SEQ ID NO:1).

In a further aspect, the present invention provides non-naturally occurring HGA conformers that have three dimensional backbone structures that substantially correspond to the three dimensional backbone structure of hGH. The amino acid sequence of the GHA conformer and the amino acid sequence of hGH are less than about 97% identical. In one aspect at least about 90% of the non-identical amino acids are in a core region of the conformer. In other aspects, the conformer have at least about 100% of the non-identical amino acids are in a core region of the conformer.

In an additional aspect, the changes are selected from the amino acid residues at positions selected from positions 6, 7, 13, 14, 17, 20, 26, 27, 28, 29, 30, 31, 34, 35, 36, 40, 43, 50, 54, 55, 56, 57, 58, 59, 70, 71, 73, 74, 75, 76, 77, 78, 79, 81, 82, 83, 84, 85, 87, 90, 92, 97, 98, 100, 102, 106, 107, 109, 110, 111, 113, 114, 115, 117, 118, 121, 125, 130, 132, 137, 139, 141, 142, 143, 145, 156, 157, 158, 159, 161, 162, 163, 166, 170, 173, 176, 177, 183, 184, 185, and 188. In a preferred aspect, the changes are selected from the amino acid residues at positions selected from positions 13, 27, 28, 54, 55, 79, 85, 90, 114, 161, or 184. In one aspect, the changes are selected from the amino acid residues at positions selected from positions 14, 26, 30, 34, 35, 40, 50, 57, 59, 71, 84, 92, 107, 109, 118, 125, 130, 139, 143, 158, or 183. In another aspect, the changes are selected from the amino acid residues at positions selected from positions 7, 29, 43, 77, 98, 100, 106, 111, 132, 137, 141, 142, 159, 161, 184, or 188. In another aspect, the changes are selected from the amino acid residues at positions selected from positions 26, 29, 30, 34, 40, 43, 50, 77, 84, 92, 100, 102, 109, 111, 118, 125, 132, 135, 137, 138, 141, 142, 143, 144, 145, or 147. Preferred embodiments include at least about 5 variations.

In a further aspect, the invention provides recombinant nucleic acids encoding the non-naturally occurring GHA proteins, expression vectors comprising the recombinant nucleic acids, and host cells comprising the recombinant nucleic acids and expression vectors.

In an additional aspect, the invention provides methods of producing the GHA proteins of the invention comprising culturing host cells comprising the recombinant nucleic acids under conditions suitable for expression of the nucleic acids. The proteins may optionally be recovered. In a further aspect, the invention provides pharmaceutical compositions comprising an GHA protein of the invention and a pharmaceutical carrier.

In an additional aspect, the invention provides methods for treating a GH responsive condition comprising administering a GHA protein of the invention to a patient. The GH condition may be hypochondroplasia or idiopathic short structure; Turner's syndrome; growth delay in burned children; muscle wasting under conditions, including, but not limited to surgical stress, renal failure, muscular dystrophy, glucocorticoid administration or HIV infection; congestive heart failure or cardiovascular drug therapy; bone diseases or osteoporosis; disorders affecting puberty or reproduction; diffuse gastric bleeding; disorders relating to general anabolism, including, but not limited to pseudoarthrosis, burn therapy, old age cachetic states; breast cancer; Prader-Willi syndrome; obesity; and Russell-Silver syndrome.

In an additional aspect, the invention provides GHA proteins for use in GH replacement therapies in GH deficient adults; GH therapy in elderly people; wound healing, including but not limited to stasis ulcers, decubitus ulcers, or diabetic ulcers; post-surgical (trauma) healing process; total parenteral nutrition (TPN); and the reconstitution of the immune system.

BRIEF DESCRIPTION OF THE DRAWINGS

FIG. 1A (SEQ ID NO:1) depicts the amino acid sequence of the human hGH as deposited at SWISS-PROT #P01241, somatotropin precursor. Amino acid residues 1–26 correspond to the signal peptide and amino acid residues 27–217 correspond to the mature protein.

FIG. 1B (SEQ ID NO:14) depicts the amino acid sequence of hGH as used in the determination of the crystal structure of hGH with its receptor [PDB and GenBank # 3HHR; de Vos et al., Science 255(5042):306–12 (1992)] and secondary structure elements. Secondary structure element legend: H, alpha helix (4-helix); B, residue in isolated beta bridge; E, extended strand, participates in beta ladder; G, 310 helix (3-helix); I, pi helix (5-helix); T, hydrogen bonded turn; S, bend. Amino acid residues 1 to 190 of FIG. 1B (SEQ ID NO:14) correspond to amino acid residues 27–216 of the amino acid sequence depicted in FIG. 1A (SEQ ID NO:1). The amino acid numbers shown were used as the amino acid numbers in GHA proteins that also include F191.

FIG. 1C (SEQ ID NO:2) depicts the complete DNA sequence encoding wild type human growth hormone (Roskam and Rougeon, Nucleic Acids Res. 7(2):305–20 (1979); Martial et al., Science 205(4406):602–7 (1979); GenBank accession number V00519; similar sequences are deposited under #A12770, M13438, and J03071). The encoded sequence consists of the signaling sequence, MATGSRTSLLLAFGLLCLPWLQEGSA (residues -26 to -1 of SEQ ID NO:1), and the 191 amino acids that constitute the actual protein (see FIGS. 1A and 1B)(SEQ ID NO:1). The DNA sequence of 799 nucleotides includes the coding sequence (bases 41 to 694) and untranslated sequences.

FIG. 2 depicts the structure of wild type hGH as taken from the PDB entry 3HHR.

FIG. 3A depicts the CORE residues (SEQ ID NO:14). FIG. 3B depicts the BOUNDARY1 residues (SEQ ID NO:14). FIG. 3C depicts the BOUNDARY2 residues (SEQ ID NO:14). FIG. 3D depicts the CLUSTERED BOUNDARY residues (SEQ ID NO:14). These are selected for PDA. The individual sets are described in detail herein.

FIG. 4A depicts the mutation pattern of the CORE sequences of hGH based on the analysis of the lowest 1000 protein sequences generated by Monte Carlo analysis the CORE sequence (only the amino acid residues of positions 6, 10, 13, 17, 20, 24, 27, 28, 31, 36, 44, 54, 55, 58, 73, 75, 76, 78, 79, 80, 81, 82, 83, 85, 90, 93, 96, 97, 105, 110, 114, 117, 121, 124, 157, 161, 162, 163, 166, 170, 173, 176, 177, 180, and 184 are given). The numbers following each amino acid indicate how often within the 1000 sequences analyzed, the indicated amino acid residue was found. For example, at position 13, the hGH amino acid is alanine (see FIG. 1A) (SEQ ID NO:1); in GHA proteins, 943 of the top 1000 sequences had valine at this position, and 57 of the sequences had isoleucine. None of the sequences had alanine at this position. Similarly, for position 90 (valine in hGH), isoleucine (702) is preferred over valine (294).

FIGS. 4B to 4E (SEQ ID NO:3–6) depict preferred GHA protein sequences based on the PDA analysis the hGH CORE sequence. Amino acid residues different from the hGH (see FIG. 1B)(SEQ ID NO:14) are underlined and shown in bold.

FIG. 5A depicts the mutation pattern of the BOUNDARY1 sequences of hGH based on the analysis of the lowest 1000 protein sequences generated by Monte Carlo analysis the BOUNDARY1 sequence (only the amino acid residues of positions 6, 14, 26, 30, 32, 34, 35, 40, 50, 56, 57, 59, 66, 71, 74, 84, 92, 107, 109, 113, 118, 125, 130, 139, 143, 157, 158, and 183 are given). The numbers following each amino acid indicate how often within the 1000 sequences analyzed, the indicated amino acid residue was found. For example, at position 118, the hGH amino acid is glutamic acid (see FIG. 1B)(SEQ ID NO:14); in GHA proteins, all 1000 sequences had leucine at this position. Similarly, for position 14 (methionine in hGH), leucine (945) is preferred over methionine (26).

FIGS. 5B and 5C (SEQ ID NOS:7–8)depict preferred GHA protein sequences based on the PDA analysis the hGH BOUNDARY1 sequence. Amino acid residues different from the hGH (see FIG. 1B)(SEQ ID NO:14) are underlined and shown in bold.

FIG. 6A depicts the mutation pattern of the BOUNDARY2 sequences of hGH based on the analysis of the lowest 1000 protein sequences generated by Monte Carlo analysis the BOUNDARY2 sequence (only the amino acid residues of positions 7, 29, 43, 70, 77, 87, 98, 100, 102, 104, 106, 111, 115, 132, 137, 140, 141, 142, 156, 159, 161, 184, 185, and 188 are given). The numbers following each amino acid indicate how often within the 1000 sequences analyzed, the indicated amino acid residue was found. For example, at position 142, the hGH amino acid is threonine (see FIG. 1B) (SEQ ID NO:14); in GHA proteins, all 1000 sequences had valine at this position. Similarly, for position 7 (serine in hGH), lysine (873), tyrosine (43), arginine (26), phenylalanine (22), leucin (18), and valine (18) are preferred over serine.

FIG. 6B (SEQ ID NO:9) depicts a preferred GHA protein sequences based on the PDA analysis the hGH BOUNDARY2 sequence. Amino acid residues different from the hGH (see FIG. 1B)(SEQ ID NO:14) are underlined and shown in bold.

FIG. 7A depicts the mutation pattern of the CLUSTERED BOUNDARY sequences of hGH based on the analysis of the lowest 1000 protein sequences generated by Monte Carlo analysis the CLUSTERED BOUNDARY sequence (only the amino acid residues of positions 7, 14, 26, 29, 30, 34, 40, 43, 50, 57, 70, 77, 84, 87, 92, 98, 100, 102, 104, 106, 109, 111, 115, 118, 125, 132, 135, 137, 138, 140, 141, 142, 143, 144, 145, 147, 156, 159, 161, 184, 185, and 188 are given). The numbers following each amino acid indicate how often within the 1000 sequences analyzed, the indicated amino acid residue was found. For example, at position 50, the hGH amino acid is threonine (see FIG. 1B)(SEQ ID NO:14); in GHA proteins, 950 of the top 1000 sequences had phenylalanine at this position, and 50 of the sequences had methionine. None of the sequences had threonine at this position. Similarly, for position 102 (valine in hGH), isoleucine (962) is preferred over valine (38).

FIGS. 7B to 7E (SEQ ID NOS:10–13) depict preferred GHA protein sequences based on the PDA analysis the hGH CLUSTERED BOUNDARY sequence. Amino acid residues different from the hGH (see FIG. 1B) (SEQ ID NO:14) are underlined and shown in bold.

FIG. 8 depicts the synthesis of a full-length gene and all possible mutations by PCR. Overlapping oligonucleotides corresponding to the full-length gene (black bar, Step 1) and comprising one or more desired mutations are synthesized, heated and annealed. Addition of DNA polymerase to the annealed oligonucleotides results in the 5' to 3' synthesis of DNA (Step 2) to produce longer DNA fragments (Step 3). Repeated cycles of heating, annealing, and DNA synthesis (Step 4) result in the production of longer DNA, including some full-length molecules. These can be selected by a second round of PCR using primers (indicated by arrows) corresponding to the end of the full-length gene (Step 5).

FIG. 9 depicts a preferred scheme for synthesizing an IbA library of the invention. The wild type gene, or any starting gene, such as the gene for the global minima gene, can be used.

Oligonucleotides comprising sequences that encode different amino acids at the different variant positions (indicated in the Figure by box 1, box 2, and box 3) can be used during PCR. Those primers can be used in combination with standard primers. This generally requires fewer oligonucleotides and can result in fewer errors.

FIG. 10 depicts an overlapping extension method. At the top of FIG. 10A is the template DNA showing the locations of the regions to be mutated (black boxes) and the binding sites of the relevant primers (arrows). The primers R1 and R2 represent a pool of primers, each containing a different mutation; as described herein, this may be done using different ratios of primers if desired. The variant position is flanked by regions of homology sufficient to get hybridization. Thus, as shown in this example, oligos R1 and F2 comprise a region of homology and so do oligos R2 and F3. In this example, three separate PCR reactions are done for step 1. The first reaction contains the template plus oligos F1 and R1. The second reaction contains template plus oligos F2 and R2, and the third contains the template and oligos F3 and R3. The reaction products are shown. In Step 2, the products from Step 1 tube 1 and Step 1 tube 2 are taken. After purification away from the primers, these are added to a fresh PCR reaction together with F1 and R4. During the denaturation phase of the PCR, the overlapping regions anneal and the second strand is synthesized. The product is then amplified by the outside primers, F1 and R4. In Step 3, the purified product from Step 2 is used in a third PCR reaction, together with the product of Step 1, tube 3 and the primers F1 and R3. The final product corresponds to the full length gene and contains the required mutations. Alternatively, Step 2 and Step 3 can be performed in one PCR reaction.

FIG. 11 depicts a ligation of PCR reaction products to synthesize the libraries of the invention. In this technique, the primers also contain an endonuclease restriction site (RE), either generating blunt ends, 5' overhanging ends or 3' overhanging ends. We set up three separate PCR reactions for Step 1. The first reaction contains the template plus oligos F1 and R1. The second reaction contains template plus oligos F2 and R2, and the third contains the template and oligos F3 and R3. The reaction products are shown. In Step 2, the products of Step 1 are purified and then digested with the appropriate restriction endonuclease. The digestion products from Step 2, tube 1 and Step 2, tube 2 are ligated together with DNA ligase (Step 3). The products are then amplified in Step 4 using oligos F1 and R4. The whole process is then repeated by digesting the amplified products, ligating them to the digested products of Step 2, tube 3, and then amplifying the final product using oligos F1 and R3. It would also be possible to ligate all three PCR products from Step 1 together in one reaction, providing the two restriction sites (RE1 and RE2) were different.

FIG. 12 depicts blunt end ligation of PCR products. In this technique, oligos such as F2 and R1 or R2 and F3 do not overlap, but they abut. Again three separate PCR reactions are performed. The products from tube 1 and tube 2 (see FIG. 11, Step 1) are ligated, and then amplified with outside primers F1 and R4. This product is then ligated with the product from Step 1, tube 3. The final products are then amplified with primers F1 and R3.

FIG. 13 depicts thermal denaturation (CD spectroscopy) curves for wild type hGH and GHA mutants b and d. Mutants b and d show an increase in thermostability over hGH of 16° C. and of 13° C., respectively.

DETAILED DESCRIPTION OF THE INVENTION

The present invention is directed to novel proteins and nucleic acids possessing growth hormone activity (sometimes referred to herein as "GHA proteins" and "GHA nucleic acids"). The proteins are generated using a system previously described in WO98/47089 and U.S. Ser. Nos. 09/058,459, 09/127,926, 60/104,612, 60/158,700, 09/419, 351, 60/181,630, 60/186,904, U.S. patent application, entitled Protein Design Automation For Protein Libraries (Filed: Apr. 14, 2000; Inventor: Bassil Dahiyat), and PCT US98/07254, all of which are expressly incorporated by reference in their entirety, that is a computational modeling system that allows the generation of extremely stable proteins without necessarily disturbing the biological functions of the protein itself. In this way, novel GHA proteins and nucleic acids are generated, that can have a plurality of mutations in comparison to the wild-type enzyme yet retain significant activity.

Generally, there are a variety of computational methods that can be used to generate the GHA proteins of the invention. In a preferred embodiment, sequence based methods are used. Alternatively, structure based methods, such as PDA, described in detail below, are used.

Similarly, molecular dynamics calculations can be used to computationally screen sequences by individually calculating mutant sequence scores and compiling a rank ordered list.

In a preferred embodiment, residue pair potentials can be used to score sequences (Miyazawa et al., Macromolecules 18(3):534–552 (1985), expressly incorporated by reference) during computational screening.

In a preferred embodiment, sequence profile scores (Bowie et al., Science 253(5016):164–70 (1991), incorporated by reference) and/or potentials of mean force (Hendlich et al., J. Mol. Biol. 216(1):167–180 (1990), also incorporated by reference) can also be calculated to score sequences. These methods assess the match between a sequence and a 3D protein structure and hence can act to screen for fidelity to the protein structure. By using different scoring functions to rank sequences, different regions of sequence space can be sampled in the computational screen.

Furthermore, scoring functions can be used to screen for sequences that would create metal or co-factor binding sites in the protein (Hellinga, Fold Des. 3(1):R1–8 (1998), hereby expressly incorporated by reference). Similarly, scoring functions can be used to screen for sequences that would create disulfide bonds in the protein. These potentials attempt to specifically modify a protein structure to introduce a new structural motif.

In a preferred embodiment, sequence and/or structural alignment programs can be used to generate the GHA proteins of the invention. As is known in the art, there are a number of sequence-based alignment programs; including for example, Smith-Waterman searches, Needleman-Wunsch, Double Affine Smith-Waterman, frame search, Gribskov/GCG profile search, Gribskov/GCG profile scan, profile frame search, Bucher generalized profiles, Hidden Markov models, Hframe, Double Frame, Blast, Psi-Blast, Clustal, and GeneWise.

As is known in the art, there are a number of sequence alignment methodologies that can be used. For example, sequence homology based alignment methods can be used to create sequence alignments of proteins related to the target structure (Altschul et al., J. Mol. Biol. 215(3):403–410 (1990), Altschul et al., Nucleic Acids Res. 25:3389–3402 (1997), both incorporated by reference). These sequence alignments are then examined to determine the observed sequence variations. These sequence variations are tabulated to define a set of GHA proteins.

Sequence based alignments can be used in a variety of ways. For example, a number of related proteins can be aligned, as is known in the art, and the "variable" and "conserved" residues defined; that is, the residues that vary or remain identical between the family members can be defined. These results can be used to generate a probability table, as outlined below. Similarly, these sequence variations can be tabulated and a secondary library defined from them as defined below. Alternatively, the allowed sequence variations can be used to define the amino acids considered at each position during the computational screening. Another variation is to bias the score for amino acids that occur in the sequence alignment, thereby increasing the likelihood that they are found during computational screening but still allowing consideration of other amino acids. This bias would result in a focused library of GHA proteins but would not eliminate from consideration amino acids not found in the alignment. In addition, a number of other types of bias may be introduced. For example, diversity may be forced; that is, a "conserved" residue is chosen and altered to force diversity on the protein and thus sample a greater portion of the sequence space. Alternatively, the positions of high variability between family members (i.e. low conservation) can be randomized, either using all or a subset of amino acids. Similarly, outlier residues, either positional outliers or side chain outliers, may be eliminated.

Similarly, structural alignment of structurally related proteins can be done to generate sequence alignments (Orengo et al., Structure 5(8): 1093–108 (1997); Holm et al., Nucleic Acids Res. 26(1):316–9 (1998), both of which are incorporated by reference). These sequence alignments can then be examined to determine the observed sequence variations. Libraries can be generated by predicting secondary structure from sequence, and then selecting sequences that are compatible with the predicted secondary structure. There are a number of secondary structure prediction methods such as helix-coil transition theory (Munoz and Serrano, Biopolymers 41:495, 1997), neural networks, local structure alignment and others (e.g., see in Selbig et al., Bioinformatics 15:1039–46, 1999).

Similarly, as outlined above, other computational methods are known, including, but not limited to, sequence profiling [Bowie and Eisenberg, Science 253(5016): 164–70, (1991)], rotamer library selections [Dahiyat and Mayo, Protein Sci. 5(5):895–903 (1996); Dahiyat and Mayo, Science 278(5335):82–7 (1997); Desjarlais and Handel, Protein Science 4:2006–2018 (1995); Harbury et al, Proc. Natl. Acad. Sci. U.S.A. 92(18):8408–8412 (1995); Kono et al., Proteins: Structure, Function and Genetics 19:244–255 (1994); Hellinga and Richards, Proc. Natl. Acad. Sci. U.S.A. 91:5803–5807 (1994)]; and residue pair potentials [Jones, Protein Science 3: 567–574, (1994)]; PROSA [Heindlich et al., J. Mol. Biol. 216:167–180 (1990)]; THREADER [Jones et al., Nature 358:86–89 (1992)], and other inverse folding methods such as those described by Simons et al. [Proteins, 34:535–543, (1999)], Levitt and Gerstein [Proc. Natl. Acad. Sci. U.S.A., 95:5913–5920, (1998)], Godzik and Skolnick [Proc. Natl. Acad. Sci. U.S.A., 89:12098–102, (1992)], Godzik et al. [J. Mol. Biol. 227:227–38, (1992)] and two profile methods [Gribskov et al. Proc. Natl. Acad. Sci. U.S.A. 84:4355–4358 (1987) and Fischer and Eisenberg, Protein Sci. 5:947–955 (1996), Rice and Eisenberg J. Mol. Biol. 267:1026–1038(1997)], all of which are expressly incorporated by reference. In addition, other computational methods such as those described by Koehl and Levitt (J. Mol. Biol. 293:1161–1181 (1999); J. Mol. Biol. 293:1183–1193 (1999); expressly incorporated by reference) can be used to create a protein sequence library which can optionally then be used to generate a smaller secondary library for use in experimental screening for improved properties and function. In addition, there are computational methods based on forcefield calculations such as SCMF that can be used as well for SCMF, see Delarue et al. Pac. Symp. Biocomput. 109–21 (1997); Koehl et al., J. Mol. Biol. 239:249–75 (1994); Koehl et al., Nat. Struct. Biol. 2:163–70 (1995); Koehl et al., Curr. Opin. Struct. Biol. 6:222–6 (1996); Koehl et al., J. Mol. Biol. 293:1183–93 (1999); Koehl et al., J. Mol. Biol. 293:1161–81 (1999); Lee J., Mol. Biol. 236:918–39 (1994); and Vasquez Biopolymers 36:53–70 (1995); all of which are expressly incorporated by reference. Other forcefield calculations that can be used to optimize the conformation of a sequence within a computational method, or to generate de novo optimized sequences as outlined herein include, but are not limited to, OPLS-AA [Jorgensen et al., J. Am. Chem. Soc. 118:11225–11236 (1996); Jorgensen, W. L.; BOSS, Version 4.1; Yale University: New Haven, Conn. (1999)]; OPLS [Jorgensen et al., J. Am. Chem. Soc. 110:1657ff (1988); Jorgensen et al., J Am. Chem. Soc. 1 12:4768ff (1990)]; UNRES (United Residue Forcefield; Liwo et al., Protein Science 2:1697–1714 (1993); Liwo et al., Protein Science 2:1715–1731 (1993); Liwo et al., J. Comp. Chem. 18:849–873 (1997); Liwo et al., J. Comp. Chem.

18:874–884 (1997); Liwo et al., J. Comp. Chem. 19:259–276 (1998); Forcefield for Protein Structure Prediction (Liwo et al., Proc. Natl. Acad. Sci. U.S.A. 96:5482–5485 (1999)]; ECEPP/3 [Liwo et al., J Protein Chem. 13(4):375–80 (1994)]; AMBER 1.1 force field (Weiner et al., J. Am. Chem. Soc. 106:765–784); AMBER 3.0 force field [U.C. Singh et al., Proc. Natl. Acad. Sci. U.S.A.. 82:755–759 (1985)]; CHARMM and CHARMM22 (Brooks et al., J. Comp. Chem. 4:187–217); cvff3.0 [Dauber-Osguthorpe et al., Proteins: Structure, Function and Genetics, 4:31–47 (1988)]; cff91 (Maple et al., J. Comp. Chem. 15:162–182); also, the DISCOVER (cvff and cff91) and AMBER forcefields are used in the INSIGHT molecular modeling package (Biosym/MSI, San Diego Calif.) and HARMM is used in the QUANTA molecular modeling package (Biosym/MSI, San Diego Calif.), all of which are expressly incorporated by reference. In fact, as is outlined below, these forcefield methods may be used to generate the secondary library directly; that is, no primary library is generated; rather, these methods can be used to generate a probability table from which the secondary library is directly generated.

In a preferred embodiment, the computational method used to generate the primary library is Protein Design Automation (PDA), as is described in U.S. Ser. Nos. 60/061,097, 60/043,464, 60/054,678, 09/127,926, 60/104,612, 60/158,700, 09/419,351, 60/181,630, 60/186,904, U.S. patent application, entitled Protein Design Automation For Protein Libraries (Filed: Apr. 14, 2000; Inventor. Bassil Dahiyat), and PCT US98/07254, all of which are expressly incorporated herein by reference. Briefly, PDA can be described as follows. A known protein structure is used as the starting point. The residues to be optimized are then identified, which may be the entire sequence or subset(s) thereof. The side chains of any positions to be varied are then removed. The resulting structure consisting of the protein backbone and the remaining sidechains is called the template. Each variable residue position is then preferably classified as a core residue, a surface residue, or a boundary residue; each classification defines a subset of possible amino acid residues for the position (for example, core residues generally will be selected from the set of hydrophobic residues, surface residues generally will be selected from the hydrophilic residues, and boundary residues may be either). Each amino acid can be represented by a discrete set of all allowed conformers of each side chain, called rotamers. Thus, to arrive at an optimal sequence for a backbone, all possible sequences of rotamers must be screened, where each backbone position can be occupied either by each amino acid in all its possible rotameric states, or a subset of amino acids, and thus a subset of rotamers.

Two sets of interactions are then calculated for each rotamer at every position: the interaction of the rotamer side chain with all or part of the backbone (the "singles" energy, also called the rotamer/template or rotamer/backbone energy), and the interaction of the rotamer side chain with all other possible rotamers at every other position or a subset of the other positions (the "doubles" energy, also called the rotamer/rotamer energy). The energy of each of these interactions is calculated through the use of a variety of scoring functions, which include the energy of van der Waal's forces, the energy of hydrogen bonding, the energy of secondary structure propensity, the energy of surface area solvation and the electrostatics. Thus, the total energy of each rotamer interaction, both with the backbone and other rotamers, is calculated, and stored in a matrix form.

The discrete nature of rotamer sets allows a simple calculation of the number of rotamer sequences to be tested. A backbone of length n with m possible rotamers per position will have $m^n$ possible rotamer sequences, a number which grows exponentially with sequence length and renders the calculations either unwieldy or impossible in real time. Accordingly, to solve this combinatorial search problem, a "Dead End Elimination" (DEE) calculation is performed. The DEE calculation is based on the fact that if the worst total interaction of a first rotamer is still better than the best total interaction of a second rotamer, then the second rotamer cannot be part of the global optimum solution. Since the energies of all rotamers have already been calculated, the DEE approach only requires sums over the sequence length to test and eliminate rotamers, which speeds up the calculations considerably. DEE can be rerun comparing pairs of rotamers, or combinations of rotamers, which will eventually result in the determination of a single sequence which represents the global optimum energy.

Once the global solution has been found, a Monte Carlo search may be done to generate a rank-ordered list of sequences in the neighborhood of the DEE solution. Starting at the DEE solution, random positions are changed to other rotamers, and the new sequence energy is calculated. If the new sequence meets the criteria for acceptance, it is used as a starting point for another jump. After a predetermined number of jumps, a rank-ordered list of sequences is generated. Monte Carlo searching is a sampling technique to explore sequence space around the global minimum or to find new local minima distant in sequence space. As is more additionally outlined below, there are other sampling techniques that can be used, including Boltzman sampling, genetic algorithm techniques and simulated annealing. In addition, for all the sampling techniques, the kinds of jumps allowed can be altered (e.g. random jumps to random residues, biased jumps (to or away from wild-type, for example), jumps to biased residues (to or away from similar residues, for example), etc.). Similarly, for all the sampling techniques, the acceptance criteria of whether a sampling jump is accepted can be altered.

As outlined in U.S. Ser. No. 09/127,926, the protein backbone (comprising (for a naturally occurring protein) the nitrogen, the carbonyl carbon, the α-carbon, and the carbonyl oxygen, along with the direction of the vector from the α-carbon to the β-carbon) may be altered prior to the computational analysis, by varying a set of parameters called supersecondary structure parameters.

Once a protein structure backbone is generated (with alterations, as outlined above) and input into the computer, explicit hydrogens are added if not included within the structure (for example, if the structure was generated by X-ray crystallography, hydrogens must be added). After hydrogen addition, energy minimization of the structure is run, to relax the hydrogens as well as the other atoms, bond angles and bond lengths. In a preferred embodiment, this is done by doing a number of steps of conjugate gradient minimization [Mayo et al., J. Phys. Chem. 94:8897 (1990)] of atomic coordinate positions to minimize the Dreiding force field with no electrostatics. Generally from about 10 to about 250 steps is preferred, with about 50 being most preferred.

The protein backbone structure contains at least one variable residue position. As is known in the art, the residues, or amino acids, of proteins are generally sequentially numbered starting with the N-terminus of the protein. Thus a protein having a methionine at it's N-terminus is said to have a methionine at residue or amino acid position 1, with the next residues as 2, 3, 4, etc. At each position, the wild type (i.e. naturally occuring) protein may have one of at least 20 amino acids, in any number of rotamers. By "variable residue position" herein is meant an amino acid position of the protein to be designed that is not fixed in the design method as a specific residue or rotamer, generally the wild-type residue or rotamer.

In a preferred embodiment, all of the residue positions of the protein are variable. That is, every amino acid side chain may be altered in the methods of the present invention. This is particularly desirable for smaller proteins, although the present methods allow the design of larger proteins as well. While there is no theoretical limit to the length of the protein which may be designed this way, there is a practical computational limit.

In an alternate preferred embodiment, only some of the residue positions of the protein are variable, and the remainder are "fixed", that is, they are identified in the three dimensional structure as being in a set conformation. In some embodiments, a fixed position is left in its original conformation (which may or may not correlate to a specific rotamer of the rotamer library being used). Alternatively, residues may be fixed as a non-wild type residue; for example, when known site-directed mutagenesis techniques have shown that a particular residue is desirable (for example, to eliminate a proteolytic site or alter the substrate specificity of an enzyme), the residue may be fixed as a particular amino acid. Alternatively, the methods of the present invention may be used to evaluate mutations de novo, as is discussed below. In an alternate preferred embodiment, a fixed position may be "floated"; the amino acid at that position is fixed, but different rotamers of that amino acid are tested. In this embodiment, the variable residues may be at least one, or anywhere from 0.1% to 99.9% of the total number of residues. Thus, for example, it may be possible to change only a few (or one) residues, or most of the residues, with all possibilities in between.

In a preferred embodiment, residues which can be fixed include, but are not limited to, structurally or biologically functional residues; alternatively, biologically functional residues may specifically not be fixed. For example, residues which are known to be important for biological activity, such as the residues which the binding site for a binding partner (ligand/receptor, antigen/antibody, etc.), phosphorylation or glycosylation sites which are crucial to biological function, or structurally important residues, such as disulfide bridges, metal binding sites, critical hydrogen bonding residues, residues critical for backbone conformation such as proline or glycine, residues critical for packing interactions, etc. may all be fixed in a conformation or as a single rotamer, or "floated".

Similarly, residues which may be chosen as variable residues may be those that confer undesirable biological attributes, such as susceptibility to proteolytic degradation, dimerization or aggregation sites, glycosylation sites which may lead to immune responses, unwanted binding activity, unwanted allostery, undesirable enzyme activity but with a preservation of binding, etc.

In a preferred embodiment, each variable position is classified as either a core, surface or boundary residue position, although in some cases, as explained below, the variable position may be set to glycine to minimize backbone strain. In addition, as outlined herein, residues need not be classified, they can be chosen as variable and any set of amino acids may be used. Any combination of core, surface and boundary positions can be utilized: core, surface and boundary residues; core and surface residues; core and boundary residues, and surface and boundary residues, as well as core residues alone, surface residues alone, or boundary residues alone.

The classification of residue positions as core, surface or boundary may be done in several ways, as will be appreciated by those in the art. In a preferred embodiment, the classification is done via a visual scan of the original protein backbone structure, including the side chains, and assigning a classification based on a subjective evaluation of one skilled in the art of protein modelling. Alternatively, a preferred embodiment utilizes an assessment of the orientation of the $C\alpha$-$C\beta$ vectors relative to a solvent accessible surface computed using only the template $C\alpha$ atoms, as outlined in U.S. Ser. Nos. 60/061,097, 60/043,464, 60/054,678, 09/127,926 60/104,612, 60/158,700, 09/419,351, 60/181,630, 60/186,904, U.S. patent application, entitled Protein Design Automation For Protein Libranes (Filed: Apr. 14, 2000; Inventor: Bassil Dahiyat) and PCT US98/07254. Alternatively, a surface area calculation can be done.

Suitable core and boundary positions for GHA proteins are outlined below.

Once each variable position is classified as either core, surface or boundary, a set of amino acid side chains, and thus a set of rotamers, is assigned to each position. That is, the set of possible amino acid side chains that the program will allow to be considered at any particular position is chosen. Subsequently, once the possible amino acid side chains are chosen, the set of rotamers that will be evaluated at a particular position can be determined. Thus, a core residue will generally be selected from the group of hydrophobic residues consisting of alanine, valine, isoleucine, leucine, phenylalanine, tyrosine, tryptophan, and methionine (in some embodiments, when the $\alpha$ scaling factor of the van der Waals scoring function, described below, is low, methionine is removed from the set), and the rotamer set for each core position potentially includes rotamers for these eight amino acid side chains (all the rotamers if a backbone independent library is used, and subsets if a rotamer dependent backbone is used). Similarly, surface positions are generally selected from the group of hydrophilic residues consisting of alanine, serine, threonine, aspartic acid, asparagine, glutamine, glutamic acid, arginine, lysine and histidine. The rotamer set for each surface position thus includes rotamers for these ten residues. Finally, boundary positions are generally chosen from alanine, serine, threonine, aspartic acid, asparagine, glutamine, glutamic acid, arginine, lysine histidine, valine, isoleucine, leucine, phenylalanine, tyrosine, tryptophan, and methionine. The rotamer set for each boundary position thus potentially includes every rotamer for these seventeen residues (assuming cysteine, glycine and proline are not used, although they can be). Additionally, in some preferred embodiments, a set of 18 naturally occuring amino acids (all except cysteine and proline, which are known to be particularly disruptive) are used.

Thus, as will be appreciated by those in the art, there is a computational benefit to classifying the residue positions, as it decreases the number of calculations. It should also be noted that there may be situations where the sets of core, boundary and surface residues are altered from those described above; for example, under some circumstances, one or more amino acids is either added or subtracted from the set of allowed amino acids. For example, some proteins which dimerize or multimerize, or have ligand binding sites, may contain hydrophobic surface residues, etc. In addition, residues that do not allow helix "capping" or the favorable interaction with an $\alpha$-helix dipole may be subtracted from a set of allowed residues. This modification of amino acid groups is done on a residue by residue basis.

In a preferred embodiment, proline, cysteine and glycine are not included in the list of possible amino acid side chains, and thus the rotamers for these side chains are not used. However, in a preferred embodiment, when the variable residue position has a φ angle (that is, the dihedral angle defined by 1) the carbonyl carbon of the preceding amino acid; 2) the nitrogen atom of the current residue; 3) the α-carbon of the current residue; and 4) the carbonyl carbon of the current residue) greater than 0☐, the position is set to glycine to minimize backbone strain.

Once the group of potential rolamers is assigned for each variable residue position, processing proceeds as outlined in U.S. Ser. No. 09/127,926 and PCT US98/07254. This processing step entails analyzing interactions of the rotamers with each other and with the protein backbone to generate optimized protein sequences. Simplistically, the processing initially comprises the use of a number of scoring functions to calculate energies of interactions of the rotamers, either to the backbone itself or other rotamers. Preferred PDA scoring functions include, but are not limited to, a Van der Waals potential scoring function, a hydrogen bond potential scoring function, an atomic solvation scoring function, a secondary structure propensity scoring function and an electrostatic scoring function. As is further described below, at least one scoring function is used to score each position, although the scoring functions may differ depending on the position classification or other considerations, like favorable interaction with an α-helix dipole. As outlined below, the total energy which is used in the calculations is the sum of the energy of each scoring function used at a particular position, as is generally shown in Equation 1:

$$E_{total} = nE_{vdw} + nE_{as} + nE_{h\text{-}bonding} + nE_{ss} + nE_{elec}$$  Equation 1

In Equation 1, the total energy is the sum of the energy of the van der Waals potential ($E_{vdw}$), the energy of atomic solvation ($E_{as}$), the energy of hydrogen bonding ($E_{h\text{-}bonding}$), the energy of secondary structure ($E_{ss}$) and the energy of electrostatic interaction ($E_{elec}$). The term n is either 0 or 1, depending on whether the term is to be considered for the particular residue position.

As outlined in U.S. Ser. Nos. 60/061,097, 60/043,464, 60/054,678, 09/127,926, 60/104,612, 60/158,700, 09/419, 351, 60/181,630, 60/186,904, U.S. patent application, entitled Protein Design Automation For Protein Libraries (Filed: Apr. 14, 2000; Inventor Bassil Dahiyat), and PCT US98/07254, any combination of these scoring functions, either alone or in combination, may be used. Once the scoring functions to be used are identified for each variable position, the preferred first step in the computational analysis comprises the determination of the interaction of each possible rotamer with all or part of the remainder of the protein. That is, the energy of interaction, as measured by one or more of the scoring functions, of each possible rotamer at each variable residue position with either the backbone or other rotamers, is calculated. In a preferred embodiment, the interaction of each rotamer with the entire remainder of the protein, i.e. both the entire template and all other rotamers, is done. However, as outlined above, it is possible to only model a portion of a protein, for example a domain of a larger protein, and thus in some cases, not all of the protein need be considered. The term "portion", or similar grammatical equivalents thereof, as used herein, with regard to a protein refers to a fragment of that protein. This fragment may range in size from 5–10 amino acid residues to the entire amino acid sequence minus one amino acid. Accordingly, the term "portion", as used herein, with regard to a nucleic refers to a fragment of that nucleic acid. This fragment may range in size from 6–10 nucleotides to the entire nucleic acid sequence minus one nucleotide.

In a preferred embodiment, the first step of the computational processing is done by calculating two sets of interactions for each rotamer at every position: the interaction of the rotamer side chain with the template or backbone (the "singles" energy), and the interaction of the rotamer side chain with all other possible rotamers at every other position (the "doubles" energy), whether that position is varied or floated. It should be understood that the backbone in this case includes both the atoms of the protein structure backbone, as well as the atoms of any fixed residues, wherein the fixed residues are defined as a particular conformation of an amino acid.

Thus, "singles" (rotamer/template) energies are calculated for the interaction of every possible rotamer at every variable residue position with the backbone, using some or all of the scoring functions. Thus, for the hydrogen bonding scoring function, every hydrogen bonding atom of the rotamer and every hydrogen bonding atom of the backbone is evaluated, and the $E_{HB}$ is calculated for each possible rotamer at every variable position. Similarly, for the van der Waals scoring function, every atom of the rotamer is compared to every atom of the template (generally excluding the backbone atoms of its own residue), and the $E_{vdW}$ is calculated for each possible rotamer at every variable residue position. In addition, generally no van der Waals energy is calculated if the atoms are connected by three bonds or less. For the atomic salvation scoring function, the surface of the rotamer is measured against the surface of the template, and the $E_{as}$ for each possible rotamer at every variable residue position is calculated. The secondary structure propensity scoring function is also considered as a singles energy, and thus the total singles energy may contain an $E_{ss}$ term. As will be appreciated by those in the art, many of these energy terms will be close to zero, depending on the physical distance between the rotamer and the template position; that is, the farther apart the two moieties, the lower the energy.

For the calculation of "doubles" energy (rotamer/rotamer), the interaction energy of each possible rotamer is compared with every possible rotamer at all other variable residue positions.

Thus, "doubles" energies are calculated for the interaction of every possible rotamer at every variable residue position with every possible rotamer at every other variable residue position, using some or all of the scoring functions. Thus, for the hydrogen bonding scoring function, every hydrogen bonding atom of the first rotamer and every hydrogen bonding atom of every possible second rotamer is evaluated, and the $E_{HB}$ is calculated for each possible rotamer pair for any two variable positions. Similarly, for the van der Waals scoring function, every atom of the first rotamer is compared to every atom of every possible second rotamer, and the $E_{vdW}$ is calculated for each possible rotamer pair at every two variable residue positions. For the atomic solvation scoring function, the surface of the first rotamer is measured against the surface of every possible second rotamer, and the $E_{as}$ for each possible rotamer pair at every two variable residue positions is calculated. The secondary structure propensity scoring function need not be run as a "doubles" energy, as it is considered as a component of the "singles" energy. As will be appreciated by those in the art, many of these double energy terms will be close to zero, depending on the physical distance between the first rotamer and the second rotamer; that is the farther apart the two moieties, the lower the energy.

In addition, as will be appreciated by those in the art, a variety of force fields that can be used in the PDA calculations can be used, including, but not limited to, Dreiding I and Dreiding II [Mayo et al, J. Phys. Chem. 94:8897 (1990)], AMBER [Weiner et al., J. Amer. Chem. Soc. 106:765 (1984) and Weiner et al., J. Comp. Chem. 106:230 (1986)], MM2 [Allinger, J. Chem. Soc. 99:8127 (1977), Liljefors et al., J. Com. Chem. 8:1051 (1987)]; MMP2 [Sprague et al., J. Comp. Chem. 8:581 (1987)]; CHARMM [Brooks et al., J. Comp. Chem. 106:187 (1983)]; GROMOS; and MM3 [Allinger et al., J. Amer. Chem. Soc. 111:8551 (1989)], OPLS-AA [Jorgensen et al., J. Am. Chem. Soc. 118:11225–11236 (1996); Jorgensen, W. L.; BOSS, Version 4.1; Yale University: New Haven, Conn. (1999)]; OPLS [Jorgensen et al., J. Am. Chem. Soc. 110:1657ff (1988); Jorgensen et al., J Am. Chem. Soc. 112:4768ff (1990)]; UNRES (United Residue Forcefield; Liwo et al., Protein Science 2:1697–1714 (1993); Liwo et al., Protein Science 2:1715–1731 (1993); Liwo et al., J. Comp. Chem. 18:849–873 (1997); Liwo et al., J. Comp. Chem. 18:874–884 (1997); Liwo et al., J. Comp. Chem. 19:259–276 (1998); Forcefield for Protein Structure Prediction (Liwo et al., Proc. Nati. Acad. Sci. U.S.A 96:5482–5485 (1999)]; ECEPP/3 [Liwo et al., J Protein Chem. 13(4): 375–80 (1994)]; AMBER 1.1 force field (Weiner, et al., J. Am. Chem. Soc. 106:765–784); AMBER 3.0 force field (U.C. Singh et al., Proc. Natl. Acad. Sci. U.S.A. 82:755–759); CHARMM and CHARMM22 (Brooks et al., J. Comp. Chem. 4:187–217); cvff3.0 [Dauber-Osguthorpe, et al., Proteins: Structure, Function and Genetics, 4:31–47 (1988)]; cff91 (Maple, et al., J. Comp. Chem. 15:162–182); also, the DISCOVER (cvff and cff91) and AMBER force-fields are used in the INSIGHT molecular modeling package (Biosym/MSI, San Diego Calif.) and HARMM is used in the QUANTA molecular modeling package (Biosym/MSI, San Diego Calif.), all of which are expressly incorporated by reference.

Once the singles and doubles energies are calculated and stored, the next step of the computational processing may occur. As outlined in U.S. Ser. No. 09/127, 926 and PCT US98/07254, preferred embodiments utilize a Dead End Elimination (DEE) step, and preferably a Monte Carlo step.

PDA, viewed broadly, has three components that may be varied to alter the output (e.g. the primary library): the scoring functions used in the process; the filtering technique, and the sampling technique.

In a preferred embodiment, the scoring functions may be altered. In a preferred embodiment, the scoring functions outlined above may be biased or weighted in a variety of ways. For example, a bias towards or away from a reference sequence or family of sequences can be done; for example, a bias towards wild-type or homolog residues may be used. Similarly, the entire protein or a fragment of it may be biased; for example, the active site may be biased towards wild-type residues, or domain residues towards a particular desired physical property can be done. Furthermore, a bias towards or against increased energy can be generated. Additional scoring function biases include, but are not limited to applying electrostatic potential gradients or hydrophobicity gradients, adding a substrate or binding partner to the calculation, or biasing towards a desired charge or hydrophobicity.

In addition, in an alternative embodiment, there are a variety of additional scoring functions that may be used. Additional scoring functions include, but are not limited to torsional potentials, or residue pair potentials, or residue entropy potentials. Such additional scoring functions can be used alone, or as functions for processing the library after it is scored initially. For example, a variety of functions derived from data on binding of peptides to MHC (Major Histocompatibility Complex) can be used to rescore a library in order to eliminate proteins containing sequences which can potentially bind to MHC, i.e. potentially immunogenic sequences.

In a preferred embodiment, a variety of filtering techniques can be done, including, but not limited to, DEE and its related counterparts. Additional filtering techniques include, but are not limited to branch-and-bound techniques for finding optimal sequences (Gordon and Mayo, Structure Fold. Des. 7:1089–98, 1999), and exhaustive enumeration of sequences.

As will be appreciated by those in the art, once an optimized sequence or set of sequences is generated, a variety of sequence space sampling methods can be done, either in addition to the preferred Monte Carlo methods, or instead of a Monte Carlo search. That is, once a sequence or set of sequences is generated, preferred methods utilize sampling techniques to allow the generation of additional, related sequences for testing.

These sampling methods can include the use of amino acid substitutions, insertions or deletions, or recombinations of one or more sequences. As outlined herein, a preferred embodiment utilizes a Monte Carlo search, which is a series of biased, systematic, or random jumps. However, there are other sampling techniques that can be used, including Boltzman sampling, genetic algorithm techniques and simulated annealing. In addition, for all the sampling techniques, the kinds of jumps allowed can be altered (e.g. random jumps to random residues, biased jumps (to or away from wild-type, for example), jumps to biased residues (to or away from similar residues, for example, etc.). Jumps where multiple residue positions are coupled (two residues always change together, or never change together), jumps where whole sets of residues change to other sequences (e.g., recombination). Similarly, for all the sampling techniques, the acceptance criteria of whether a sampling jump is accepted can be altered.

In addition, it should be noted that the preferred methods of the invention result in a rank ordered list of sequences; that is, the sequences are ranked on the basis of some objective criteria. However, as outlined herein, it is possible to create a set of non-ordered sequences, for example by generating a probability table directly (for example using SCMF analysis or sequence alignment techniques) that lists sequences without ranking them. The sampling techniques outlined herein can be used in either situation.

In a preferred embodiment, Boltzman sampling is done. As will be appreciated by those in the art, the temperature criteria for Boltzman sampling can be altered to allow broad searches at high temperature and narrow searches close to local optima at low temperatures (see e.g., Metropolis et al., J. Chem. Phys. 21:1087, 1953).

In a preferred embodiment, the sampling technique utilizes genetic algorithms, e.g., such as those described by Holland (Adaptation in Natural and Artificial Systems, 1975, Ann Arbor, U. Michigan Press). Genetic algorithm analysis generally takes generated sequences and recombines them computationally, similar to a nucleic acid recombination event, in a manner similar to "gene shuffling". Thus the "jumps" of genetic algorithm analysis generally are multiple position jumps. In addition, as outlined below, correlated multiple jumps may also be done. Such jumps can occur with different crossover positions and more than one recombination at a time, and can involve recombination of two or more sequences. Furthermore, deletions or insertions (random or biased) can be done. In addition, as outlined below, genetic algorithm analysis may also be used after the secondary library has been generated.

In a preferred embodiment, the sampling technique utilizes simulated annealing, e.g., such as described by Kirkpatrick et al. [Science, 220:671–680 (1983)]. Simulated annealing alters the cutoff for accepting good or bad jumps by altering the temperature. That is, the stringency of the cutoff is altered by altering the temperature. This allows broad searches at high temperature to new areas of sequence space, altering with narrow searches at low temperature to explore regions in detail.

In addition, as outlined below, these sampling methods can be used to further process a first set to generate additional sets of GHA proteins.

The computational processing results in a set of optimized GHA protein sequences. These optimized GHA protein sequences are generally significantly different from the wild-type GH sequence from which the backbone was taken. That is, each optimized GHA protein sequence preferably comprises at least about 3–10% variant amino acids from the starting or wild type sequence, with at least about 10–15% being preferred, with at least about 15–20% changes being more preferred and at least 25% being particularly preferred.

In a preferred embodiment, the GHA proteins of the invention have 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 different residues from the hGH sequence.

Thus, in the broadest sense, the present invention is directed to GHA proteins that have GH activity. By "GH activity" or "GHA" herein is meant that the protein exhibits at least one, and preferably more, of the biological functions of a growth hormone, as defined below. In one embodiment, the biological function of a GHA protein is altered, preferably improved, over the corresponding biological activity of a GH.

By "protein" herein is meant at least two covalently attached amino acids, which includes proteins, polypeptides, oligopeptides and peptides. The protein may be made up of naturally occurring amino acids and peptide bonds, or synthetic peptidomimetic structures, i.e., "analogs" such as peptoids [see Simon et al., Proc. Natl. Acd. Sci. U.S.A. 89(20:9367–71 (1992)], generally depending on the method of synthesis. Thus "amino acid", or "peptide residue", as used herein means both naturally occurring and synthetic amino acids. For example, homo-phenylalanine, citrulline, and norleucine are considered amino acids for the purposes of the invention. "Amino acid" also includes imino acid residues such as proline and hydroxyproline. In addition, any amino acid representing a component of the GHA proteins can be replaced by the same amino acid but of the opposite chirality. Thus, any amino acid naturally occurring in the L-configuration (which may also be referred to as the R or S, depending upon the structure of the chemical entity) may be replaced with an amino acid of the same chemical structural type, but of the opposite chirality, generally referred to as the D-amino acid but which can additionally be referred to as the R- or the S-, depending upon its composition and chemical configuration. Such derivatives have the property of greatly increased stability, and therefore are advantageous in the formulation of compounds which may have longer in vivo half lives, when administered by oral, intravenous, intramuscular, intraperitoneal, topical, rectal, intraocular, or other routes. In the preferred embodiment, the amino acids are in the (S) or L-configuration. If non-naturally occurring side chains are used, non-amino acid substituents may be used, for example to prevent or retard in vivo degradations. Proteins including non-naturally occurring amino acids may be synthesized or in some cases, made recombinantly; see van Hest et al., FEBS Lett 428:(1–2) 68–70 May 22 1998 and Tang et al., Abstr. Pap Am. Chem. S218:U138—U138 Part 2 Aug. 22, 1999, both of which are expressly incorporated by reference herein.

Additionally, modified amino acids or chemical derivatives of amino acids of consensus or fragments of GHA proteins, according to the present invention may be provided, which polypeptides contain additional chemical moieties or modified amino acids not normally a part of the protein. Covalent and non-covalent modifications of the protein are thus included within the scope of the present invention. Such modifications may be introduced into a GHA polypeptide by reacting targeted amino acid residues of the polypeptide with an organic derivatizing agent that is capable of reacting with selected side chains or terminal residues. The following examples of chemical derivatives are provided by way of illustration and not by way of limitation.

Aromatic amino acids may be replaced with D- or L-naphylalanine, D- or L-Phenylglycine, D- or L-2-thieneylalanine, D- or L-1-, 2-, 3- or 4-pyreneylalanine, D- or L-3-thieneylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylphenylalanine, D- or L-p-methoxybiphenylphenylalanine, D- or L-2-indole (alkyl)alanines, and D- or L-alkylainines where alkyl may be substituted or unsubstituted methyl, ethyl, propyl, hexyl, butyl, pentyl, isopropyl, iso-butyl, sec-isotyl, iso-pentyl, non-acidic amino acids, of C1–C20.

Acidic amino acids can be substituted with noncarboxylate amino acids while maintaining a negative charge, and derivatives or analogs thereof, such as the non-limiting examples of (phosphono)alanine, glycine, leucine, isoleucine, threonine, or serine; or sulfated (e.g., —SO$_3$H) threonine, serine, tyrosine.

Other substitutions may include unnatural hyroxylated amino acids that may be made by combining "alkyl" with any natural amino acid. The term "alkyl" as used herein refers to a branched or unbranched saturated hydrocarbon group of 1 to 24 carbon atoms, such as methyl, ethyl, n-propyl, isoptopyl, n-butyl, isobutyl, t-butyl, octyl, decyl, tetradecyl, hexadecyl, eicosyl, tetracisyl and the like. Preferred alkyl groups herein contain 1 to 12 carbon atoms. Also included within the definition of an alkyl group are cycloalkyl groups such as C5 and C6 rings, and heterocyclic rings with nitrogen, oxygen, sulfur or phosphorus. Alkyl also includes heteroalkyl, with heteroatoms of sulfur, oxygen, and nitrogen being preferred. Alkyl includes substituted alkyl groups. By "substituted alkyl group" herein is meant an alkyl group further comprising one or more substitution moieties. A preferred heteroalkyl group is an alkyl amine. By "alkyl amine" or grammatical equivalents herein is meant an alkyl group as defined above, substituted with an amine group at any position. In addition, the alkyl amine may have other substitution groups, as outlined above for alkyl group. The amine may be primary (—NH$_2$R), secondary (—NHR$_2$), or tertiary (—NR$_3$). Basic amino acids may be substituted with alkyl groups at any position of the naturally occurring amino acids lysine, arginine, ornithine, citrulline, or (guanidino)-acetic acid, or other (guanidino)alkyl-acetic acids, where "alkyl" is define as above. Nitrile derivatives (e.g., containing the CN-moiety in place of COOH) may also be substituted for asparagine or glutamine, and methionine sulfoxide may be substituted for methionine. Methods of preparation of such peptide derivatives are well known to one skilled in the art.

In addition, any amide linkage in any of the IbA polypeptides can be replaced by a ketomethylene moiety. Such derivatives are expected to have the property of increased stability to degradation by enzymes, and therefore possess advantages for the formulation of compounds which may have increased in vivo half lives, as administered by oral, intravenous, intramuscular, intraperitoneal, topical, rectal, intraocular, or other routes.

Additional amino acid modifications of amino acids of GHA polypeptides of to the present invention may include the following: Cysteinyl residues may be reacted with alpha-haloacetates (and corresponding amines), such as 2-chloroacetic acid or chloroacetamide, to give carboxymethyl or carboxyamidomethyl derivatives. Cysteinyl residues may also be derivatized by reaction with compounds such as bromotrifluoroacetone, alpha-bromo-beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues may be derivatized by reaction with compounds such as diethylprocarbonate e.g., at pH 5.5–7.0 because this agent is relatively specific for the histidyl side chain, and para-bromophenacyl bromide may also be used; e.g., where the reaction is preferably performed in 0.1M sodium cacodylate at pH 6.0.

Lysinyl and amino terminal residues may be reacted with compounds such as succinic or other carboxylic acid anhydrides. Derivatization with these agents is expected to have the effect of reversing the charge of the lysinyl residues. Other suitable reagents for derivatizing alpha-amino-containing residues include compounds such as imidoesters/ e.g., as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin according to known method steps. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues per se is well-known, such as for introducing spectral labels into tyrosyl residues by reaction with aromatic diazonium compounds or tetranitromethane. N-acetylimidizol and tetranitromethane may be used to form O-acetyl tyrosyl species and 3-nitro derivatives, respectively.

Carboxyl side groups (aspartyl or glutamyl) may be selectively modified by reaction with carbodiimides (R'-N-C-N-R') such as 1-cyclohexyl-3-(2-morpholinyl- (4-ethyl) carbodiimide or 1-ethyl-3-(4-azonia-4,4- dimethylpentyl) carbodiimide. Furthermore aspartyl and glutamyl residues may be converted to asparaginyl and glutaminyl residues by reaction with ammonium ions.

Glutaminyl and asparaginyl residues may be frequently deamidated to the corresponding glutamyl and aspartyl residues. Alternatively, these residues may be deamidated under mildly acidic conditions. Either form of these residues falls within the scope of the present invention.

The GH may be from any number of organisms, with GHs from mammals being particularly preferred. Suitable mammals include, but are not limited to, rodents (rats, mice, hamsters, guinea pigs, etc.), primates, farm animals (including sheep, goats, pigs, cows, horses, etc) and in the most preferred embodiment, from humans (this is sometimes referred to herein as hGH, the sequence of which is depicted in FIG. 1A (SEQ ID NO:1)). As will be appreciated by those in the art, GHs based on GHs from mammals other than humans may find use in animal models of human disease. The GenBank numbers for a variety of mammalian HG species is as follows: bovine, RIBOS1, STBO, CAA00787, JC1316; dog, 146145, S35790; sheep, S33339, STSH; cat, JC4632, P46404; pig, STPG; mouse, STMS, P06880; rat, STRT, P01244; Rhesus macaque, I67411I67410; horse, STHO, P01245; human, P01241, STUV2 (somatropin 2 precursor, splice form 2), STUV (somatotropin 2 precursor), STHU (somatotropin 1 precursor).

The GHA proteins of the invention exhibit at least one biological function of a GH protein. By "growth hormone" or "GH" herein is meant a wild type GH or an allelic variant thereof. Thus, GH refers to all forms of growth hormone that are active in accepted GH assays (for examples of assays, referenced in U.S. Pat. Nos. 4,658,021, 4,665,160, 5,068, 317, 5,079,345, 5,424,199, 5,534,617, 5,597,709, 5,612,315, 5,633,352, 5,635,604, 5,688,666 and references cited therein).

The GHA proteins of the invention exhibit at least one biological function of GH. By "biological function" or "biological property" herein is meant any one of the properties or functions of GH, including, but not limited to, the ability to bind to a GH receptor; the ability to bind to a prolactin receptor; the ability to induce dimerization of a growth hormone receptor; the ability to induce dimerization of a prolactin receptor; the ability to bind to a cell comprising a growth hormone receptor, the ability to bind to a cell comprising a prolactin receptor; the ability to induce celiproliferation; the ability to show efficacy in the treatment of hypochondroplasia or idiopathic short structure; the ability to show efficacy in the treatment of Turner's syndrome; the ability to show efficacy in the treatment of growth delay in burned children; the ability to show efficacy in GH replacement therapies in GH deficient adults; the ability to show efficacy in the treatment of muscle wasting under conditions, including, but not limited to surgical stress, renal failure, muscular dystrophy, glucocorticoid administration or HIV infection; the ability to show efficacy in the treatment of congestive heart failure or in cardiovascular drug therapy; the ability to show efficacy in the treatment of bone diseases or osteoporosis; the ability to show efficacy in the treatment of disorders affecting puberty or reproduction; the ability to show efficacy in the GH therapy in elderly people; the ability to show efficacy in the treatment of wound healing, including but not limited to stasis ulcers, decubitus ulcers, or diabetic ulcers; the ability to show efficacy in the treatment of diffuse gastric bleeding; the ability to show efficacy in. the treatment of disorders relating to general anabolism, including, but not limited to pseudoarthrosis, burn therapy, old age cachetic states; the ability to show efficacy in the post-surgical (trauma) healing process; the ability to show efficacy in total parenteral nutrition (TPN); the ability to show efficacy in the treatment of breast cancer; the ability to show efficacy in the treatment of Prader-Willi syndrome; the ability to show efficacy in the reconstitution of the immune system; and the ability to show efficacy in the treatment of obesity; the ability to show efficacy in the treatment of Russell-Silver syndrome.

In one embodiment GHA proteins will exhibit at least 10% of the receptor binding or biological activity as the wild type GH. More preferred are GHA proteins that exhibit at least 50%, even more preferred are GHA proteins that exhibit at least 90%, and most preferred are GHA proteins that exhibit more than 100% of the receptor binding or biological activity as the wild type GH. Biological assays, including receptor binding assays are described in U.S. Pat. Nos. 4,658,021, 4,665,160, 5,068,317, 5,079,345, 5,424,199, 5,534,617, 5,597,709, 5,612,315, 5,633,352, 5,635,604, 5,688,666 and references cited therein, and Rowlinson et al. [J. Biol. Chem. 270(28):16833–16839 (1995); Endocrinology 137(1):90–5 (1996)], all of which are expressly incorporated by reference.

In one embodiment, at least one biological property of the GHA protein is altered when compared to the same property of HA. As outlined above, the invention provides GHA nucleic acids encoding GHA polypeptides. The GHA polypeptide preferably has at least one property, which is substantially different from the same property of the corresponding naturally occurring HA polypeptide. The property of the GHA polypeptide is the result the PDA analysis of the present invention.

The term "altered property" or grammatical equivalents thereof in the context of a polypeptide, as used herein, refer to any characteristic or attribute of a polypeptide that can be selected or detected and compared to the corresponding property of a naturally occurring protein. These properties include, but are not limited to oxidative stability, substrate specificity, catalytic activity, thermal stability, alkaline stability, pH activity profile, resistance to proteolytic degradation, Km, kcat, Km/kcat ratio, kinetic association ($K_{on}$) and dissociation ($K_{off}$) rate, protein folding, inducing an immune response, ability to bind to a ligand, ability to bind to a receptor, ability to be secreted, ability to be displayed on the surface of a cell, ability to oligomerize, ability to signal, ability to stimulate cell proliferation, ability to inhibit cell proliferation, ability to induce apoptosis, ability to be modified by phosphorylation or glycosylation, ability to treat disease.

Unless otherwise specified, a substantial change in any of the above-listed properties, when comparing the property of an GHA polypeptide to the property of a naturally occurring GH protein is preferably at least a 20%, more preferably, 50%, more preferably at least a 2-fold increase or decrease.

A change in oxidative stability is evidenced by at least about 20%, more preferably at least 50% increase of activity of a GHA protein when exposed to various oxidizing conditions as compared to that of a GH. Oxidative stability is measured by known procedures.

A change in alkaline stability is evidenced by at least about a 5% or greater increase or decrease (preferably increase) in the half life of the activity of a GHA protein when exposed to increasing or decreasing pH conditions as compared to that of a GH. Generally, alkaline stability is measured by known procedures.

A change in thermal stability is evidenced by at least about a 5% or greater increase or decrease (preferably increase) in the half life of the activity of a GHA protein when exposed to a relatively high temperature and neutral pH as compared to that of GH. Generally, thermal stability is measured by known procedures.

Similarly, GHA proteins, for example are experimentally tested and validated in in vivo and in in vitro assays. Suitable assays include, but are not limited to, e.g., examining their binding affinity to natural occurring or variant receptors and to high affinity agonists and/or antagonists. In addition to cell-free biochemical affinity tests, quantitative comparison are made comparing kinetic and equilibrium binding constants for the natural receptor to the naturally occurring GH and to the GHA proteins. The kinetic association rate ($K_{on}$) and dissociation rate ($K_{off}$), and the equilibrium binding constants ($K_d$) can be determined using surface plasmon resonance on a BIAcore instrument following the standard procedure in the literature [Pearce et al., Biochemistry 38:81–89 (1999)]. Comparing the binding constant between a natural receptor and its corresponding naturally occurring GH with the binding constant of a natural occurring receptor and an GHA protein are made in order to evaluate the sensitivity and specificity of the GHA protein. Preferably, binding affinity of the GHA protein to natural occurring receptors and variant receptors and agonists increases relative to the naturally occurring GH, while antagonist affinity decreases. GHA proteins with higher affinity to antagonists relative to the hGH may also be generated by the methods of the invention.

In a preferred embodiment, the biological function of a GHA protein is defined as the ability of the polypeptide of the invention to bind to a cell that comprises a growth hormone receptor or a prolactin receptor or any other receptor, to which the naturally occurring GH binds. GenBank accession numbers for GH binding receptors (GHR) are available for various species, e.g., human, A33991, S04530, P09587, P01242, CAA77872, CAA77877, CAA77876; pig, S12136; rat, I57940, A33505. Genbank accession numbers for prolactin receptor are available for several species, including human, A40144, NP_000940, P16471; mouse, I153269, I77525, I77524; rat, A41070, A36116, A29884; bovine, 14597, AAB97748, AAB97747; chicken, JQ1655; *Xenopus laevis,* BAA90400. Either of these receptors may be used in binding assays with a GHA protein. However, in some embodiments, GHA proteins may not possess this activity.

In a preferred embodiment, the assay system used to determine GHA is an in vitro system using cells that either express endogenous human growth hormone or human prolactin receptors or cells stably transfected with a gene encoding the human growth hormone receptor and/or the human prolactin receptor. In this system, cell proliferation is measured as a function of BrdU incorporation, which is incorporated into the nucleic acid of proliferating cells. A decrease above background of at least about 10%, with at least about 20% being preferred, with at least about 30% being more preferred and at least about 50%, 75% and 90% being especially preferred is an indication of GHA.

In a preferred embodiment, the antigenic profile in the host animal of the GHA protein is similar, and preferably identical, to the antigenic profile of the host GH; that is, the GHA protein does not significantly stimulate the host organism (e.g. the patient) to an immune response; that is, any immune response is not clinically relevant and there is no allergic response or neutralization of the protein by an antibody. That is, in a preferred embodiment, the GHA protein does not contain additional or different epitopes from the GH. By "epitope" or "determinant" herein is meant a portion of a protein which will generate and/or bind an antibody. Thus, in most instances, no significant amount of antibodies are generated to a GHA protein. In general, this is accomplished by not significantly altering surface residues, as outlined below nor by adding any amino acid residues on the surface which can become glycosylated, as novel glycosylation can result in an immune response.

The GHA proteins and nucleic acids of the invention are distinguishable from naturally occurring GHs. By "naturally occurring" or "wild type" or grammatical equivalents, herein is meant an amino acid sequence or a nucleotide sequence that is found in nature and includes allelic variations; that is, an amino acid sequence or a nucleotide sequence that usually has not been intentionally modified. Accordingly, by "non-naturally occurring", "synthetic", or "recombinant" or grammatical equivalents thereof, herein is meant an amino acid sequence or a nucleotide sequence that is not found in nature; that is, an amino acid sequence or a nucleotide sequence that usually has been intentionally modified. Representative amino acid and nucleotide sequences of a naturally occurring human growth hormone (hGH) are shown in FIGS. 1A–1C (SEQ ID NO:1, SEQ ID NO:14 and SEQ ID NO:2). It should be noted that unless otherwise stated, all positional numbering of GHA proteins and GHA nucleic acids is based on these sequences. That is, as will be appreciated by those in the art, an alignment of GH proteins and GHA proteins can be done using standard programs, as is outlined below, with the identification of "equivalent" positions between the two proteins. Thus, the GHA proteins and nucleic acids of the invention are non-naturally occurring; that is, they do not exist in nature.

Thus, in a preferred embodiment, the GHA protein has an amino acid sequence that differs from a wild-type GH sequence by at least 3% of the residues. That is, the GHA proteins of the invention are less than about 97% identical to a GH amino acid sequence. Accordingly, a protein is an "GHA protein" if the overall homology of the protein sequence to the amino acid sequence shown in FIG. 1A (SEQ ID NO:1) or FIG. 1B (SEQ ID NO:14) is preferably less than about 97%, more preferably less than about 95%, even more preferably less than about 90% and most preferably less than about 85%. In some embodiments the homology will be as low as about 75 to 80%. Stated differently, based on the sequence of the secreted, mature form of hGH, comprising 191 residues (residues 27 to 217 in FIG. 1A (SEQ ID NO:1)) of FIG. 1B (SEQ ID NO:14), GHA proteins have at least about 5–6 residues that differ from the hGH sequence (3%), with GHA proteins having from 5 residues to upwards of 40 residues being different from the hGH sequence. Preferred GHA proteins have 5–40 different residues with from about 5 to about 25 being preferred (that is, 3–13% of the protein is not identical to hGH), with from about 10 to 25 being particularly preferred (that is 6–13% of the protein is not identical to hGH).

In a preferred embodiment, the GHA proteins of the invention have 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 different residues from the hGH sequence.

Homology in this context means sequence similarity or identity, with identity being preferred. As is known in the art, a number of different programs can be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith & Waterman, Adv. Appl. Math., 2:482 (1981), by the sequence identity alignment algorithm of Needleman & Wunsch, J. Mol. Biol., 48:443 (1970), by the search for similarity method of Pearson & Lipman, Proc. Natl. Acad. Sci. U.S.A., 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res., 12:387–395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis, " Macromolecule Sequencing and Synthesis, Selected Methods and Applications, pp 127–149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351–360 (1987); the method is similar to that described by Higgins & Sharp CABIOS 5:151–153 (1989). Useful PILEUP parameters including a default gap weight of 3.00, a default gap length weight of 0.10, and weighted end gaps.

Another example of a useful algorithm is the BLAST algorithm, described in: Altschul et al., J. Mol. Biol. 215, 403–410, (1990); Altschul et al., Nucleic Acids Res. 25:3389–3402 (1997); and Karlin et al., Proc. Natl. Acad. Sci. U.S.A. 90:5873–5787 (1993). A particularly useful BLAST program is the WU-BLAST-2 program which was obtained from Altschul et al., Methods in Enzymology, 266:460–480 (1996); http://blast.wust/edu/blast/README.html]. WU-BLAST-2 uses several search parameters, most of which are set to the default values. The adjustable parameters are set with the following values: overlap span=1, overlap fraction=0.125, word threshold (T) =11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., Nucl. Acids Res., 25:3389–3402. Gapped BLAST uses BLOSUM-62 substitution scores; threshold T parameter set to 9; the two-hit method to trigger ungapped extensions; charges gap lengths of k a cost of 10+k; $X_u$ set to 16, and $X_g$ set to 40 for database search stage and to 67 for the output stage of the algorithms. Gapped alignments are triggered by a score corresponding to ~22 bits.

A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, "percent (%) nucleic acid sequence identity" with respect to the coding sequence of the polypeptides identified herein is defined as the percentage of nucleotide residues in a candidate sequence that are identical with the nucleotide residues in the coding sequence of the cell cycle protein. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer amino acids than the protein encoded by the sequence of FIG. 1C (SEQ ID NO:2), it is understood that in one embodiment, the percentage of sequence identity will be determined based on the number of identical amino acids in relation to the total number of amino acids. Thus, for example, sequence identity of sequences shorter than that shown in FIGS. 1A–1C (SEQ ID NO:1, SEQ ID NO:14, SEQ ID NO:2), as discussed below, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

Thus, GHA proteins of the present invention may be shorter or longer than the amino acid sequences shown in FIG. 1A (SEQ ID NO:1). Thus, in a preferred embodiment, included within the definition of GHA proteins are portions or fragments of the sequences depicted herein. Fragments of GHA proteins are considered GHA proteins if a) they share at least one antigenic epitope; b) have at least the indicated homology; c) and preferably have GHA biological activity as defined herein.

In a preferred embodiment, as is more fully outlined below, the GHA proteins include further amino acid variations, as compared to a wild type GH, than those outlined herein. In addition, as outlined herein, any of the variations depicted herein may be combined in any way to form additional novel GHA proteins.

In addition, GHA proteins can be made that are longer than those depicted in the figures, for example, by the addition of epitope or purification tags, as outlined herein, the addition of other fusion sequences, etc. For example, the GHA proteins of the invention may be fused to other therapeutic proteins such as IL-11 or to other proteins such as Fc or serum albumin for pharmacokinetic purposes. See for example U.S. Pat. Nos. 5,766,883 and 5,876,969, both of which are expressly incorporated by reference.

In a preferred embodiment, the GHA proteins comprise variable residues in core and boundary residues.

hGH core residues are as follows: positions 6, 10, 13, 17, 20, 24, 27, 28, 31, 36, 44, 54, 55, 58, 73, 75, 76, 78, 79, 80, 81, 82, 83, 85, 90, 93, 96, 97, 105, 110, 114, 117, 121, 124, 157, 161, 162, 163, 166, 170, 173, 176, 177, 180, and 184 (see FIGS. 3A and 4A). Accordingly, in a preferred embodiment, GHA proteins have variable positions selected from these positions.

In a preferred embodiment, GHA proteins have variable positions selected solely from core residues of hGH. Alternatively, at least a majority (51%) of the variable positions are selected from core residues, with at least about 75% of the variable positions being preferably selected from core residue positions, and at least about 90% of the variable positions being particularly preferred. A specifically preferred embodiment has only core variable positions altered as compared to hGH.

Particularly preferred embodiments where GHA proteins have variable core positions as compared to hGH are shown in FIGS. 4A–4E (SEQ ID NOS:36).

In one embodiment, the variable core positions are altered to any of the other 19 amino acids. In a preferred embodiment, the variable core residues are chosen from Ala, Val, Leu, Ile, Phe, Tyr, Trp, Met or Ser. In another preferred embodiment, the variable residues are chosen from Ala, Val, Leu, Ile, Phe, Tyr, Trp, Asp, Asn, Glu, Gln, Lys, Ser, Thr, Hsp (a positively charged histidine), Arg, Met, His, or Gly.

In a preferred embodiment, the GHA protein of the invention has a sequence that differs from a wild-type hGH in at least one amino acid position selected from positions 6, 7, 10, 13, 14, 17, 20, 24, 26, 27, 28, 29, 30, 31, 32, 34, 35, 36, 40, 43, 44, 50, 54, 55, 56, 57, 58, 59, 66, 70, 71. 73, 74, 75, 76, 77, 78, 79, 80, 81, 82, 83, 84, 85, 87, 90, 92, 93, 96, 97, 98, 100, 102, 104, 105, 106, 107, 109, 110, 111, 113, 114, 115, 117, 118, 121, 124, 125, 130, 132, 135, 137, 138, 139, 140, 141, 142, 143, 144, 145, 156, 157, 158, 159, 161, 162, 163, 166, 170, 173, 176, 177, 180, 183, 184, 185, and 188 (see also FIGS. 3 to 7, which outline sets of amino acid positions).

In another preferred embodiment, the GHA protein of the invention has a sequence that differs from a wild-type hGH in at least one amino acid position selected from positions 6, 10, 13, 17, 20, 24, 27, 28, 31, 36, 44, 54, 55, 58, 73, 75, 76, 78, 79, 80, 81, 82, 83, 85, 90, 93, 96, 97, 105, 110, 114, 117, 121, 124, 157, 161, 162, 163, 166, 170, 173, 176, 177, 180, and 184 (see also FIGS. 3A–D and 4A) which outline this set of amino acid positions).

In one aspect of this embodiment, preferred amino acid changes within the CORE region are as follows: 6LM; 6LV; A13V; A13I; A17M; L20M; T27V; Y28F; Y28L; F31W; F31I; F31M; F31L; F31Y; F31V; I36L; I36V; F54Y; S55A; I58V; I58L; L73M; L73A; L75M; L76M; I78F; I78M; I78V; I78L; S79A; S79V; L81I; L82I; L82M; L82V; I83L; I83V; S85A; V90I; V90M; F97L; V110M; V110L; V110I; L114M; L114F; L117M; L117A; I121V; I121M; I121L; G161M; G161L; G161F; L162V; L162 I; L162M; L163M; F166M; F166L; M170F; M170L; V173I; F176Y; L177I; and S184A (see FIG. 4A). These may be done either individually or in combination, with any combination possible. However, as outlined herein, preferred embodiments utilize at least five, and preferably more variable positions in each GHA protein.

In a particularly preferred embodiment, a preferred GHA protein comprises the following changes: A13V, T27V, Y28F, F54Y, S55A, S79A, S85A, V90I, L114M, G161M, and S184A (see FIG. 4B)(SEQ ID NO:3).

In one particularly preferred embodiment, a preferred GHA protein comprises the following changes: A13V, T27V, S79A, V90I, G161M, and S184A (see FIG. 4C)(SEQ ID NO:4).

In another particularly preferred embodiment, a preferred GHA protein comprises the following changes: A13V, T27V, S55A, S79A, S85A, V90I, G161M, and S184A (see FIG. 4D)(SEQ ID NO:5).

In a particularly preferred embodiment, a preferred GHA protein comprises the following changes: A13V, T27V, Y28F, F54Y, S55A, S79A, S85A, V90I, G161M, and S184A (see FIG. 4E)(SEQ ID NO:6).

In another preferred embodiment, the GHA protein of the invention has a sequence that differs from a wild-type hGH in at least one amino acid position selected from positions 6, 14, 26, 30, 32, 34, 35, 40, 50, 56, 57, 59, 66, 71, 74, 84, 92, 107, 109, 113, 118, 125, 130, 139, 143, 157, 158, and 183 (see also FIGS. 3 and 5A), which outline this set of amino acid positions).

In one aspect of this embodiment, preferred amino acid changes within the BOUNDARY1 region are as follows: L6I; L6E; M14L; M14I; D26R; D26A; D26K; D26L; D26M; E30W; E30F; E30V; A34K; A34H; A34W; Y35E;

Y35D; Q40K; Q40V; Q40R; Q40Y; Q40I; Q40L; Q40M; T50F; T50L; E56F; S57K; S57R; S57I; S57H; S57V; S57F; S57Y; S57A; S57L; S57Q; P59E; P59V; S71H; S71E; E74F; E74W; Q84R; Q84I; F92R; F92K; F92H; F92E; F92Y; F92V; F92L; D107A; D107V; D107E; N109F; N109R; N109L; N109I; N109V; N109K; N109M; L113F; E118L; M125I; M125V; D130R; D130V; D130H; D130Hsp; D130A; F139H; F139A; F139H; F139Hsp; F139E; Y143D; Y143A; L157R; L157M; L157V; L157H; K158F; K158E; K158L; K158V; R183H; R183K; R183F; and R183I (see FIG. 5A). These may be done either individually or in combination, with any combination possible. However, as outlined herein, preferred embodiments utilize at least five, and preferably more variable positions in each GHA protein.

In a particularly preferred embodiment, a preferred GHA protein comprises the following changes: M14L, D26A, E30V, A34W, Q40K, T50F, S57E, P59V, S71H, Q84R, F92E, D107A, N109F, E118L, M125I, D130R, F139H, Y143D, and R183H (see FIG. 5B)(SEQ ID NO:7).

In one particularly preferred embodiment, a preferred GHA protein comprises the following changes: M14L, D26A, E30W, A34K, Y35E, Q40K, T50F, S57K, P59E, S71H, Q84R, F92R, N109F, E118L, M125I, D130R, F139H, Y143D, K158F, and R183H (see FIG. 5C)(SEQ ID NO:8).

In one preferred embodiment, the GHA protein of the invention has a sequence that differs from a wild-type hGH in at least one amino acid position selected from positions 7, 29, 43, 70, 77, 87, 98, 100, 102, 104, 106, 111, 115, 132, 137, 140, 141, 142, 156, 159, 161, 184, 185, and 188 (see also FIGS. 3A–D and 6A), which outline this set of amino acid positions).

In one aspect of this embodiment, preferred amino acid changes within the BOUNDARY2 region are as follows: S7K; S7Y; S7R; S7F; S7L; S7V; Q29K; Q29I; Q29R; Q29V; S43K; S43R; S43W; S43I; S43V; S43H; S43M; S43L; S43F; K70L; K70M; K70R; R77M; R77L; R77V; L87I; L87M; L87V; L87Y; E98V; E98M; E98A; E98K; S100A; V102I; S106K; S106A; S106R; S106H; S106M; S106L; Y111R; Y111K; K115R; K115H; S132A; Q137W; Q137R; Q137A; Q141K; Q141F; T142V; L156M; L156I; L156V; L156W; L156K; L156R; L156T; L156Y; L156A; N159F; N159M; N159I; N159W; G161M; G161L; G161F; S184A; V185I; and S188A (see FIG. 6A). These may be done either individually or in combination, with any combination possible. However, as outlined herein, preferred embodiments utilize at least five, and preferably more variable positions in each GHA protein.

In a particularly preferred embodiment, a preferred GHA protein comprises the following changes: S7K, Q29K, S43K, R77M, A98V, S100A, S106K, Y111R, S132A, A137W, A141K, A142V, N159F, G161 M, S184A, and S188A (see FIG. 6B)(SEQ ID NO:9).

In another preferred embodiment, the GHA protein of the invention has a sequence that differs from a wild-type hGH in at least one amino acid position selected from positions 7, 14, 26, 29, 30, 34, 40, 43, 50, 57, 70, 77, 84, 87, 92, 98, 100, 102, 104, 106, 109, 111, 115, 118, 125, 132, 135, 137, 138, 140, 141, 142, 143, 144, 145, 147, 156, 159, 161, 184, 185, and 188 ( )(see also FIGS. 3A–D and 7A), which outline this set of amino acid positions).

In one aspect of this embodiment, preferred amino acid changes within the CLUSTERED BOUNDARY region are as follows: D26K; D26L; D26R; D26M; D26A; Q29I; Q29V; Q29L; Q29K; E30V; E30I; E30K; E30L; E30W; E30R; A34W; A34F; A34L; A34K; Q40V; Q40W; Q40I; Q40R; Q40K; Q40L; Q40Y; Q40M; Q40H; S43W; S43K; S43R; S43F; S43H; S43I; S43M; T50F; T50M; R77M; Q84M; Q84W; Q84V; F92V; F92Y; F92R; F92A; F92K; F92L; S100A; V102I; N1091; N109V; N109F; N109M; N109W; N109L; N109Y; N109A; N109K; N109R; Y111R; Y111K; E118M; E118F; E118K; E118L; M125I; M125V; S132A; Q137R; Q137F; Q137H; Q137Y; Q141F; T142V; T142K; T142Y; T142R; Y143V; Y143A; and K145A (see FIG. 7A). These may be done either individually or in combination, with any combination possible. However, as outlined herein, preferred embodiments utilize at least five, and preferably more variable positions in each GHA protein.

In a particularly preferred embodiment, a preferred GHA protein comprises the following changes: D26K, Q29I; E30V, A34W, Q40V, S43K, T50F, R77M, Q84M, F92V, S100A, V102I; N109F, Y111R, E118M, M125I; S132A, Q137R, Q141F, T142V, Y143V, and K145A (see FIG. 7B)(SEQ ID NO:10).

In one particularly preferred embodiment, a preferred GHA protein comprises the following changes: D26K, Q29I; E30V, A34W, Q40W, S43W, T50F, R77M, Q84M, F92V, S100A, V102I; N109F, Y111R, E118M, M125I; S132A, T135A, Q137R, I138A, Q141F, T142V, Y143V, S144A, K145A, and D147A (see FIG. 7C)(SEQ ID NO:11).

In another particularly preferred embodiment, a preferred GHA protein comprises the following changes: D26K, Q29I; E30V, A34W, Q40V, S43K, T50F, R77M, Q84M, F92V, S100A, V102I; N109F, Y111R, E118M, M125I; S132A, T135A, Q137R, I138A, Q141F, T142V, Y143V, S144A, K145A, and D147A (see FIG. 7D)(SEQ ID NO:12).

In a particularly preferred embodiment, a preferred GHA protein comprises the following changes: D26E, Q29K, E30V, A34W, Q40V, S43K, T50F, R77M, Q84M, F92V, S100A, N109F, Y111R, E118K, M125I; S132A, T135A, Q137R, I138A, Q141 F, T142V, Y143V, S144A, K145A and D147A (see FIG. 7E)(SEQ ID NO:13).

In a preferred embodiment, the GHA proteins of the invention are hGH conformers. By "conformer" herein is meant a protein that has a protein backbone 3D structure that is virtually the same but has significant differences in the amino acid side chains. That is, the GHA proteins of the invention define a conformer set, wherein all of the proteins of the set share a backbone structure and yet have sequences that differ by at least 3–5%. The three dimensional backbone structure of a GHA protein thus substantially corresponds to the three dimensional backbone structure of hGH. "Backbone" in this context means the non-side chain atoms: the nitrogen, carbonyl carbon and oxygen, and the α-carbon, and the hydrogens attached to the nitrogen and α-carbon. To be considered a conformer, a protein must have backbone atoms that are no more than 2 Å from the hGH structure, with no more than 1.5 Å being preferred, and no more than 1 Å being particularly preferred. In general, these distances may be determined in two ways. In one embodiment, each potential conformer is crystallized and its three dimensional structure determined. Alternatively, as the former is quite tedious, the sequence of each potential conformer is run in the PDA program to determine whether it is a conformer.

GHA proteins may also be identified as being encoded by GHA nucleic acids. In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence, with lower homology being preferred.

In a preferred embodiment, a GHA nucleic acid encodes a GHA protein. As will be appreciated by those in the art, due to the degeneracy of the genetic code, an extremely large number of nucleic acids may be made, all of which encode the GHA proteins of the present invention. Thus, having identified a particular amino acid sequence, those skilled in the art could make any number of different nucleic acids, by simply modifying the sequence of one or more codons in a way which does not change the amino acid sequence of the GHA.

In one embodiment, the nucleic acid homology is determined through hybridization studies. Thus, for example, nucleic acids which hybridize under high stringency to the nucleic acid sequence shown in FIG. 1C (SEQ ID NO:2) or its complement and encode a GHA protein is considered a GHA gene.

High stringency conditions are known in the art; see for example Sambrook et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5–10° C. lower than the thermal melting point ($T_m$) for the specific sequence at a defined ionic strength and pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

In another embodiment, less stringent hybridization conditions are used; for example, moderate or low stringency conditions may be used, as are known in the art; see Sambrook et al., supra; Ausubel, supra, and Tijssen, supra.

The GHA proteins and nucleic acids of the present invention are recombinant. As used herein, "nucleic add" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded or single stranded sequence. As will be appreciated by those in the art, the depiction of a single strand ("Watson") also defines the sequence of the other strand ("Crick"); thus the sequence depicted in FIG. 1C (SEQ ID NO:2) also includes the complement of the sequence. By the term "recombinant nucleic acid" herein is meant nucleic acid, originally formed in vitro, in general, by the manipulation of nucleic acid by endonucleases, in a form not normally found in nature. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purpose of the invention. Thus an isolated GHA nucleic acid, in a linear form, or an expression vector formed in vitro by ligating DNA molecules that are not normally joined, are both considered recombinant for the purposes of this invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a GHA protein from one organism in a different organism or host cell. Alternatively, the protein may be made at a significantly higher concentration than is normally seen, through the use of a inducible promoter or high expression promoter, such that the protein is made at increased concentration levels. Furthermore, all of the GHA proteins outlined herein are in a form not normally found in nature, as they contain amino acid substitutions, insertions and deletions, with substitutions being preferred, as discussed below.

Also included within the definition of GHA proteins of the present invention are amino acid sequence variants of the GHA sequences outlined herein and shown in the FIGS. That is, the GHA proteins may contain additional variable positions as compared to hGH. These variants fall into one or more of three classes: substitutional, insertional or deletional variants. These variants ordinarily are prepared by site specific mutagenesis of nucleotides in the DNA encoding a GHA protein, using cassette or PCR mutagenesis or other techniques well known in the art, to produce DNA encoding the variant, and thereafter expressing the DNA in recombinant cell culture as outlined above. However, variant GHA protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the GHA protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed GHA variants screened for the optimal combination of desired activity. Techniques for making substitution mutations at predetermined sites in DNA having a known sequence are well known, for example, M13 primer mutagenesis and PCR mutagenesis. Screening of the mutants is done using assays of GHA protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the GHA protein are desired, substitutions are generally made in accordance with the following chart:

CHART I

| Original Residue | Exemplary Substitutions |
|---|---|
| Ala | Ser |
| Arg | Lys |
| Asn | Gln, His |
| Asp | Glu |
| Cys | Ser, Ala |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the original GHA protein, although variants also are selected to modify the characteristics of the GHA proteins as needed. Alternatively, the variant may be designed such that the biological activity of the GHA protein is altered. For example, glycosylation sites may be altered or removed. Similarly, the biological function may be altered; for example, in some instances it may be desirable to have more or less potent hGH activity.

The GHA proteins and nucleic acids of the invention can be made in a number of ways. Individual nucleic acids and proteins can be made as known in the art and outlined below. Alternatively, libraries of GHA proteins can be made for testing.

In a preferred embodiment, sets or libraries of GHA proteins are generated from a probability distribution table. As outlined herein, there are a variety of methods of generating a probability distribution table, including using PDA, sequence alignments, forcefield calculations such as SCMF calculations, etc. In addition, the probability distribution can be used to generate information entropy scores for each position, as a measure of the mutational frequency observed in the library.

In this embodiment, the frequency of each amino acid residue at each variable position in the list is identified. Frequencies can be thresholded, wherein any variant frequency lower than a cutoff is set to zero. This cutoff is preferably 1%, 2%, 5%, 10% or 20%, with 10% being particularly preferred. These frequencies are then built into the GHA library. That is, as above, these variable positions are collected and all possible combinations are generated, but the amino acid residues that "fill" the library are utilized on a frequency basis. Thus, in a non-frequency based library, a variable position that has 5 possible residues will have 20% of the proteins comprising that variable position with the first possible residue, 20% with the second, etc. However, in a frequency based library, a variable position that has 5 possible residues with frequencies of 10%, 15%, 25%, 30% and 20%, respectively, will have 10% of the proteins comprising that variable position with the first possible residue, 15% of the proteins with the second residue, 25% with the third, etc. As will be appreciated by those in the art, the actual frequency may depend on the method used to actually generate the proteins; for example, exact frequencies may be possible when the proteins are synthesized. However, when the frequency-based primer system outlined below is used, the actual frequencies at each position will vary, as outlined below.

As will be appreciated by those in the art and outlined herein, probability distribution tables can be generated in a variety of ways. In addition to the methods outlined herein, self-consistent mean field (SCMF) methods can be used in the direct generation of probability tables. SCMF is a deterministic computational method that uses a mean field description of rotamer interactions to calculate energies. A probability table generated in this way can be used to create libraries as described herein. SCMF can be used in three ways: the frequencies of amino acids and rotamers for each amino acid are listed at each position; the probabilities are determined directly from SCMF (see Delarue et la. Pac. Symp. Biocomput. 109–21 (1997), expressly incorporated by reference). In addition, highly variable positions and non-variable positions can be identified. Alternatively, another method is used to determine what sequence is jumped to during a search of sequence space; SCMF is used to obtain an accurate energy for that sequence; this energy is then used to rank it and create a rank-ordered list of sequences (similar to a Monte Carlo sequence list). A probability table showing the frequencies of amino acids at each position can then be calculated from this list (Koehl et al., J. Mol. Biol. 239:249 (1994); Koehl et al., Nat. Struc. Biol. 2:163 (1995); Koehl et al., Curr. Opin. Struct. Biol. 6:222 (1996); Koehl et al., J. Mol. Bio. 293:1183 (1999); Koehl et al., J. Mol. Biol. 293:1161 (1999); Lee J. Mol. Biol. 236:918 (1994); and Vasquez Biopolymers 36:53–70 (1995); all of which are expressly incorporated by reference. Similar methods include, but are not limited to, OPLS-AA (Jorgensen, et al., J. Am. Chem. Soc. (1996), v 118, pp 11225–11236; Jorgensen, W. L.; BOSS, Version 4.1; Yale University: New Haven, Conn. (1999)); OPLS (Jorgensen, et al., J. Am. Chem. Soc. (1988), v 110, pp 1657ff;

Jorgensen, et al., J Am. Chem. Soc. (1990), v 112, pp 4768ff); UNRES (United Residue Forcefield; Liwo, et al., Protein Science (1993), v 2, pp1697–1714; Liwo, et al., Protein Science (1993), v 2, pp1715–1731; Liwo, et al., J. Comp. Chem. (1997), v 18, pp849–873; Liwo, et al., J. Comp. Chem. (1997), v 18, pp874–884; Liwo, et al., J. Comp. Chem. (1998), v 19, pp259–276; Forcefield for Protein Structure Prediction (Liwo, et al., Proc. Natl. Acad. Sci. USA (1999), v 96, pp5482–5485); ECEPP/3 (Liwo et al., J Protein Chem 1994 May;13(4):375–80); AMBER 1.1 force field (Weiner, et al., J. Am. Chem. Soc. v106, pp765–784); AMBER 3.0 force field (U.C. Singh et al., Proc. Natl. Acad. Sci. USA. 82:755–759); CHARMM and CHARMM22 (Brooks, et al., J. Comp. Chem. v4, pp 187–217); cvff3.0 (Dauber-Osguthorpe, et al., (1988) Proteins: Structure, Function and Genetics, v4, pp31–47); cff91 (Maple, et al., J. Comp. Chem. v15, 162–182); also, the DISCOVER (cvff and cff91) and AMBER forcefields are used in the INSIGHT molecular modeling package (Biosym/MSI, San Diego Calif.) and HARMM is used in the QUANTA molecular modeling package (Biosym/MSI, San Diego Calif.).

In addition, as outlined herein, a preferred method of generating a probability distribution table is through the use of sequence alignment programs. In addition, the probability table can be obtained by a combination of sequence alignments and computational approaches. For example, one can add amino acids found in the alignment of homologous sequences to the result of the computation. Preferable one can add the wild type amino acid identity to the probability table if it is not found in the computation.

As will be appreciated, a GHA protein library created by recombining variable positions and/or residues at the variable position may not be in a rank-ordered list. In some embodiments, the entire list may just be made and tested. Alternatively, in a preferred embodiment, the GHA protein library is also in the form of a rank ordered list This may be done for several reasons, including the size of the library is still too big to generate experimentally, or for predictive purposes. This may be done in several ways. In one embodiment, the library is ranked using the scoring functions of PDA to rank the library members. Alternatively, statistical methods could be used. For example, the library may be ranked by frequency score; that is, proteins containing the most of high frequency residues could be ranked higher, etc. This may be done by adding or multiplying the frequency at each variable position to generate a numerical score. Similarly, the library different positions could be weighted and then the proteins scored; for example, those containing certain residues could be arbitrarily ranked.

In a preferred embodiment, the different protein members of the GHA protein library may be chemically synthesized. This is particularly useful when the designed proteins are short, preferably less than 150 amino acids in length, with less than 100 amino acids being preferred, and less than 50 amino acids being particularly preferred, although as is known in the art, longer proteins can be made chemically or enzymatically. See for example Wilken et al, Curr. Opin. Biotechnol. 9:412–26 (1998), hereby expressly incorporated by reference.

In a preferred embodiment, particularly for longer proteins or proteins for which large samples are desired, the library sequences are used to create nucleic acids such as DNA which encode the member sequences and which can then be cloned into host cells, expressed and assayed, if desired. Thus, nucleic acids, and particularly DNA, can be made which encodes each member protein sequence. This is done using well known procedures. The choice of codons, suitable expression vectors and suitable host cells will vary depending on a number of factors, and can be easily optimized as needed.

In a preferred embodiment, multiple PCR reactions with pooled oligonucleotides is done, as is generally depicted in FIG. 8. In this embodiment, overlapping oligonucleotides are synthesized which correspond to the full length gene. Again, these oligonucleotides may represent all of the different amino acids at each variant position or subsets.

In a preferred embodiment, these oligonucleotides are pooled in equal proportions and multiple PCR reactions are performed to create full length sequences containing the combinations of mutations defined by the library. In addition, this may be done using error-prone PCR methods.

In a preferred embodiment, the different oligonucleotides are added in relative amounts corresponding to the probability distribution table. The multiple PCR reactions thus result in full length sequences with the desired combinations of mutations in the desired proportions.

The total number of oligonucleotides needed is a function of the number of positions being mutated and the number of mutations being considered at these positions.

(number of oligos for constant positions)+M1+M2+M3+ ... Mn=(total number of oligos required), where Mn is the number of mutations considered at position n in the sequence.

In a preferred embodiment, each overlapping oligonucleotide comprises only one position to be varied; in alternate embodiments, the variant positions are too close together to allow this and multiple variants per oligonucleotide are used to allow complete recombination of all the possibilities. That is, each oligo can contain the codon for a single position being mutated, or for more than one position being mutated. The multiple positions being mutated must be close in sequence to prevent the oligo length from being impractical. For multiple mutating positions on an oligonucleotide, particular combinations of mutations can be included or excluded in the library by including or excluding the oligonucleotide encoding that combination. For example, as discussed herein, there may be correlations between variable regions; that is, when position X is a certain residue, position Y must (or must not) be a particular residue. These sets of variable positions are sometimes referred to herein as a "cluster". When the clusters are comprised of residues close together, and thus can reside on one oligonucleotide primer, the clusters can be set to the "good" correlations, and eliminate the bad combinations that may decrease the effectiveness of the library. However, if the residues of the cluster are far apart in sequence, and thus will reside on different oligonucleotides for synthesis, it may be desirable to either set the residues to the "good" correlation, or eliminate them as variable residues entirely. In an alternative embodiment, the library may be generated in several steps, so that the cluster mutations only appear together. This procedure, i.e. the procedure of identifying mutation clusters and either placing them on the same oligonucleotides or eliminating them from the library or library generation in several steps preserving clusters, can considerably enrich the experimental library with properly folded protein. Identification of clusters can be carried out by a number of ways, e.g. by using known pattern recognition methods, comparisons of frequencies of occurence of mutations or by using energy analysis of the sequences to be experimentally generated (for example, if the energy of interaction is high, the positions are correlated). These correlations may be positional correlations (e.g. variable positions 1 and 2 always change together or never change together) or sequence correlations (e.g. if there is residue A at position 1, there is always residue B at position 2). See: Pattern discovery in Biomolecular Data: Tools, Techniques, and Applications; edited by Jason T. L. Wang, Bruce A. Shapiro, Dennis Shasha. New York: Oxford University, 1999; Andrews, Harry C. Introduction to mathematical techniques in pattern recognition; New York, Wiley-lnterscience [1972]; Applications of Pattern Recognition; Editor, K. S. Fu. Boca Raton, Fla. CRC Press, 1982; Genetic Algorithms for Pattern Recognition; edited by Sankar K. Pal, Paul P. Wang. Boca Raton: CRC Press, c1996; Pandya, Abhijit S., Pattern recognition with neural networks in C++/Abhijit S. Pandya, Robert B. Macy. Boca Raton, Fla.: CRC Press, 1996; Handbook of pattern recognition & computer vision/edited by C. H. Chen, L. F. Pau, P. S. P. Wang, 2nd ed. Singapore; River Edge, N.J.: World Scientific, c1999; Friedman, Introduction to Pattern Recognition: Statistical, Structural, Neural, and Fuzy Logic Approaches; River Edge, N.J.: World Scientific, c1999, Series title: Series in machine perception and artificial intelligence; vol. 32; all of which are expressly incorporated by reference. In addition, programs used to search for consensus motifs can be used as well.

In addition, correlations and shuffling can be fixed or optimized by altering the design of the oligonucleotides: that is, by deciding where the oligonucleotides (primers) start and stop (e.g. where the sequences are "cut"). The start and stop sites of oligos can be set to maximize the number of clusters that appear in single oligonucleotides, thereby enriching the library with higher scoring sequences. Different oligonucleotide start and stop site options can be computationally modeled and ranked according to number of clusters that are represented on single oligos, or the percentage of the resulting sequences consistent with the predicted library of sequences.

The total number of oligonucleotides required increases when multiple mutable positions are encoded by a single oligonucleotide. The annealed regions are the ones that remain constant, i.e. have the sequence of the reference sequence.

Oligonucleotides with insertions or deletions of codons can be used to create a library expressing different length proteins. In particular computational sequence screening for insertions or deletions can result in secondary libraries defining different length proteins, which can be expressed by a library of pooled oligonucleotide of different lengths.

In a preferred embodiment, the GHA library is done by shuffling the family (e.g. a set of variants); that is, some set of the top sequences (if a rank-ordered list is used) can be shuffled, either with or without error-prone PCR. "Shuffling" in this context means a recombination of related sequences, generally in a random way. It can include "shuffling" as defined and exemplified in U.S. Pat. Nos. 5,830,721; 5,811, 238; 5,605,793; 5,837,458 and PCT US/19256, all of which are expressly incorporated by reference in their entirety. This set of sequences can also be an artificial set; for example, from a probability table (for example generated using SCMF) or a Monte Carlo set. Similarly, the "family" can be the top 10 and the bottom 10 sequences, the top 100 sequence, etc. This may also be done using error-prone PCR.

Thus, in a preferred embodiment, in silico shuffling is done using the computational methods described herein. That is, starting with either two libraries or two sequences, random recombinations of the sequences can be generated and evaluated.

In a preferred embodiment, error-prone PCR is done to generate the GHA library. See U.S. Pat. Nos. 5,605,793, 5,811,238, and 5,830,721, all of which are hereby incorporated by reference. This can be done on the optimal sequence or on top members of the library, or some other artificial set or family. In this embodiment, the gene for the optimal sequence found in the computational screen of the primary library can be synthesized. Error prone PCR is then performed on the optimal sequence gene in the presence of oligonucleotides that code for the mutations at the variant positions of the library (bias oligonucleotides). The addition of the oligonucleotides will create a bias favoring the incorporation of the mutations in the library. Alternatively, only oligonucleotides for certain mutations may be used to bias the library.

In a preferred embodiment, gene shuffling with error prone PCR can be performed on the gene for the optimal sequence, in the presence of bias oligonucleotides, to create a DNA sequence library that reflects the proportion of the mutations found in the GHA library. The choice of the bias oligonucleotides can be done in a variety of ways; they can chosen on the basis of their frequency, i.e. oligonucleotides encoding high mutational frequency positions can be used; alternatively, oligonucleotides containing the most variable positions can be used, such that the diversity is increased; if the secondary library is ranked, some number of top scoring positions can be used to generate bias oligonucleotides; random positions may be chosen; a few top scoring and a few low scoring ones may be chosen; etc. What is important is to generate new sequences based on preferred variable positions and sequences.

In a preferred embodiment, PCR using a wild type gene or other gene can be used, as is schematically depicted in FIG. 9. In this embodiment, a starting gene is used; generally, although this is not required, the gene is usually the wild type gene. In some cases it may be the gene encoding the global optimized sequence, or any other sequence of the list, or a consensus sequence obtained e.g. from aligning homologous sequences from different organisms. In this embodiment, oligonucleotides are used that correspond to the variant positions and contain the different amino acids of the library. PCR is done using PCR primers at the termini, as is known in the art. This provides two benefits; the first is that this generally requires fewer oligonucleotides and can result in fewer errors. In addition, it has experimental advantages in that if the wild type gene is used, it need not be synthesized.

In addition, there are several other techniques that can be used, as exemplified in FIGS. 9 to 12. In a preferred embodiment, ligation of PCR products is done.

In a preferred embodiment, a variety of additional steps may be done to the GHA protein library; for example, further computational processing can occur, different GHA protein libraries can be recombined, or cutoffs from different libraries can be combined. In a preferred embodiment, an GHA library may be computationally remanipulated to form an additional GHA protein library (sometimes referred to herein as "tertiary libraries"). For example, any of the GHA protein library sequences may be chosen for a second round of PDA, by freezing or fixing some or all of the changed positions in the first library. Alternatively, only changes seen in the last probability distribution table are allowed. Alternatively, the stringency of the probability table may be altered, either by increasing or decreasing the cutoff for inclusion. Similarly, the GHA protein library may be recombined experimentally after the first round; for example, the best gene/genes from the first screen may be taken and gene assembly redone (using techniques outlined below, multiple PCR, error prone PCR, shuffling, etc.). Alternatively, the fragments from one or more good gene(s) to change probabilities at some positions. This biases the search to an area of sequence space found in the first round of computational and experimental screening.

In a preferred embodiment, a tertiary library can be generated from combining different GHA protein libraries. For example, a probability distribution table from a first GHA protein library can be generated and recombined, either computationally or experimentally, as outlined herein. A PDA GHA protein library may be combined with a sequence alignment GHA protein library, and either recombined (again, computationally or experimentally) or just the cutoffs from each joined to make a new tertiary library. The top sequences from several libraries can be recombined. Sequences from the top of a library can be combined with sequences from the bottom of the library to more broadly sample sequence space, or only sequences distant from the top of the library can be combined. GHA protein libraries that analyzed different parts of a protein can be combined to a tertiary library that treats the combined parts of the protein.

In a preferred embodiment, a tertiary library can be generated using correlations in a GHA protein library. That is, a residue at a first variable position may be correlated to a residue at second variable position (or correlated to residues at additional positions as well). For example, two variable positions may sterically or electrostatically interact, such that if the first residue is X, the second residue must be Y. This may be either a positive or negative correlation.

Using the nucleic acids of the present invention which encode a GHA protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the GHA protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation.

In a preferred embodiment, when the endogenous secretory sequence leads to a low level of secretion of the naturally occurring protein or of the GHA protein, a replacement of the naturally occurring secretory leader sequence is desired. In this embodiment, an unrelated secretory leader sequence is operably linked to a GHA protein encoding nucleic acid leading to increased protein secretion. Thus, any secretory leader sequence resulting in enhanced secretion of the GHA protein, when compared to the secretion of hGH and its secretory sequence, is desired. Suitable secretory leader sequences that lead to the secretion of a protein are know in the art.

In another preferred embodiment, a secretory leader sequence of a naturally occurring protein or a protein is removed by techniques known in the art and subsequent expression results in intracellular accumulation of the recombinant protein.

Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the fusion protein; for example, transcriptional and translational regulatory nucleic acid sequences from *Bacillus* are preferably used to express the fusion protein in *Bacillus*. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention. In a preferred embodiment, the promoters are strong promoters, allowing high expression in cells, particularly mammalian cells, such as the CMV promoter, particularly in combination with a Tet regulatory element.

In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

A preferred expression vector system is a retroviral vector system such as is generally described in PCT/US97/01019 and PCT/US97/01048, both of which are hereby expressly incorporated by reference.

The GHA nucleic acids are introduced into the cells either alone or in combination with an expression vector. By "introduced into" or grammatical equivalents herein is meant that the nucleic acids enter the cells in a manner suitable for subsequent expression of the nucleic acid. The method of introduction is largely dictated by the targeted cell type, discussed below. Exemplary methods include $CaPO_4$ precipitation, liposome fusion, lipofectin®, electroporation, viral infection, etc. The GHA nucleic acids may stably integrate into the genome of the host cell (for example, with retroviral introduction, outlined below), or may exist either transiently or stably in the cytoplasm (i.e. through the use of traditional plasmids, utilizing standard regulatory sequences, selection markers, etc.).

The GHA proteins of the present invention are produced by culturing a host cell transformed with an expression vector containing nucleic acid encoding a GHA A protein, under the appropriate conditions to induce or cause expression of the GHA protein. The conditions appropriate for GHA protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melangaster* cells, *Saccharomyces cerevisiae* and other yeasts, *E. coli, Bacillus subtilis,* SF9 cells, C129 cells, 293 cells, Neurospora, BHK, CHO, COS, *Pichia Pastoris,* etc.

In a preferred embodiment, the GHA proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for the fusion protein into mRNA. A promoter will have a transcription initiating region, which is usually placed proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei. As outlined herein, a particularly preferred method utilizes retroviral infection, as outlined in PCT US97/01019, incorporated by reference.

As will be appreciated by those in the art, the type of mammalian cells used in the present invention can vary widely. Basically, any mammalian cells may be used, with mouse, rat, primate and human cells being particularly preferred, although as will be appreciated by those in the art, modifications of the system by pseudotyping allows all eukaryotic cells to be used, preferably higher eukaryotes. As is more fully described below, a screen will be set up such that the cells exhibit a selectable phenotype in the presence of a bioactive peptide. As is more fully described below, cell types implicated in a wide variety of disease conditions are particularly useful, so long as a suitable screen may be designed to allow the selection of cells that exhibit an altered phenotype as a consequence of the presence of a peptide within the cell.

Accordingly, suitable cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, Cos, etc. See the ATCC cell line catalog, hereby expressly incorporated by reference.

In one embodiment, the cells may be additionally genetically engineered, that is, contain exogenous nucleic acid other than the GHA nucleic acid.

In a preferred embodiment, the GHA proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of the GHA protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli,* the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the GHA protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria). For expression in bacteria, usually bacterial secretory leader sequences, operably linked to a GHA protein encoding nucleic acid, are preferred.

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris,* and *Streptococcus lividans,* among others.

The bacterial expression vectors are transformed into bacterial host cells using techniques well known in the art, such as calcium chloride treatment, electroporation, and others.

In one embodiment, GHA proteins are produced in insect cells. Expression vectors for the transformation of insect cells, and in particular, baculovirus-based expression vectors, are well known in the art.

In a preferred embodiment, GHA proteins are produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe,* and *Yarrowia lipolytica.* Preferred promoter sequences for expression in yeast include the inducible GAL1, 10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

In addition, the GHA polypeptides of the invention may be further fused to other proteins, if desired, for example to increase expression or stabilize the protein.

In one embodiment, the GHA nucleic acids, proteins and antibodies of the invention are labeled with a label other than the scaffold. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

Once made, the GHA proteins may be covalently modified. One type of covalent modification includes reacting targeted amino acid residues of a GHA polypeptide with an organic derivatizing agent that is capable of reacting with selected side chains or the N- or C-terminal residues of a GHA polypeptide. Derivatization with bifunctional agents is useful, for instance, for crosslinking a GHA protein to a water-insoluble support matrix or surface for use in the method for purifying anti-GHA antibodies or screening assays, as is more fully described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the "-amino groups of lysine, arginine, and histidine side chains [T. E. Creighton, Proteins: Structure and Molecular Properties, W.H. Freeman & Co., San Francisco, pp. 79–86 (1983)], acetylation of the N-terminal amine, and amidation of any C-terminal carboxyl group.

Another type of covalent modification of the GHA polypeptide included within the scope of this invention comprises altering the native glycosylation pattern of the polypeptide. "Altering the native glycosylation pattern" is intended for purposes herein to mean deleting one or more carbohydrate moieties found in native sequence GHA polypeptide, and/or adding one or more glycosylation sites that are not present in the native sequence GHA polypeptide.

Addition of glycosylation sites to GHA polypeptides may be accomplished by altering the amino acid sequence thereof. The alteration may be made for example, by the addition of, or substitution by, one or more serine or threonine residues to the native sequence GHA polypeptide (for O-linked glycosylation sites). The GHA amino acid sequence may optionally be altered through changes at the DNA level, particularly by mutating the DNA encoding the GHA polypeptide at preselected bases such that codons are generated that will translate into the desired amino acids.

Another means of increasing the number of carbohydrate moieties on the GHA polypeptide is by chemical or enzymatic coupling of glycosides to the polypeptide. Such methods are described in the art, e.g., in WO 87/05330 published 11 Sep. 1987, and in Aplin and Wriston, CRC Crit. Rev. Biochem., pp 259–306 (1981).

Removal of carbohydrate moieties present on the GHA polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo- and exo-glycosidases as described by Thotakura et al., Meth. Enzymol., 138:350 (1987).

Such derivatized moieties may improve the solubility, absorption, permeability across the blood brain barrier biological half life, and the like. Such moieties or modifications of GHA polypeptides may alternatively eliminate or attenuate any possible undesirable side effect of the protein and the like. Moieties capable of mediating such effects are disclosed, for example, in Remington's Pharmaceutical Sciences, 16th ed., Mack Publishing Co., Easton, Pa. (1980).

Another type of covalent modification of GHA polypeptides comprises linking the GHA polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

GHA polypeptides of the present invention may also be modified in a way to form chimeric molecules comprising a GHA polypeptide fused to another, heterologous polypeptide or amino acid sequence. In one embodiment, such a chimeric molecule comprises a fusion of a GHA polypeptide with a tag polypeptide which provides an epitope to which an anti-tag antibody can selectively bind. The epitope tag is generally placed at the amino-or carboxyl-terminus of the GHA polypeptide. The presence of such epitope-tagged forms of a GHA polypeptide can be detected using an antibody against the tag polypeptide. Also, provision of the epitope tag enables the GHA polypeptide to be readily purified by affinity purification using an anti-tag antibody or another type of affinity matrix that binds to the epitope tag. In an alternative embodiment, the chimeric molecule may comprise a fusion of a GHA polypeptide with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol. 8:2159–2165 (1988)]; the c-myc tag and the 8F9, 3C7, 6E10, G4, B7 and 9E10 antibodies thereto [Evan et al., Molecular and Cellular Biology, 5:3610–3616 (1985)]; and the Herpes Simplex virus glycoprotein D (gD) tag and its antibody [Paborsky et al., Protein Engineering, 3(6):547–553 (1990)]. Other tag polypeptides include the Flag-peptide [Hopp et al., BioTechnology 6:1204–1210 (1988)]; the KT3 epitope peptide [Martin et al., Science 255:192–194 (1992)]; tubulin epitopepeptide [Skinner et al., J. Biol. Chem. 266:15163–15166 (1991)]; and the T7 gene 10 protein peptide tag [Lutz-Freyermuth et al., Proc. Natl. Acad. Sci. U.S.A. 87:6393–6397 (1990)].

In a preferred embodiment, the GHA protein is purified or isolated after expression. GHA proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the GHA protein may be purified using a standard anti-library antibody column. Ultrafiltration and diafiltration techniques, in conjunction with protein concentration, are also useful. For general guidance in suitable purification techniques, see Scopes, R., Protein Purification, Springer-Verlag, N.Y. (1982). The degree of purification necessary will vary depending on the use of the GHA protein. In some instances no purification will be necessary.

Once made, the GHA proteins and nucleic acids of the invention find use in a number of applications. In a preferred embodiment, the GHA proteins are administered to a patient to treat an hGH-associated disorder.

By "GH-associated disorder" or "GH responsive disorder" or condition" herein is meant a disorder that can be ameliorated by the administration of a pharmaceutical composition comprising a GHA protein, including, but not limited to, dwarfism or growth delay, hypochondroplasia or idiopathic short structure; Turner's syndrome; growth delay in burned children; muscle wasting under conditions, including, but not limited to surgical stress, renal failure, muscular dystrophy, glucocorticoid administration or HIV infection; congestive heart failure or cardiovascular drug therapy; bone diseases or osteoporosis; disorders affecting puberty or reproduction; diffuse gastric bleeding; disorders relating to general anabolism, including, but not limited to pseudoarthrosis, burn therapy, old age cachetic states; breast cancer; Prader-Willi syndrome; obesity; and Russel-Silver syndrome. Included within this definition is the use of a GHA protein in GH replacement therapies in GH deficient adults; GH therapy in elderly people; wound healing, including but not limited to stasis ulcers, decubitus ulcers, or diabetic ulcers; post-surgical (trauma) healing process; total parenteral nutrition (TPN); and the reconstitution of the immune system.

In a preferred embodiment, a therapeutically effective dose of a GHA protein is administered to a patient in need of treatment. By "therapeutically effective dose" herein is meant a dose that produces the effects for which it is administered. The exact dose will depend on the purpose of the treatment, and will be ascertainable by one skilled in the art using known techniques. In a preferred embodiment, dosages of about 5 $\mu$g/kg are used, administered either intraveneously or subcutaneously. As is known in the art, adjustments for GHA protein degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals, and organisms. Thus the methods are applicable to both human therapy and veterinary applications. In the preferred embodiment the patient is a mammal, and in the most preferred embodiment the patient is human.

The term "treatment" in the instant invention is meant to include therapeutic treatment, as well as prophylactic, or suppressive measures for the disease or disorder. Thus, for example, in the case of GH therapy in elderly people, successful administration of a GHA protein prior to onset of the disease or symptoms of a disease results in "treatment" of the disease. As another example, successful administration of a GHA protein after clinical manifestation of the disease to combat the symptoms of the disease comprises "treatment" of the disease. "Treatment" also encompasses administration of a GHA protein after the appearance of the disease in order to eradicate the disease. Successful administration of an agent after onset and after clinical symptoms have developed, with possible abatement of clinical symptoms and perhaps amelioration of the disease, comprises "treatment" of the disease.

Those "in need of treatment" include mammals already having the disease or disorder, as well as those prone to having the disease or disorder, including those in which the disease or disorder is to be prevented.

In another embodiment, a therapeutically effective dose of a GHA protein, a GHA gene, or a GHA antibody is administered to a patient having a disease involving inappropriate expression of GH. A "disease involving inappropriate expression of GH" within the scope of the present invention is meant to include diseases or disorders characterized by an overabundance of GH. This overabundance may be due to any cause, including, but not limited to, overexpression at the molecular level, prolonged or accumulated appearance at the site of action, or increased activity of GH relative to normal. Included within this definition are diseases or disorders characterized by a reduction of GH. This reduction may be due to any cause, including, but not limited to, reduced expression at the molecular level, shortened or reduced appearance at the site of action, or decreased activity of GH relative to normal. Such an overabundance or reduction of GH can be measured relative to normal expression, appearance, or activity of GH according to, but not limited to, the assays described and referenced herein.

The administration of the GHA proteins of the present invention, preferably in the form of a sterile aqueous solution, can be done in a variety of ways, including, but not limited to, orally, subcutaneously, intravenously, intranasally, transdermally, intraperitoneally, intramuscularly, intrapulmonary, vaginally, rectally, or intraccularly. In some instances, for example, in the treatment of wounds, inflammation, or multiple sclerosis, the GHA A protein may be directly applied as a solution or spray. Depending upon the manner of introduction, the pharmaceutical composition may be formulated in a variety of ways. The concentration of the therapeutically active GHA protein in the formulation may vary from about 0.1 to 100 weight %. In another preferred embodiment, the concentration of the GHA protein is in the range of 0.003 to 1.0 molar, with dosages from 0.03, 0.05, 0.1, 0.2, and 0.3 millimoles per kilogram of body weight being preferred.

The pharmaceutical compositions of the present invention comprise a GHA protein in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers such as NaOAc; fillers such as microcrystalline cellulose, lactose, corn and other starches; binding agents; sweeteners and other flavoring agents, coloring agents; and polyethylene glycol. Additives are well known in the art, and are used in a variety of formulations.

In addition, in one embodiment, the GHA proteins of the present invention are formulated using a process for pharmaceutical compositions of recombinant GH as described in U.S. Pat. No. 5,612,315 which, hereby, is expressly incorporated in its entirety.

In a further embodiment, the GHA proteins are added in a micellular formulation; see U.S. Pat. No. 5,833,948, hereby expressly incorporated by reference in its entirety.

Combinations of pharmaceutical compositions may be administered. Moreover, the compositions may be administered in combination with other therapeutics.

In one embodiment provided herein, antibodies, including but not limited to monoclonal and polyclonal antibodies, are raised against GHA proteins using methods known in the art.

In a preferred embodiment, these anti-GHA antibodies are used for immunotherapy. Thus, methods of immunotherapy are provided. By "immunotherapy" is meant treatment of a GH related disorders with an antibody raised against a GHA protein. As used herein, immunotherapy can be passive or active. Passive immunotherapy, as defined herein, is the passive transfer of antibody to a recipient (patient). Active immunization is the induction of antibody and/or T-cell responses in a recipient (patient). Induction of an immune response can be the consequence of providing the recipient with a GHA protein antigen to which antibodies are raised. As appreciated by one of ordinary skill in the art, the GHA protein antigen may be provided by injecting a GHA polypeptide against which antibodies are desired to be raised into a recipient, or contacting the recipient with a GHA protein encoding nucleic acid, capable of expressing the GHA protein antigen, under conditions for expression of the GHA protein antigen.

In another preferred embodiment, a therapeutic compound is conjugated to an antibody, preferably an anti-GHA protein antibody. The therapeutic compound may be a cytotoxic agent. In this method, targeting the cytotoxic agent to tumor tissue or cells, results in a reduction in the number of afflicted cells, thereby reducing symptoms associated with cancer, and GHA protein related disorders. Cytotoxic agents are numerous and varied and include, but are not limited to, cytotoxic drugs or toxins or active fragments of such toxins. Suitable toxins and their corresponding fragments include diptheria A chain, exotoxin A chain, ricin A chain, abrin A chain, curcin, crotin, phenomycin, enomycin and the like. Cytotoxic agents also include radiochemicals made by conjugating radioisotopes to antibodies raised against cell cycle proteins, or binding of a radionuclide to a chelating agent that has been covalently attached to the antibody.

In a preferred embodiment, GHA proteins are administered as therapeutic agents, and can be formulated as outlined above. Similarly, GHA genes (including both the full-length sequence, partial sequences, or regulatory sequences of the GHA coding regions) can be administered in gene therapy applications, as is known in the art. These GHA genes can include antisense applications, either as gene therapy (i.e. for incorporation into the genome) or as antisense compositions, as will be appreciated by those in the art.

In a preferred embodiment, the nucleic acid encoding the GHA proteins may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. [Zamecnik et al., Proc. Nati. Acad. Sci. U.S.A. 83:4143–4146 (1986)]. The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection [Dzau et al., Trends in Biotechnology 11:205–210 (1993)]. In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262:4429–4432 (1987); and Wagner et al., Proc. Natl. Acad. Sci. U.S.A. 87:3410–3414 (1990). For review of gene marking and gene therapy protocols see Anderson et al., Science 256:808–813 (1992).

In a preferred embodiment, GHA genes are administered as DNA vaccines, either single genes or combinations of GHA genes. Naked DNA vaccines are generally known in the art Brower, Nature Biotechnology, 16:1304–1305 (1998). Methods for the use of genes as DNA vaccines are well known to one of ordinary skill in the art, and include placing a GHA gene or portion of a GHA gene under the control of a promoter for expression in a patient in need of treatment. The GHA gene used for DNA vaccines can encode full-length GHA proteins, but more preferably encodes portions of the GHA proteins including peptides derived from the GHA protein. In a preferred embodiment a patient is immunized with a DNA vaccine comprising a plurality of nucleotide sequences derived from a GHA gene. Similarly, it is possible to immunize a patient with a plurality of GHA genes or portions thereof as defined herein. Without being bound by theory, expression of the polypeptide encoded by the DNA vaccine, cytotoxic T-cells, helper T-cells and antibodies are induced which recognize and destroy or eliminate cells expressing GH proteins.

In a preferred embodiment, the DNA vaccines include a gene encoding an adjuvant molecule with the DNA vaccine. Such adjuvant molecules include cytokines that increase the immunogenic response to the GHA polypeptide encoded by the DNA vaccine. Additional or alternative adjuvants are known to those of ordinary skill in the art and find use in the invention.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXAMPLE 1

Design and Characterization of Novel GHA Protiens by PDA

Summary: Sequences for novel growth hormone activity proteins (GHA proteins) were designed by optimizing residues in four regions of the protein (CORE, BOUNDARY 1, BOUNDARY 2 and CLUSTERED BOUNDARY) using Protein Design Automation (PDA) as described in WO98/47089, U.S. Ser. Nos. 09/058,459, 09/127,926, 60/104,612, 60/158,700, 09/419,351, 60/181,630, 60/186,904, and U.S. patent application, entitled Protein Design Automation For Protein Libraries (Filed: Apr. 14, 2000; Inventor: Bassil Dahiyat), and PCT US98/07254, all of which are expressly incorporated by reference in their entirety. Several core designs were completed, with 21–45 residues considered corresponding to $21^{20}$–$45^{20}$ sequence possibilities. Residues unexposed to solvent were designed in order to minimize changes to the molecular surface and to limit the potential for antigenicity of designed novel protein analogues.

Calculations required from 12–24 hours on 16 Silicon Graphics R10000 CPU's. The global optimum sequence from each design was selected for characterization. The examples herein describe GHA proteins that have from 6–26 amino acid substitutions when compared to the amino acid sequence of the mature hGH (190 amino acid residues)(SEQ ID NO:14).

Computational Protocols

Template Structure Preparation:

The template structure was produced using homology modeling. For this study the crystal structure of human growth hormone as deposited in the Brookhaven Protein Data Bank was used [PDB record 3HHR; de Vos et al., Science 255(5042):306–12(1992)]. After removing all water and receptor molecules and adding all hydrogen atoms to the protein, this resulting structure was minimized for 50 steps with conjugate gradient method with Dreiding forcefield. Electrostatic forces were turned off. PDA was then used to redesign four regions of the protein (CORE, BOUNDARY1, BOUNDARY2 and CLUSTERED BOUNDARY) with the purpose to create a thermostable protein with growth hormone activity (GHA protein).

Design Strategies:

Core residues and boundary residues were selected for design since optimization of these positions can improve stability, although stabilization has been obtained from modifications at other sites as well. Core designs also minimize changes to the molecular surface and thus limit the designed protein's potential for antigenicity.

PDA calculations were run on one core sequence (CORE) two boundary sequences (BOUNDARY1 and BOUNDARY2 and a clustered boundary sequence (CLUSTERED BOUNDARY). For details see FIGS. 3A–D and below.

PDA Calculations

If possible, Dead End Elimination (DEE) was run to completion to find the PDA ground state. This was done for the PDA calculations for the A-chain and B-chain of Core 1, Core 2 and Core 2a, as defined below. For the calculation of Core 3, Core 4, Core 5, Core 6 and Core 7, DEE was aborted after the rotamer sequence space was reduced to less than $10^{25}$ sequences. The DEE calculation was for all the given Core calculation followed by Monte Carlo (MC) minimization and a list of the 1000 lowest energy sequences was generated.

The PDA calculations for all the designs were run using the a2h1p0 rotamer library. This library is based on the backbone-dependent rotamer library of Dunbrack and Karplus (Dunbrack and Karplus, J. Mol. Biol. 230(2):543–74 (1993); hereby expressly incorporated by reference) but includes more rotamers for the aromatic and hydrophobic amino acids; $X_1$ and $X_2$ angle values of rotamers for all the aromatic amino acids and $X_1$ angle values for all the other hydrophobic amino acids were expanded ±1 standard deviation about the mean value reported in the Dunbrack and Karplus library. Typical PDA parameters were used: the van der Waals scale factor was set to 0.9, the H-bond potential well-depth was set to 8.0 kcal/mol, the solvation potential was calculated using type 2 solvation with a nonpolar burial energy of 0.048 kcal/mol and a nonpolar exposure multiplication factor of 1.6, and the secondary structure scale factor was set to 0.0 (secondary structure propensities were not considered). Calculations required from 12–24 hours on 16 Silicon Graphics R10000 CPU's.

Monte Carlo Analysis

Monte Carlo analysis of the sequences produced by PDA shows the ground state (optimal) amino acid and amino acids allowed for each variable position and their frequencies of occurrence (see FIGS. 4 through 7).

EXAMPLE 2

The Design of the CORE Region

Different PDA calculations were performed for the core region of hGH. In these calculations the number of positions included in the PDA design were varied and the effect of different PDA parameters on the resulting protein sequences, especially the ground state sequences, was analyzed (see below).

The residues in the structure of hGH were divided into core, boundary and surface categories. By visual inspection of the structure, the following positions were identified as belonging to the core of the protein: 6, 10, 13, 17, 20, 24, 27, 28, 31, 36, 44, 54, 55, 58, 73, 75, 76, 78, 79, 80, 81, 82, 83, 85, 90, 93, 96, 97, 105, 110, 114, 117, 121, 124, 157, 161, 162, 163, 166, 170, 173, 176, 177, 180, and 184.

Numbering of the residues follows the one in the Brookhaven Data Bank. A rotamer group was assigned to each CORE position which allows this position to become any hydrophobic residue, i.e., Ala, Val, Leu, Ile, Phe, Tyr, Trp, Met or Ser. In the following PDA design, only the CORE residues were allowed to mutate to any rotamer of the hydrophobic amino acids. The rest of the protein was treated as a template with fixed coordinates.

Thus, the following positions/amino acid residues were included in the PDA design of the (see also FIGS. 3A and 4A):

6 10 13 17 20 24 27 28 31 36 44 54 55 58 73 75 76 78 79 80

Leu Phe Ala Ala Leu Ala Thr Tyr Phe Ile Phe Phe Ser Ile Leu Leu Leu Ile Ser Leu 81 82 83 85 90 93 96 97 105 110 114 117 121 124 157 161 162 163 166 170

Leu Leu Ile Ser Val Leu Val Phe Ala Val Leu Leu Ile Leu Leu Gly Leu Leu Phe Met 173 176 177 180 184

Val Phe Leu Val Ser (SEQ ID NO:14)

An energy cutoff of 50 kacl/mol for the rotamer/template was used to exclude unfavorable rotomers. The van der Waals radius was scaled by a factor of 0.9 and the salvation model 2 was used as defined by Street and Mayo [Fold. Des. 3(4):253–8 (1998)]. Distance-dependent eletrostatics with a dielectric constant 40 was used. The other parameters were as follows: hydrogen bond well depth energy—8 kcal/mol; non-polar burial penalty energy—0.048 kcal/mol/A2; non-polar exposure multiplication factor—1.0; polar burial penalty energy—0.0 kcal/mol/A2; polar hydrogen burial penalty energy—2 kcal/mol, amino acid type dependent entropy penalties were used to account for entropic contribution to the free energy of unfolding.

The parameters are obtained by summing up the side-chain entropy scale by Pickett & Sternberg [J. Mol. Biol. 213:825–839 (1993)] and the backbone scale by Stites & Pranata [J. Proteins 22:132–140 (1995)], and referencing them to gly (−1.92 kcavmol), i.e., assuming that for glycine the backbone entropy change associated with the unfolding of an α-helix is 6.51 cal/K=1.92 kcal/mol at 295 C [D'Aquino et al., Proteins 25:143–156 (1996)], and weighing by a factor of 2.3 obtained through minimization of the number of mutations when redesigning 45 core residues of hGH. The actual penalties (kcal/mol) are as follows: Ala, 2.7931; Cys, 5.0256; Asp, 6.6208; Glu, 7.1096; Phe, 5.0256; Gly, 4.4325; His, 6.1614; Hsp, 6.1614; Ile, 5.1094; Lys, 7.9331; Leu, 4.9429; Met, 6.9433; Asn, 7.6298; Pro, 2.5400; Gln, 8.1833; Arg, 7.9331; Ser 7.6896; Thr, 7.5114; Val, 4.2845; Trp 5.6374; Tyr 5.9183.

The best energy rotamer sequence was extracted from all possible rotamer sequences using the Dead End Elimination (DEE) method. In order to obtain other low energy sequences a Monte Carlo Search was performed starting from the DEE solution.

The PDA of the hGH CORE resulted in the following DEE ground state sequence (SEQ ID NO:3):

6 10 13 17 20 24 27 28 31 36 44 54 55 58 73 75 76 78 79 80

Leu Phe Val Ala Leu Ala Val Phe Phe Ile Phe Tyr Ala Ile Leu Leu Leu Ile Ala Leu 81 82 83 85 90 93 96 97 105 110 114 117 121 124 157 161 162 163 166 170

Leu Leu Ile Ala Ile Leu Val Phe Ala Val Met Leu Ile Leu Leu Met Leu Leu Phe Met 173 176 177 180 184

Val Phe Leu Val Ala (SEQ ID NO:3)

This sequence shows 11 mutations from the wild type hGH sequence, A13V, T27V, Y28F, 55A, S79A, S85A, V90I, L114M, G161M, and S184A (see also FIG. 4B)(SEQ ID NO:3).

Other sequences, such as COREDESIGN1, COREDESIGN2, and COREDESIGN3 can be derived:

COREDESIGN1: A13V, T27V, S79A, V90I, G161M, and S184A (see also FIG. 4C) (SEQ ID NO. 4).

6 10 13 17 20 24 27 28 31 36 44 54 55 58 73 75 76 78 79 80

Leu Phe Val Ala Leu Ala Val Tyr Phe Ile Phe Phe Ser Ile Leu Leu Leu Ile Ala Leu 81 82 83 85 90 93 96 97 105 110 114 117 121 124 157 161 162 163 166 170

Leu Leu Ile Ser Ile Leu Val Phe Ala Val Leu Leu Ile Leu Leu Met Leu Leu Phe Met 173 176 177 180 184

Val Phe Leu Val Ala (SEQ ID NO:4)

COREDESIGN2: A13V, T27V, S55A, S79A, S85A, V90I, G161M, and S184A (see also FIG. 4D) (SEQ ID NO:5).

6 10 13 17 20 24 27 28 31 36 44 54 55 58 73 75 76 78 79 80

Leu Phe Val Ala Leu Ala Val Tyr Phe Ile Phe Phe Ala Ile Leu Leu Leu Ile Ala Leu 81 82 83 85 90 93 96 97 105 110 114 117 121 124 157 161 162 163 166 170

Leu Leu Ile Ala Ile Leu Val Phe Ala Val Leu Leu Ile Leu Leu Met Leu Leu Phe Met 173 176 177 180 184

Val Phe Leu Val Ala (SEQ ID NO:5)

COREDESIGN3: A13V, T27V, Y28F, F54Y, S55A, S79A, S85A, V90I, G161M, and S184A (see also FIG. 4E) (SEQ ID NO:6).

6 10 13 17 20 24 27 28 31 36 44 54 55 58 73 75 76 78 79 80

Leu Phe Val Ala Leu Ala Val Phe Phe Ile Phe Tyr Ala Ile Leu Leu Leu Ile Ala Leu 81 82 83 85 90 93 96 97 105 110 114 117 121 124 157 161 162 163 166 170

Leu Leu Ile Ala Ile Leu Val Phe Ala Val Leu Leu Ile Leu Leu Met Leu Leu Phe Met 173 176 177 180 184

Val Phe Leu Val Ala (SEQ ID NO:6).

Using Monte Carlo technique a list of low energy sequences was generated for the CORE. The analysis of the lowest 1000 protein sequences generated by Monte Carlo leads to the mutation pattern shown in FIG. 4A. Thus, any protein sequence showing mutations at the positions according to FIG. 4A will potentially generate a more stable and active GHA protein. In particular those protein sequences found among the list of the lowest 50 MC generated sequences (data not shown) have a high potential to result in a more stable and active GHA protein. Preferred GHA protein sequences are shown in FIGS. 4B to 4E (SEQ ID NOS:3–6).

EXAMPLE 3

The Design of the BOUNDARY1 and BOUNDARY2 Regions

Two sets of boundary residues were selected approximately uniformly distributed in the structure:

Positions for PDA analysis of BOUNDARY 1: 6, 14, 26, 30, 32, 34, 35, 40, 50, 56, 57, 59, 66, 71, 74, 92, 107, 109, 113, 118, 125, 130, 139, 143, 157, 158, and 183.

Thus, the following positions/amino acid residues were included in the PDA design of BOUNDARY1 (see also FIG. 3B):

6 14 26 30 32 34 35 40 50 56 57 59 66 71 74 84 92 107 109 113

Leu Met Asp Glu Glu Ala Tyr Gln Thr Glu Ser Pro Glu Ser Glu Gln Phe Asp Asn Leu 118 125 130 139 143 157 158 183

Glu Met Asp Phe Tyr Leu Lys Arg (SEQ ID NO:14)

Positions for PDA analysis of BOUNDARY 2: 7, 29, 43, 70, 77, 87, 98, 100, 102, 104, 106, 111, 115, 132, 137, 140, 141, 142, 156, 159, 161, 184, 185, and 188.

Thus, the following positions/amino acid residues were included in the PDA design of BOUNDARY2 (see also FIG. 3C):

7 29 43 70 77 87 98 100 102 104 106 111 115 132 137 140 141 142 156 159

Ser Gln Ser Lys Arg Leu Ala Ser Val Gly Ser Tyr Lys Ser Ala Lys Ala Ala Leu Asn 161 184 185 188

Gly Ser Val Ser (SEQ ID NO:14)

The above listed PDA sequence includes A137, A141, and A142, instead of Q137, Q141, and T142 of hGH. The following amino acid residues were modeled as Ala in the original x-ray structure (PDB entry 3HHR): T135, Q137, I138, Q141, T142, S144, K145, and D147. In the PDA designs, these positions were also kept as alanines.

The selections were obtained by filtering out the residues whose relative solvent accessible surface is less than 10% or more than 50% and the residues which are closer then 5 Å to any atoms of the receptor molecules in the 3HHR structure and by visual inspection.

Numbering of the residues follows the one in the Brookhaven Data Bank. A rotamer group was assigned to each position which allows this position to become any of the following residues: Ala, Val, Leu, Ile, Phe, Tyr, Trp, Asp, Asn, Glu, Gln, Lys, Ser, Thr, Hsp, Arg, Met, His, or Gly. In the following PDA design, the residues in each set were allowed to mutate to any rotamer of the above listed amino acids. The rest of the protein was treated as a template with fixed coordinates. The two boundary sets were designed independently, i.e., while designing one set, the other set was included in the template.

An energy cutoff of 50 kcal/mol for the rotamer/template was used to exclude unfavorable rotamers. The van der Waals radius was scaled by a factor of 0.9 and the solvation model 2 was used as defined by Street and Mayo [Fold. Des. 3(4):253–8 (1998)]. Distance-independent electrostatics with a dielectric constant of 8 for BOUNDARY1 and 13 for BOUNDARY2 regions was used. The other parameters were as follows: hydrogen bond well depth energy—8 kacl/mol; non-polar burial penalty energy—0.048 kcal/mol/VA2; non-polar exposure multiplication factor—1.6; polar burial penalty energy—0.1125 kcal/mol/VA2; polar hydrogen burial penalty energy—0 kcal/mol; amino acid type dependent entropy penalties were used to account for entropic contribution to the free energy of unfolding.

The best energy rotamer sequence was extracted from all possible rotamer sequences using the Dead End Elimination (DEE) method. In order to obtain other low energy sequences a Monte Carlo search was performed starting from the DEE solution.

The PDA of hGH BOUNDARY1 resulted in the following DEE ground state sequence (SEQ ID NO:7).

103331 6 14 26 30 32 34 35 40 50 55 57 59 66 71 74 84 92 107 109 113

Leu Leu Ala Val Glu Trp Tyr Lys Phe Glu Glu Val Glu His Glu Arg Glu Ala Phe Leu 118 125 130 139 143 157 158 183

Leu Ile Arg His Asp Leu Lys His (SEQ ID NO:7)

The energy is −29.62 kacl/mol. This sequence shows 19 mutations from the wild type hGH sequence, M14L, D26A, E30V, A34W, Q40K, T50F, S57E, P59V, S71H, Q84R, F92E, D107A, N109F, E118L, M125I, D130R, F139H, Y143D, and R183H (see also FIG. 5B)(SEQ ID NO:7).

The lowest energy sequence from the Monte Carlo calculation for BOUNDARY1 is as follows (SEQ ID NO:8):

6 14 26 30 32 34 35 40 50 56 57 59 66 71 74 84 92 107 109 113

Leu Leu Ala Trp Glu Lys Glu Lys Phe Glu Lys Glu Glu His Glu Arg Arg Asp Phe Leu 118 125 130 139 143 157 158 183

Leu Ile Arg His Asp Leu Phe His (SEQ ID NO:8)

The energy is −37.135 kcal/mol. This sequence shows 20 mutations from the wild type hGH sequence, M14L, D26A, E30W, A34K, Y35E, Q40K, T50F, S57K, P59E, S71H, Q84R, F92R, N109F, E111L, M125I, D130R, F139H, Y143D, K158F, and R183H (see also FIG. 5C)(SEQ ID NO:8).

Using Monte Carlo technique a list of low energy sequences was generated for BOUNDARY1. The analysis of the lowest 1000 protein sequences generated by Monte Carlo leads to the mutation pattern shown in FIG. 5A. Thus, any protein sequence showing mutations at the positions according to FIG. 5A will potentially generate a more stable and active GHA protein. In particular those protein sequences found among the list of the lowest 50 MC generated sequences (data not shown) have a high potential to result in a more stable and active GHA protein. Preferred GHA protein sequences are shown in FIGS. 5B and 5C (SEQ ID NOS:7–8).

The PDA analysis of hGH BOUNDARY2 resulted in the following DEE ground state sequence (SEQ ID NO:9):

7 29 43 70 77 87 98 100 102 104 106 111 115 132 137 140 141 142 156 159

Lys Lys Lys Lys Met Leu Val Ala Val Gly Lys Arg Lys Ala Trp Lys Lys Val Leu Phe 161 184 185 188

Met Ala Val Ala (SEQ ID NO:9)

The energy is 16.894 kcal/mol. This sequence shows 16 mutations from the wild type hGH sequence, S7K, Q29K, S43K, R77M, A98V, S100A, S106K, Y111R, S132A, A137W, A141K, A142V, G161M, S184A, and S188A (see also FIG. 6B)(SEQ ID NO:9).

Using Monte Carlo technique a list of low energy sequences was generated for BOUNDARY2. The analysis of the lowest 1000 protein sequences generated by Monte Carlo leads to the mutation pattern shown in FIG. 6A. Thus, any protein sequence showing mutations at the positions according to FIG. 6A will potentially generate a more stable and active GHA protein. In particular those protein sequences found among the list of the lowest 50 MC generated sequences (data not shown) have a high potential to result in a more stable and active GHA protein. A preferred GHA protein sequence is shown in FIG. 6B (SEQ ID NO:9).

EXAMPLE 4

The Design of the CLUSTERED BOUNDARY Region

In order to simplify experimental expression of GHA proteins another type of boundary design was performed. 21 residues clustered in three groups were chosen out of all residues classified as boundary. This set is called here CLUSTERED BOUNDARY region, Positions for PDA analysis of CLUSTERED BOUNDARY region: 26, 29, 30, 34, 40, 43, 50, 77, 84, 92, 100, 102, 111, 118, 125, 132, 137, 139, 141, 142, and 143.

All the other boundary residues were allowed to "float" during calculations, i.e., choose rotamers of the wild type amino acid. The above listed PDA sequence includes A137, A141, and A142, instead of Q137, Q141, and T142 of hGH. The following amino acid residues were modeled as Ala in the original x-ray structure (PDB entry 3HHR): T135, Q137, I138, Q141, T142, S144, K145, and D147. In this PDA design, three of these residues (position Q137, Q141, and T142) were taken into calculations. The others were forced to "float" and keep the wild type identity with the exception of 145, which was kept as alanine.

Thus, the following positions/amino acid residues were included in the PDA design of CLUSTERED BOUNDARY (see also FIG. 3D.):

7 14 26 29 30 34 40 43 50 57 70 77 84 87 92 98 100 102 104 106

Ser Met Asp Gln Glu Ala Gln Ser Thr Ser Lys Arg Gln Leu Phe Ala Ser Val Gly Ser 109 111 115 118 125 132 135 137 138 140 141 142 143 144 145 147 156 159 161 184

Asn Tyr Lys Glu Met Ser Thr Gln Ile Lys Gln Thr Tyr Ser Lys Asp Leu Asn Gly Ser 185 188

Val Ser (SEQ ID NO:1)

The of calculation parameters were as follows: the cutoff for the rotamer/template energy was 50 kcal/mol; the van der Waals radius was scaled by a factor of 0.9; distance-independent dielectric constant was 10.5; the salvation model 2 was used; hydrogen bond well depth energy was 8 kcal/mol; non-polar burial penalty energy was 0.048 kcal/mol/VA2; non-polar exposure multiplication factor was 1.6; polar burial penalty energy was 0.144 kcal/mol/A2; polar hydrogen burial penalty energy was 0 kcal/mol; amino acid type dependent entropy penalties were used to account for entropic contribution to the free energy of unfolding.

The best energy rotamer sequence was extracted from all possible rotamer sequences using the Dead End Elimination (DEE) method In order to obtain other low energy sequences a Monte Carlo search was performed starting from the DEE solution.

The PDA of hGH CLUSTERED BOUNDARY resulted in the following DEE ground state sequence (SEQ ID NO:10):

7 14 26 29 30 34 40 43 50 57 70 77 84 87 92 98 100 102 104 106

Ser Met Lys Ile Val Trp Val Lys Phe Ser Lys Met Met Leu Val Ala Ala Ile Gly Ser 109 111 115 118 125 132 135 137 138 140 141 142 143 144 145 147 156 159 161 184

Phe Arg Lys Met Ile Ala Thr Arg Ile Lys Phe Val Val Ser Ala Asp Leu Asn Gly Ser 185 188

Val Ser (SEQ ID NO:10)

This sequence shows 22 mutations from the wild type hGH sequence, D26K, Q29I, E30V, Q40V, S43K, T50F, R77M, Q84M, F92V, S100A, V102I, N109F, Y111R, E118M, M125I, S132A, Q137R, Q141F, T142V, Y143V, and K145A (see also FIG. 7B)(SEQ ID NO:10).

Other sequences such as BOUNDARYDESIGN1, BOUNDARYDESIGN2, and BOUNDARYDESIGN3 can be derived.

BOUNDARYDESIGN1 (SEQ ID NO:11):

7 14 26 29 30 34 40 43 50 57 70 77 84 87 92 98 100 102 104 106

Ser Met Lys Ile Val Trp Trp Trp Phe Ser Lys Met Met Leu Val Ala Ala Ile Gly Ser 109 111 115 118 125 132 135 137 138 140 141 142 143 144 145 147 156 159 161 184

Phe Arg Lys Met Ile Ala Ala Arg Ala Lys Phe Val Val Ala Ala Ala Leu Asn Gly Ser 185 188

Val Ser (SEQ ID NO:11)

This sequence shows 26 mutations from the wild type hGH sequence, D26K, Q29I, E30V, Q40W, S43W, T50F, R77M, Q84M, F92V, S100A, V102I, N109F, Y111R, E118M, M125I, S132A, T135A, Q137R, 1138A, Q141F, T142V, Y143V, S144A, K145A, and D147A (see also FIG. 7C)(SEQ ID NO:11).

BOUNDARYDESIGN2 (SEQ ID NO:12):

7 14 26 29 30 34 40 43 50 57 70 77 84 87 92 98 100 102 104 106

Ser Met Lys Ile Val Trp Val Lys Phe Ser Lys Met Met Leu Val Ala Ala Ile Gly Ser 109 111 115 118 125 132 135 137 138 140 141 142 143 144 145 147 156 159 161 184

Phe Arg Lys Met Ile Ala Ala Arg Ala Lys Phe Val Val Ala Ala Ala Leu Asn Gly Ser 185 188

Val Ser (SEQ ID NO:12)

This sequence shows 26 mutations from the wild type hGH sequence, D26K, Q29I, E30V, Q40V, S43K, T50F, R77M, Q84M, F92V, S100A, V102I, N109F, Y111R, E118M, M125I, S132A, T135A, Q137R, I138A, Q141 F, T142V, Y143V, S144A, K145A, and D147A (see also FIG. 7D)(SEQ ID NO:12).

BOUNDARYDESIGN3 (SEQ ID NO:13):

7 14 26 29 30 34 40 43 50 57 70 77 84 87 92 98 100 102 104 106

Ser Met Glu Lys Val Trp Val Lys Phe Ser Lys Met Met Leu Val Ala Ala Val Gly Ser 109 111 115 118 125 132 135 137 138 140 141 142 143 144 145 147 156 159 161 184

Phe Arg Lys Lys Ile Ala Ala Arg Ala Lys Phe Val Val Ala Ala Ala Leu Asn Gly Ser 185 188

Val Ser (SEQ ID NO:13)

This sequence shows 25 mutations from the wild type hGH sequence, D26E, Q29K, E30V, Q40V, S43K, T50F, R77M, Q84M, F92V, S100A, N109F, Y111R, E118K, M125I, S132A, T135A, Q137R, I138A, Q141F, T142V, Y143V, S144A, K145A, and D147A (see also FIG. 7E) (SEQ ID NO:13).

Using Monte Carlo technique a list of low energy sequences was generated for CLUSTERED BOUNDARY. The analysis of the lowest 1000 protein sequences generated by Monte Carlo leads to the mutation pattern shown in FIG. 7A. Thus, any protein sequence showing mutations at the positions according to FIG. 7A will potentially generate a more stable and active GHA protein. In particular those protein sequences found among the list of the lowest 50 MC generated sequences (data not shown) have a high potential to result in a more stable and active GHA protein. Preferred GHA protein sequences are shown in FIGS. 7B and 7E (SEQ ID NOS:10, 13).

EXAMPLE 5

HGA Protein Expression and Refolding

HGA proteins of the invention were expressed in *E.coli* using standard protocols (e.g., see Shambrook et al., supra, Ausubel et al., supra). Inclusion bodies were prepared as known in the art. Approximately 0.5 g of wet inclusion bodies were dissolved in 5 ml of wash buffer A (100 mM Tris/HCl, pH 8.0; 2% triton; 4M urea; 5 mM EDTA; 0.5 mM DTT), mixed, vortexed and centrifuged at 20,000 g for 30 min. The pellet was washed in buffer B (100 mM Tris/HCl, pH 8.0; 0.5 mM DTT), mixed, vortexed and centrifuged at 20,000 g for 30 min. The pellet was resuspended in extraction buffer (50 mM glycine; 0.0156 M NaOH, 5 mM reduced GSH; 8M GdnHCl, pH 9.6) at 3 ml/g pellet. The proteins were dispersed by sonication (tip midway in solution; output control: 7; duty cycle: 80%; 10 second pulses on ice). The sample was centrifuged (20,000 g for 30 min) to get rid of pellet debris. The supernatant was analyzed for protein concentration and if necessary adjusted to 2 mg protein/ml. The supernatant is dialyzed for 12–16 hours or over night against folding buffer A (50 mM glycine; 0.0156 M NaOH; 10% sucrose; 1 mM EDTA; 1 mM reduced GSH; 0.1 mM oxidized GSSG; 4 M urea, pH 9.6). After dialyzing against folding buffer B (60 mM Tris, pH 9.6; 10% sucrose; 1 mM EDTA; 0.1 mM reduced GSH; 0.01 mM oxidized GSSG) the supernatant was filtered and purified further by column chromatography (HPLC-SE).

EXAMPLE 6

Thermal Stability of HGA Proteins

HGA proteins expressed and purified as described herein were analyzed for thermal stability and compared to hGH. HGA proteins, mutant b (A13V, T27V, S79A, V9I, G161M, and S184A) (SEQ ID NO:4), mutant d (A13V, T27V, S55A, S79A, S85A, V90I, G161M, and S184A) (SEQ ID NO:5) and mutant f (A13V, T27V, Y28F, F54Y, S55A, S79A, S85A, V90I, G161M, and S184A) (SEQ ID NO:6) were compared to hGH.

The far-ultraviolet (UV) CD spectra for hGH and the HGA proteins, mutants b, d, and f, were nearly identical to each other, indicating highly similar secondary structure and tertiary folds (data not shown). Thermal denaturation was monitored at 220 nm, and the melting temperatures ($T_m$'s) were derived from derivative curve of the ellipticity at 220 nm vs. temperature. GHA protein mutant b (SEQ ID NO:4) showed an increase in stability of 16° C. and GHA protein mutant d (SEQ ID NO:5) of 13° C. (FIG. 13).

EXAMPLE 7

Cell Proliferation Assays

Cell proliferation assays were performed using an interleukin 3- dependent murine myeloid cell line FDC-P1 stably transfected with the full-length human growth hormone receptor (hGHR) and according to the method of Rowlinson et al. [J. Biol. Chem. 270(28) 16833–16839 (1995); Endocrinology 137(1):90–5 (1996)]. Cells were maintained in RPMI-1640 medium with 5% fetal calfserum (FCS), 1 μg/ml gentamicin, 50 units/ml interleukin 3 (IL-3). In preparation for the assay, exponentially growing cells were washed twice in PBS and resuspended in hGH-free and phenol red-free RPMI-1640 media with 5% FCS and 1 μg/ml gentamicin. Cells were then added to microtiter plates containing serial diluted hGH or GHA proteins for a final concentration of $2.6 \times 10^5$ cells/well. The plates were incubated at 37° C. in 5% $CO_2$. After 24 hours, cell growth was quantified by the reduction of tetrazolium salt (MTT assay). All GHA protein mutants were assayed in triplicate on the same plate and the assay was repeated three times. $EC_{50}$ values were determined as described by Young et al. [Protein Science 6:1228–1236 (1997)] using Kaleidagraph (Synergy Software) by nonlinear least-squares fit to four parameter equation:

$$OD = OD_{max} - (OD_{max} - OD_{min})/(1+([concentration]/EC_{50}))^n$$

The Activity of hGH and GHA protein mutants b, d, and f (SEQ ID NOS:4–6) was determined using the assay described above. The ED50 values are as follows: wild type hGH (220±20); GHA mutant b (320±30); GHA protein mutant d (260±50); and GHA protein mutant b (230±50).

We claim:

1. A non-naturally occurring growth hormone activity (GHA) protein comprising eleven amino acid substitutions as compared to the hGH protein of SEQ ID NO: 14, said substitutions comprising A13V, T27V, Y28F, F54Y, S55A, S79A, S85A, V90I, L114M, G161M, and S184A, and comprising the amino acid sequence of SEQ ID NO: 3.

2. A non-naturally occurring GHA protein comprising ten amino acid substitutions as compared to the hGH protein of SEQ ID NO: 14, said amino acid substitutions comprising A13V, T27V, Y28F, F54Y, S55A, S79A, S85A, V90I, G161M, and S184A, and comprising the amino acid sequence of SEQ ID NO: 9.

3. A non-naturally occurring GHA protein comprising eight amino acid substitutions as compared to the hGH protein of SEQ ID NO: 14, said amino acid substitutions comprising A13V, T27V, S55A, S79A, S85A, V90I, G161M, and S184A, and comprising the amino acid sequence of SEQ ID NO: 5.

4. A non-naturally occurring GHA protein comprising six amino acid substitutions as compared to the hGH protein of SEQ ID NO: 14, said amino acid substitutions comprising A13V, T27V, S79A, V90I, G161M, and S184A, and comprising the amino acid sequence of SEQ ID NO: 4.

5. A recombinant nucleic acid encoding the non-naturally occurring GHA protein of claim 1, 2, 3, or 4.

6. An expression vector comprising the recombinant nucleic acid of claim 5.

7. A host cell comprising the recombinant nucleic acid of claim 5.

8. A host cell comprising the expression vector of claim 6.

9. A method of producing a non-naturally occurring GHA protein comprising culturing the host cell of claim 8 under conditions suitable for expression of said nucleic acid.

10. A method according to claim 9, further comprising recovering said GHA protein.

11. A pharmaceutical composition comprising a GHA protein according to claim 1, 2, 3, or 4 and a pharmaceutical carrier.

* * * * *

SEQUENCE LISTING

<160> NUMBER OF SEQ ID NOS: 14

<210> SEQ ID NO 1
<211> LENGTH: 217
<212> TYPE: PRT
<213> ORGANISM: Homo sapiens
<220> FEATURE:
<221> NAME/KEY: SIGNAL
<222> LOCATION: (1)..(26)
<220> FEATURE:
<221> NAME/KEY: mat_peptide
<222> LOCATION: (27)..()

<400> SEQUENCE: 1

Met Ala Thr Gly Ser Arg Thr Ser Leu Leu Leu Ala Phe Gly Leu Leu
    -25                 -20                 -15

Cys Leu Pro Trp Leu Gln Glu Gly Ser Ala Phe Pro Thr Ile Pro Leu
-10                  -5              -1   1                   5

Ser Arg Leu Phe Asp Asn Ala Met Leu Arg Ala His Arg Leu His Gln
                10                  15                  20

Leu Ala Phe Asp Thr Tyr Gln Glu Phe Glu Glu Ala Tyr Ile Pro Lys
            25                  30                  35

Glu Gln Lys Tyr Ser Phe Leu Gln Asn Pro Gln Thr Ser Leu Cys Phe
 40                  45                  50

Ser Glu Ser Ile Pro Thr Pro Ser Asn Arg Glu Glu Thr Gln Gln Lys
55                  60                  65                  70

Ser Asn Leu Glu Leu Leu Arg Ile Ser Leu Leu Ile Gln Ser Trp
                75                  80                  85

Leu Glu Pro Val Gln Phe Leu Arg Ser Val Phe Ala Asn Ser Leu Val
            90                  95                  100

Tyr Gly Ala Ser Asp Ser Asn Val Tyr Asp Leu Leu Lys Asp Leu Glu
            105                 110                 115

Glu Gly Ile Gln Thr Leu Met Gly Arg Leu Glu Asp Gly Ser Pro Arg
            120                 125                 130

Thr Gly Gln Ile Phe Lys Gln Thr Tyr Ser Lys Phe Asp Thr Asn Ser
135                 140                 145                 150

His Asn Asp Asp Ala Leu Leu Lys Asn Tyr Gly Leu Leu Tyr Cys Phe
                155                 160                 165

Arg Lys Asp Met Asp Lys Val Glu Thr Phe Leu Arg Ile Val Gln Cys
            170                 175                 180

Arg Ser Val Glu Gly Ser Cys Gly Phe
            185                 190

<210> SEQ ID NO 2
<211> LENGTH: 799
<212> TYPE: DNA
<213> ORGANISM: Homo sapiens

<400> SEQUENCE: 2
cgaaccactc agggtcctgt ggacagctca cctagctgca atggctacag gctcccggac      60
gtccctgctc ctggcttttg gcctgctctg cctgccctgg cttcaagagg gcagtgcctt     120
cccaaccatt cccttatcca ggccttttga caacgctatg ctccgcgccc atcgtctgca     180
ccagctggcc tttgacacct accaggagtt tgaagaagcc tatatcccaa aggaacagaa     240
gtattcattc ctgcagaacc ccagacctc ctctgtttc tcagagtcta ttccgacacc       300
ctccaacagg gaggaaacac aacagaaatc caacctagag ctgctccgca tctccctgct    360

```
gctcatccag tcgtggctgg agcccgtgca gttcctcagg agtgtcttcg ccaacagcct    420
ggtgtacggc gcctctgaca gcaacgtcta tgacctccta aaggacctag aggaaggcat    480
ccaaacgctg atggggaggc tggaagatgg cagcccccgg actgggcaga tcttcaagca    540
gacctacagc aagttcgaca caaactcaca caacgatgac gcactactca agaactacgg    600
gctgctctac tgcttcagga aggacatgga caaggtcgag acattcctgc gcatcgtgca    660
gtgccgctct gtggagggca gctgtggctt ctagctgccc gggtggcatc cctgtgaccc    720
ctccccagtg cctctcctgg ccctggaagt tgccactcca gtgcccacca gccttgtcct    780
aataaaatta agttgcatc                                                 799
```

<210> SEQ ID NO 3
<211> LENGTH: 191
<212> TYPE: PRT
<213> ORGANISM: Artificial sequence
<220> FEATURE:
<223> OTHER INFORMATION: synthetic

<400> SEQUENCE: 3

```
Phe Pro Thr Ile Pro Leu Ser Arg Leu Phe Asp Asn Val Met Leu Arg
1               5                   10                  15

Ala His Arg Leu His Gln Leu Ala Phe Asp Val Phe Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Tyr Ala Glu Ser Ile Pro Thr Pro Ser Asn Arg
    50                  55                  60

Glu Glu Thr Gln Gln Lys Ser Asn Leu Glu Leu Leu Arg Ile Ala Leu
65                  70                  75                  80

Leu Leu Ile Gln Ala Trp Leu Glu Pro Ile Gln Phe Leu Arg Ser Val
                85                  90                  95

Phe Ala Asn Ser Leu Val Tyr Gly Ala Ser Asp Ser Asn Val Tyr Asp
            100                 105                 110

Leu Met Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Met Leu Leu Tyr Cys Phe Arg Lys Asp Met Asp Lys Val Glu Thr Phe
                165                 170                 175

Leu Arg Ile Val Gln Cys Arg Ala Val Glu Gly Ser Cys Gly Phe
            180                 185                 190
```

<210> SEQ ID NO 4
<211> LENGTH: 191
<212> TYPE: PRT
<213> ORGANISM: Artificial sequence
<220> FEATURE:
<223> OTHER INFORMATION: synthetic

<400> SEQUENCE: 4

```
Phe Pro Thr Ile Pro Leu Ser Arg Leu Phe Asp Asn Val Met Leu Arg
1               5                   10                  15

Ala His Arg Leu His Gln Leu Ala Phe Asp Val Tyr Gln Glu Phe Glu
            20                  25                  30
```

```
Glu Ala Tyr Ile Pro Lys Glu Gln Lys Tyr Ser Phe Leu Gln Asn Pro
            35                  40                  45

Gln Thr Ser Leu Cys Phe Ser Glu Ser Ile Pro Thr Pro Ser Asn Arg
 50                  55                  60

Glu Glu Thr Gln Gln Lys Ser Asn Leu Glu Leu Leu Arg Ile Ala Leu
 65                  70                  75                  80

Leu Leu Ile Gln Ser Trp Leu Glu Pro Ile Gln Phe Leu Arg Ser Val
                85                  90                  95

Phe Ala Asn Ser Leu Val Tyr Gly Ala Ser Asp Ser Asn Val Tyr Asp
                100                 105                 110

Leu Leu Lys Asp Leu Glu Glu Gly Ile Gln Thr Leu Met Gly Arg Leu
            115                 120                 125

Glu Asp Gly Ser Pro Arg Thr Gly Gln Ile Phe Lys Gln Thr Tyr Ser
130                 135                 140

Lys Phe Asp Thr Asn Ser His Asn Asp Asp Ala Leu Leu Lys Asn Tyr
145                 150                 155                 160

Met Leu Leu Tyr Cys Phe Arg Lys Asp Met Asp Lys Val Glu Thr Phe
                165                 170                 175

Leu Arg Ile Val Gln Cys Arg Ala Val Glu Gly Ser Cys Gly Phe
                180                 185                 190

<210> SEQ ID NO 5
<211> LENGTH: 191
<212> TYPE: PRT
<213> ORGANISM: Artificial sequence
<220> FEATURE:
<223> OTHER INFORMATION: synthetic

<400> SEQUENCE: 5

Phe Pro Thr Ile Pro Leu Ser Arg Leu Phe Asp Asn Val Met Leu Arg
 1               5                  10                  15

Ala His Arg Leu His Gln Leu Ala Phe Asp Val Tyr Gln Glu Phe Glu
            20                  25                  30

Glu Ala Tyr Ile Pro Lys Glu Gln Lys Tyr Ser Phe Leu Gln Asn Pro
            35                  40                  45

Gln Thr Ser Leu Cys Phe Ala Glu Ser Ile Pro Thr Pro Ser Asn Arg
 50                  55                  60

Glu Glu Thr Gln Gln Lys Ser Asn Leu Glu Leu Leu Arg Ile Ala Leu
 65                  70                  75                  80

Leu Leu Ile Gln Ala Trp Leu Glu Pro Ile Gln Phe Leu Arg Ser Val
                85                  90                  95

Phe Ala Asn Ser Leu Val Tyr Gly Ala Ser Asp Ser Asn Val Tyr Asp
                100                 105                 110

Leu Leu Lys Asp Leu Glu Glu Gly Ile Gln Thr Leu Met Gly Arg Leu
            115                 120                 125

Glu Asp Gly Ser Pro Arg Thr Gly Gln Ile Phe Lys Gln Thr Tyr Ser
130                 135                 140

Lys Phe Asp Thr Asn Ser His Asn Asp Asp Ala Leu Leu Lys Asn Tyr
145                 150                 155                 160

Met Leu Leu Tyr Cys Phe Arg Lys Asp Met Asp Lys Val Glu Thr Phe
                165                 170                 175

Leu Arg Ile Val Gln Cys Arg Ala Val Glu Gly Ser Cys Gly Phe
                180                 185                 190

<210> SEQ ID NO 6
<211> LENGTH: 191
```

```
<212> TYPE: PRT
<213> ORGANISM: Artificial sequence
<220> FEATURE:
<223> OTHER INFORMATION: synthetic

<400> SEQUENCE: 6
```

Phe Pro Thr Ile Pro Leu Ser Arg Leu Phe Asp Asn Val Met Leu Arg
1               5                   10                  15

Ala His Arg Leu His Gln Leu Ala Phe Asp Val Phe Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Tyr Ala Glu Ser Ile Pro Thr Pro Ser Asn Arg
    50                  55                  60

Glu Glu Thr Gln Gln Lys Ser Asn Leu Glu Leu Arg Ile Ala Leu
65                  70                  75                  80

Leu Leu Ile Gln Ala Trp Leu Glu Pro Ile Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Met Leu Leu Tyr Cys Phe Arg Lys Asp Met Asp Lys Val Glu Thr Phe
                165                 170                 175

Leu Arg Ile Val Gln Cys Arg Ala Val Glu Gly Ser Cys Gly Phe
            180                 185                 190

```
<210> SEQ ID NO 7
<211> LENGTH: 191
<212> TYPE: PRT
<213> ORGANISM: Artificial sequence
<220> FEATURE:
<223> OTHER INFORMATION: synthetic

<400> SEQUENCE: 7
```

Phe Pro Thr Ile Pro Leu Ser Arg Leu Phe Asp Asn Ala Leu Leu Arg
1               5                   10                  15

Ala His Arg Leu His Gln Leu Ala Phe Ala Thr Tyr Gln Val Phe Glu
            20                  25                  30

Glu Trp Tyr Ile Pro Lys Glu Lys Lys Tyr Ser Phe Leu Gln Asn Pro
        35                  40                  45

Gln Phe Ser Leu Cys Phe Ser Glu Glu Ile Val Thr Pro Ser Asn Arg
    50                  55                  60

Glu Glu Thr Gln Gln Lys His Asn Leu Glu Leu Leu Arg Ile Ser Leu
65                  70                  75                  80

Leu Leu Ile Arg Ser Trp Leu Glu Pro Val Gln Glu Leu Arg Ser Val
                85                  90                  95

Phe Ala Asn Ser Leu Val Tyr Gly Ala Ser Ala Ser Phe Val Tyr Asp
            100                 105                 110

Leu Leu Lys Asp Leu Leu Glu Gly Ile Gln Thr Leu Ile Gly Arg Leu
        115                 120                 125

Glu Arg Gly Ser Pro Arg Thr Gly Gln Ile His Lys Gln Thr Asp Ser
    130                 135                 140

```
Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys His Ser Val Glu Gly Ser Cys Gly Phe
            180                 185                 190
```

<210> SEQ ID NO 8
<211> LENGTH: 191
<212> TYPE: PRT
<213> ORGANISM: Artificial sequence
<220> FEATURE:
<223> OTHER INFORMATION: synthetic

<400> SEQUENCE: 8

```
Phe Pro Thr Ile Pro Leu Ser Arg Leu Phe Asp Asn Ala Leu Leu Arg
1               5                   10                  15

Ala His Arg Leu His Gln Leu Ala Phe Ala Thr Tyr Gln Trp Phe Glu
                20                  25                  30

Glu Lys Glu Ile Pro Lys Glu Lys Tyr Ser Phe Leu Gln Asn Pro
            35                  40                  45

Gln Phe Ser Leu Cys Phe Ser Glu Lys Ile Glu Thr Pro Ser Asn Arg
50                  55                  60

Glu Glu Thr Gln Gln Lys His Asn Leu Glu Leu Leu Arg Ile Ser Leu
65                  70                  75                  80

Leu Leu Ile Arg Ser Trp Leu Glu Pro Val Gln Arg Leu Arg Ser Val
                85                  90                  95

Phe Ala Asn Ser Leu Val Tyr Gly Ala Ser Asp Ser Phe Val Tyr Asp
                100                 105                 110

Leu Leu Lys Asp Leu Leu Glu Gly Ile Gln Thr Leu Ile Gly Arg Leu
            115                 120                 125

Glu Arg Gly Ser Pro Arg Thr Gly Gln Ile His Lys Gln Thr Asp Ser
130                 135                 140

Lys Phe Asp Thr Asn Ser His Asn Asp Asp Ala Leu Leu Phe Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys His Ser Val Glu Gly Ser Cys Gly Phe
            180                 185                 190
```

<210> SEQ ID NO 9
<211> LENGTH: 191
<212> TYPE: PRT
<213> ORGANISM: Artificial sequence
<220> FEATURE:
<223> OTHER INFORMATION: synthetic

<400> SEQUENCE: 9

```
Phe Pro Thr Ile Pro Leu Lys Arg Leu Phe Asp Asn Ala Met Leu Arg
1               5                   10                  15

Ala His Arg Leu His Gln Leu Ala Phe Asp Thr Tyr Lys Glu Phe Glu
                20                  25                  30

Glu Ala Tyr Ile Pro Lys Glu Gln Lys Tyr Lys Phe Leu Gln Asn Pro
            35                  40                  45

Gln Thr Ser Leu Cys Phe Ser Glu Ser Ile Pro Thr Pro Ser Asn Arg
50                  55                  60
```

Glu Glu Thr Gln Gln Lys Ser Asn Leu Glu Leu Leu Met Ile Ser Leu
65                  70                  75                  80

Leu Leu Ile Gln Ser Trp Leu Glu Pro Val Gln Phe Leu Arg Ser Val
                85                  90                  95

Phe Val Asn Ala Leu Val Tyr Gly Ala Lys Asp Ser Asn Val Arg Asp
            100                 105                 110

Leu Leu Lys Asp Leu Glu Glu Gly Ile Gln Thr Leu Met Gly Arg Leu
            115                 120                 125

Glu Asp Gly Ala Pro Arg Thr Gly Trp Ile Phe Lys Lys Val Tyr Ser
        130                 135                 140

Lys Phe Asp Thr Asn Ser His Asn Asp Asp Ala Leu Leu Lys Phe Tyr
145                 150                 155                 160

Met Leu Leu Tyr Cys Phe Arg Lys Asp Met Asp Lys Val Glu Thr Phe
                165                 170                 175

Leu Arg Ile Val Gln Cys Arg Ala Val Glu Gly Ala Cys Gly Phe
            180                 185                 190

<210> SEQ ID NO 10
<211> LENGTH: 190
<212> TYPE: PRT
<213> ORGANISM: Artificial sequence
<220> FEATURE:
<223> OTHER INFORMATION: synthetic

<400> SEQUENCE: 10

Phe Pro Thr Ile Pro Leu Ser Arg Leu Phe Asp Asn Ala Met Leu Arg
1               5                   10                  15

Ala His Arg Leu His Gln Leu Ala Phe Lys Thr Tyr Ile Val Phe Glu
            20                  25                  30

Glu Trp Tyr Ile Pro Lys Glu Val Lys Tyr Lys Phe Leu Gln Asn Pro
        35                  40                  45

Gln Phe Ser Leu Cys Phe Ser Glu Ser Ile Pro Thr Pro Ser Asn Arg
    50                  55                  60

Glu Glu Thr Gln Gln Lys Ser Asn Leu Glu Leu Leu Met Ile Ser Leu
65                  70                  75                  80

Leu Leu Ile Met Ser Trp Leu Glu Pro Val Gln Val Leu Arg Ser Val
                85                  90                  95

Phe Ala Asn Ala Leu Ile Tyr Gly Ala Ser Asp Ser Phe Val Arg Asp
            100                 105                 110

Leu Leu Lys Asp Leu Met Glu Gly Ile Gln Thr Leu Ile Gly Arg Leu
            115                 120                 125

Glu Asp Gly Ala Pro Arg Thr Gly Arg Ile Phe Lys Phe Val Val Ser
        130                 135                 140

Ala Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly
            180                 185                 190

<210> SEQ ID NO 11
<211> LENGTH: 190
<212> TYPE: PRT
<213> ORGANISM: Artificial sequence
<220> FEATURE:
<223> OTHER INFORMATION: synthetic

```
<400> SEQUENCE: 11

Phe Pro Thr Ile Pro Leu Ser Arg Leu Phe Asp Asn Ala Met Leu Arg
1               5                   10                  15

Ala His Arg Leu His Gln Leu Ala Phe Lys Thr Tyr Ile Val Phe Glu
            20                  25                  30

Glu Trp Tyr Ile Pro Lys Glu Trp Lys Tyr Trp Phe Leu Gln Asn Pro
        35                  40                  45

Gln Phe Ser Leu Cys Phe Ser Glu Ser Ile Pro Thr Pro Ser Asn Arg
    50                  55                  60

Glu Glu Thr Gln Gln Lys Ser Asn Leu Glu Leu Leu Met Ile Ser Leu
65                  70                  75                  80

Leu Leu Ile Met Ser Trp Leu Glu Pro Val Gln Val Leu Arg Ser Val
                85                  90                  95

Phe Ala Asn Ala Leu Ile Tyr Gly Ala Ser Asp Ser Phe Val Arg Asp
            100                 105                 110

Leu Leu Lys Asp Leu Met Glu Gly Ile Gln Thr Leu Ile Gly Arg Leu
        115                 120                 125

Glu Asp Gly Ala Pro Arg Ala Gly Arg Ala Phe Lys Phe Val Val Ala
    130                 135                 140

Ala Phe Ala Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly
            180                 185                 190

<210> SEQ ID NO 12
<211> LENGTH: 190
<212> TYPE: PRT
<213> ORGANISM: Artificial sequence
<220> FEATURE:
<223> OTHER INFORMATION: synthetic

<400> SEQUENCE: 12

Phe Pro Thr Ile Pro Leu Ser Arg Leu Phe Asp Asn Ala Met Leu Arg
1               5                   10                  15

Ala His Arg Leu His Gln Leu Ala Phe Lys Thr Tyr Ile Val Phe Glu
            20                  25                  30

Glu Trp Tyr Ile Pro Lys Glu Val Lys Tyr Lys Phe Leu Gln Asn Pro
        35                  40                  45

Gln Phe Ser Leu Cys Phe Ser Glu Ser Ile Pro Thr Pro Ser Asn Arg
    50                  55                  60

Glu Glu Thr Gln Gln Lys Ser Asn Leu Glu Leu Leu Met Ile Ser Leu
65                  70                  75                  80

Leu Leu Ile Met Ser Trp Leu Glu Pro Val Gln Val Leu Arg Ser Val
                85                  90                  95

Phe Ala Asn Ala Leu Ile Tyr Gly Ala Ser Asp Ser Phe Val Arg Asp
            100                 105                 110

Leu Leu Lys Asp Leu Met Glu Gly Ile Gln Thr Leu Ile Gly Arg Leu
        115                 120                 125

Glu Asp Gly Ala Pro Arg Ala Gly Arg Ala Phe Lys Phe Val Val Ala
    130                 135                 140

Ala Phe Ala Thr Asn Ser His Asn Asp Asp Ala Leu Leu Lys Asn Tyr
145                 150                 155                 160
```

```
Gly Leu Leu Tyr Cys Phe Arg Lys Asp Met Asp Lys Val Glu Thr Phe
            165                 170                 175

Leu Arg Ile Val Gln Cys Arg Ser Val Glu Gly Ser Cys Gly
            180                 185                 190

<210> SEQ ID NO 13
<211> LENGTH: 190
<212> TYPE: PRT
<213> ORGANISM: Artificial sequence
<220> FEATURE:
<223> OTHER INFORMATION: synthetic

<400> SEQUENCE: 13

Phe Pro Thr Ile Pro Leu Ser Arg Leu Phe Asp Asn Ala Met Leu Arg
1               5                   10                  15

Ala His Arg Leu His Gln Leu Ala Phe Glu Thr Tyr Lys Val Phe Glu
            20                  25                  30

Glu Trp Tyr Ile Pro Lys Glu Val Lys Tyr Lys Phe Leu Gln Asn Pro
        35                  40                  45

Gln Phe Ser Leu Cys Phe Ser Glu Ser Ile Pro Thr Pro Ser Asn Arg
    50                  55                  60

Glu Glu Thr Gln Gln Lys Ser Asn Leu Glu Leu Leu Met Ile Ser Leu
65                  70                  75                  80

Leu Leu Ile Met Ser Trp Leu Glu Pro Val Gln Val Leu Arg Ser Val
                85                  90                  95

Phe Ala Asn Ala Leu Val Tyr Gly Ala Ser Asp Ser Phe Val Arg Asp
            100                 105                 110

Leu Leu Lys Asp Leu Lys Glu Gly Ile Gln Thr Leu Ile Gly Arg Leu
        115                 120                 125

Glu Asp Gly Ala Pro Arg Ala Gly Arg Ala Phe Lys Phe Val Val Ala
    130                 135                 140

Ala Phe Ala Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
            165                 170                 175

Leu Arg Ile Val Gln Cys Arg Ser Val Glu Gly Ser Cys Gly
            180                 185                 190

<210> SEQ ID NO 14
<211> LENGTH: 190
<212> TYPE: PRT
<213> ORGANISM: Homo sapiens

<400> SEQUENCE: 14

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95
```

-continued

```
Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly
            180                 185                 190
```